(12) United States Patent
Michaeli

(10) Patent No.: US 6,328,694 B1
(45) Date of Patent: Dec. 11, 2001

(54) ULTRASOUND APPARATUS AND METHOD FOR TISSUE RESONANCE ANALYSIS

(75) Inventor: David Michaeli, Ashkelon (IL)

(73) Assignee: Inta-Medics, LTD, Ashkelon (IL)

( * ) Notice: Subject to any disclaimer, the term of this patent is extended or adjusted under 35 U.S.C. 154(b) by 0 days.

(21) Appl. No.: 09/578,881

(22) Filed: May 26, 2000

(51) Int. Cl.$^7$ .................................. A61B 8/00; A61B 5/00
(52) U.S. Cl. ......................... 600/438; 600/451; 600/561
(58) Field of Search ...................... 600/407, 420, 600/424, 431, 437, 438, 442, 443, 449, 451, 504–506, 561, 562; 73/625, 626, 772, 716

(56) References Cited

U.S. PATENT DOCUMENTS

| | | | |
|---|---|---|---|
| 3,872,858 | 3/1975 | Hudson et al. | 128/2 V |
| 4,984,567 | 1/1991 | Kageyama et al. | 128/660.02 |
| 5,117,835 | 6/1992 | Mick | 128/748 |
| 5,388,583 | 2/1995 | Ragauskas et al. | 128/661.05 |
| 5,617,873 | 4/1997 | Yost et al. | 128/748 |
| 5,840,018 | 11/1998 | Michaeli | 600/300 |
| 5,873,840 | 2/1999 | Neff | 600/561 |
| 5,919,144 | 7/1999 | Bridger et al. | 600/561 |
| 6,086,533 | * 1/2000 | Madsen et al. | 600/438 |
| 6,146,336 | * 11/2000 | Paulat | 600/561 |
| 6,231,509 | * 5/2001 | Johnson et al. | 600/438 |

FOREIGN PATENT DOCUMENTS

| | | | |
|---|---|---|---|
| 19600983 | 5/1997 | (DE) | A61B/5/03 |
| 10328189 | 12/1998 | (JP) | A61B/8/06 |
| 753426 | 8/1980 | (SU) | A61B/5/00 |
| 776603 | 11/1980 | (SU) | A61B/5/02 |
| 904670 | 2/1982 | (SU) | A61B/10/00 |
| 1142106 | 2/1985 | (SU) | A61B/10/00 |
| 1734695 | 5/1992 | (SU) | A61B/8/00 |
| 2032378 | 4/1995 | (SU) | A61B/8/06 |
| 2108063 | 4/1998 | (SU) | A61B/8/00 |
| 9963890 | 12/1999 | (WO) | A61B/8/04 |

OTHER PUBLICATIONS

U.S. Patent application No. 09/307,568 filed May 10, 1999.

Czosnyka, M. et al., Hemodynamic Characterization of Intracranial Pressure Plateau Waves in Head–injured Patients, J. Neurosurg 91:1 (Jul. 1999) 11–19.

Hagen–Ansert, S., *Textbook of Diagnostic Ultrasonography* (4$^{th}$ edition), Mosby, St. Louis, 682–86.

Hanlo, P.W., Value of transcranial Doppler indices in predicting raised ICP infantile hydrocephalus, Child's Nerv Syst 11 (1995) 595–603.

Newell, David W., Transcranial Doppler Measurements, New Horizons 3:3 (Aug. 1995) 423–431.

(List continued on next page.)

*Primary Examiner*—Marvin M. Lateef
*Assistant Examiner*—Ali M. Imam
(74) *Attorney, Agent, or Firm*—Davidson, Davidson & Kappel, LLC

(57) ABSTRACT

An ultrasound probe is placed on the head of a patient, and is used to generate an ultrasound pulse which propagates through the skull and brain of the patient, and is reflected off of the skull and soft tissue lying in a path perpendicular to the ultrasound probe. The reflected signals are received by the ultrasound probe, and then processed in a known manner to generate an echo encephalogram (Echo EG) signal, which is plotted as a function of amplitude vs. distance. A portion of the Echo EG signal is then selected, and the Echo EG signal is integrated over the selected portion to generate an echo pulsograph (EPG) signal. An electrocardiograph (ECG) signal for the patient is also generated in a known manner. Using the ECG signal as a reference, the EPG signal is used to provide information regarding the physiological state of the tissue at a depth from the ultrasound probe corresponding to the selected portion of the Echo EG signal. In addition, the ultrasound probe is preferably a probe having a concave shaped transmitting and receiving surface.

37 Claims, 34 Drawing Sheets

OTHER PUBLICATIONS

Pranevicius, O. et al., Non–Invasive dynamic assessment of the elasticity of intracranial structures, 86 Acta Neurol. Sound (1992) 512–516.

Schmidt, Bernhard et al., Noninvasive Prediction of Intracranial Pressure Curves Using Transcranial Doppler Ultrasonography and Blood Pressure Curves, Stroke 28:12 (1997) 2465–72.

Schoser, Benedikt G.H. et al., The Impact of Raised Intracranial Pressure on Cerebral Venous Hemodynamics: a Prospective Venous Transcranial Doppler Ultrasonography Study J. Neurosurg. 91 (Nov. 1999) 744–749.

Uneno, T. et al., Nonivasive Measurement of Pulsatile Intracranial Pressure Using Ultrasound, Acta Neurochir 71 (1998) 66–69.

D. Michael Z. Rosenbaum, Z.H. Rappaport, "Non–invasive Monitoring of Intracranial Pressure by Tissue Resonance Ultrasonic Analysis", International Conference on Recent Advances in Neurotraumatology (Nov. 20–23, 1999), pp. 107 and 159.

Moreno, Jose A., et al. (2000) Evaluating the Outcome of Severe Head Injury With Transcranial Doppler Ultrasonography. *Neurosurgical Focus* (8) 1.

Blackwell R. (1985) Chapter 1, Apparatus and General Scanning Technique. *Clinical Diagnostic Ultrasound.* Blackwell Scientific Publications.

Woodcock J.P. (1985) Chapter 13, Doppler Ultrasound in the Investigation of Lower Limb Arterial Disease. *Clinical Diagnostic Ultrasound.* Blackwell Scientific Publications.

Fish P.J. (1985) Chapter 14, Doppler Imaging. *Clinical Diagnostic Ultrasound.* Blackwell Scientific Publications.

Sheldon C.D. (1985) Chapter 15, Doppler ultrasound in Cerebrovascular Disease. *Clinical Diagnostic Ultrasound.* Blackwell Scientific Publications.

Grandolfo M. and Vecchia P. (1987) Fundamentals of Acoustic Wave Theory. *Ultrasound Medical Applications, Biological Effects, and Hazard Potential.* pp. 13–28. Plenum Press.

Carstensen E. L., Aspects of Nonlinear Acoustics Which Are Important in Biomedical Ultrasound. pp. 61–71 *Department of Electrical Engineering, University of Rochester.* Rochester, New York.

Benwell D.A., Sources and Applications of Ultrasound. pp. 29–47. *Radiation Protection Bureau, Health and Welfare Canada.* Ontario, Canada.

* cited by examiner t = 147 msec.
T = 594 msec.
t/T = 0,24

$t = 281$
$T = 645$
$ICP = 370 \frac{281}{645} [+9] + [-9]$
$= [370 \cdot 0.435] + [-9]$
$= [160.6] + [-9]$
$= 151.6 \text{ mm } H_2O$
$= 151.6 : 13.6 =$
$= 11.14 \text{ mmHg}$
$= 11 \text{ mm Hg}$ Normal ICP
10–12 mm Hg —— II Resonance (Normal Venous output)
- - - level 1
— - — I Resonance $t = 443.5$ msec
$T = 635$ msec
$\dfrac{t}{T} = 0.7$ $\rho = 425$
$ICP = 425 \times 0.7 =$
$[-9] = 296.5 \ -9 =$
$= 287.5 : 13.6 =$
$= 21.14$ mm Hg.

$t = 443.5$ msec
$T = 635$ msec
$\frac{t}{T} = 0.7$ $\rho = 425$
$ICP = 425 \times 0.7$
$[-9] = 296.5 \quad -9$
$= 287.5 : 13.6$
$= 21.14$ mm Hg.

$t = 820$ msec
$T = 942$ msec
$t/T = 0.187$

- II Resonance Frequency (28Hz)

- $\rho = 780$
  $ICP = 780 \times \dfrac{820}{942} + [-9]$
  $= 780 \times 0.87 + [-9]$
  $= 678.6 - 9 = 669.6$
  $= 669.6 : 13.6 = 49.2$ mm Hg

ULTRASOUND APPARATUS AND METHOD FOR TISSUE RESONANCE ANALYSIS

RELATED APPLICATIONS

This application is related to U.S. Pat. No. 5,840,018, entitled NON-INVASIVE REAL TIME DIAGNOSIS OF MIGRAINE, and U.S. Pat. application Ser. No. 09/307,568, filed May 10, 1999, entitled NONINVASIVE MONITORING OF INTRACRANIAL PRESSURE, the entire disclosures of which are hereby incorporated by reference. It should be noted that the inventor of the present invention, Dr. David Michaeli is also known as Dr. David Mikheslashvili and Dr. David Michelashvili.

FIELD OF THE INVENTION

The present invention relates to the field of ultrasound apparatuses and methods for non-invasive medical diagnostics and treatment.

BACKGROUND OF THE INVENTION

In connection with performing medical diagnostics on the brain, it is often helpful to measure the variation, contraction or dilation, of blood vessels in the brain.

Currently known methods involve injection of radioactive or contrast-enhancing substances into the bloodstream in order to observe and learn about variations in blood flow in the brain between migraine attacks and normal conditions. Examination is also possible by the invasive method of introducing probes (electrodes) directly into the brain.

Currently known measurement methods for measuring blood flow to and in the brain include Isotope Diagnosis (ID) and Transcranial Doppler ultrasonography (TCD). Isotope Diagnosis is invasive and can only be performed by intermittent sampling measurements, rather that continuous measurement in real-time.

TCD is noninvasive and does give real-time measurement. However, the accuracy of the measurement is highly dependent upon the angle of the probe relative to the skull, and the skill of the operator. In addition, TCD does not measure the volumetric velocity of the blood flow and does not give precise measurement of the contraction or dilation of blood vessels in the brain. This imprecision is caused by the fact that TCD can only be used to observe a sector or large area in the brain, instead of a localized point. In addition, TCD uses ultrasound waves at a frequency of 2 MHz, which, for an estimated 15–40% of the population, do not actually reach the interior of the cranium, because of high attenuation of the ultrasound waves in the bone tissue of the cranium. In those cases, where there is a response from the skull or via "acoustic windows," such as the temporal bones (orbital regions or foramen occipital magna), the acoustic reflections detected are only from the magistrial and proximal blood vessels. In addition to these reflected signals, this method also detects reflections from the brain and from other, non-cranial, blood vessels. The result is a noisy signal that does not allow precise determination of the depth of the measurement point. This does not allow measurement of individual blood vessels or their blood flow with any precision. Use of ultrasound technology as a diagnostic tool is discussed, inter alia, in the book entitled "Textbook of Diagnostic Ultrasonography," 4.sup.th edition, by Mosby, pages 682–686.

It is also useful in connection with medical diagnostics of the brain to initially determine, and then monitor over time, the pressure in the brain. This pressure is commonly referred to in the art as intra-cranial pressure.

As a general rule, tissues in the body swell when traumatized. In order to heal, such tissues require oxygen. There are special circumstances with respect to brain tissue which makes the situation even more critical. The brain rests inside a bone casing, and there is little or no room for it to expand. When the brain swells, it experiences more trauma. Because it is encased within the skull, the swelling of the brain causes parts of the brain to be compressed. This compression decreases the blood flow and oxygen to parts of the brain which, in turn, causes more swelling. The more damage the brain receives, the more oxygen it needs, and the more it swells. Swelling is caused, e.g., by leakage from blood vessels. This leads to a rise in pressure within the brain. This rise in pressure rapidly equals the arterial pressure, thereby effecting the blood flow to the brain. The diffused pressure which decreases blood flow affects the ability of the cells within the brain to metabolize properly. The cells are unable to eliminate toxins, which toxins then accumulate in the brain. This phenomenon leads to a spiraling effect, which in effect is what kills brain-injured individuals who do not get prompt medical attention.

In response to a trauma, changes occur in the brain which require monitoring to prevent further damage. The size of the brain frequently increases after a severe head injury. This is referred to in the art as "brain swelling" and occurs when there is an increase in the amount of blood in the brain. Thereafter, water may collect in the brain (referred to in the art as "brain edema"). Both brain swelling and brain edema result in excessive pressure in the brain. The pressure in the brain is referred to in the art as intracranial pressure ("ICP"). It is essential that excessive ICP be identified and monitored so that it can be immediately treated. Treatment of brain swelling can be difficult, but it is very important because brain swelling in turn causes reduced amounts of both oxygen and glucose available to the brain tissue. Oxygen and glucose are both required by the brain to survive. The cranial cavity of the skull contains approximately 78% brain, 12% blood and vessels, and 10% cerebrospinal fluid (CSF). Intracranial volumes enclosed within the rigid container of the skull are fixed. An increase in the volume of one of these components requires an equivalent decrease in another of these components in order for the volume in pressure to remain constant. Increases in ICP occur as a result of this volume-pressure relationship. When there is an increase in any of these three components, the body tries to compensate by reabsorbing CSF and decrease intracellular volume.

In order to treat excessive ICP, physicians have a number of different methods available at their disposal, including the use of medications which help draw fluid out of the brain and into blood vessels; medications which decrease the metabolic requirements of the brain; medications which increase blood flow into the brain; and surgical procedures which are used to either reduce small amounts of fluid or remove the damaged brain tissue.

Surgical procedures further include removing any hematomas (blood clots) which are pressing on the brain, or surgically repairing damaged blood vessels to stop any further bleeding. In severe cases, portions of the brain that have been damaged beyond recovery may be removed in order to increase chances of recovery for the healthy portions of the brain. A shunt or ventricular drain may be used to drain off excess fluids. The overall goal of the neurosurgeon is to maintain blood flow and oxygen to all parts of the brain, thereby minimizing the damage and increasing the prospect of survival and recovery.

The normal values for intracranial pressure (ICP) at the level of foramen of Monro are approximately 90–210 mm of CSF in adults and 15–80 mm of CSF in infants. Increased ICP can occur as a result of an increased mass within the limited volume of the cranium. Examples include an increase in CSF volume, cerebral edema, and growing mass lesions such as tumors and hematomas. Cerebral edema is the increase in brain tissue water causing swelling. It may occur secondary to head injury, infarction or a response to adjacent hematoma or tumor. Uncorrected increased ICP can lead to further brain damage due to the pressure and inadequate blood perfusion of neurological tissues. The treatment for increased ICP includes removing the mass (tumor, hematoma) by surgery, draining CSF from the ventricles by a drain or a shunt, hyperventilation, steroids, osmotic dehydrating agents, and barbiturates.

Increased ICP will reduce cerebral blood flow, leading to ischemia. If blood flow is constricted for more than four minutes, an individual can experience irreversible brain damage. With constricted blood flow, cells become damaged, leading to more edema, causing more increased ICP.

The principle causes of elevated ICP include traumatic head injury (e.g., edema, intracranial hemorrhage, and hydrocephalus), infection, and tumors.

Treatment of elevated ICP can be accomplished by CSF drainage; decreasing the edema via the use of strong drugs such as diuretics; ventilation (mechanical and hyperventilation); cerebral perfusion pressure control (blood pressure control, fluid restriction); and promoting venous blood return; and intracranial surgery.

Most clinicians consider 20 mm Hg as the upper limited of acceptable ICP, beyond which treatment is initiated. The key to treatment is to control cerebral perfusion pressure (CPP) or the adequate flow of blood and oxygen to the brain cells. It has been shown that by monitoring ICP, treating brain edema and giving appropriate treatment, death and disability in humans can be decreased by more than 50%. Despite this positive outcome, monitoring of ICP was shown to be done in only 30% of patients with severe head injury, according to a survey of U.S. Trauma Centers.

The United States market for head injury is substantial with several unmet needs. In the United States, there are approximately two million cases of head injury per year. There are approximately 60,000 deaths per year due to head injury, with 500,000 hospital admissions per year and 20,000 in-hospital deaths per year due to head injury. Approximately 80,000 head injury survivors per year have a significant loss of function and require long-term medical and rehabilitation care. In fact, head injury is the leading cause of death and disability in ages 1–44. There are over 100,000 neurosurgical procedures done per year in the United States.

In the case of a head trauma, ICP can change significantly in a matter of minutes. Significant changes in ICP may also occur hours, days, or weeks, from diagnosis of the underlying trauma or disease state. It is therefore advantageous to continually monitor the ICP of a patient in an emergency room setting, in a surgical setting, and at a patient's bedside.

Currently, the vast majority of ICP measurements are performed invasively, using needles, catheters, and implants.

In lumbar puncture, a needle is inserted at the base of the spinal column, to monitor the pressure of the fluid in the spinal column. This pressure may not reflect accurately the ICP, because there may be a blockage between the patient's head and the base of the patient's spinal column.

A second invasive method of monitoring ICP is to make a burr hole 5–10 mm in diameter in the patient's skull and to introduce a catheter to one of the lateral ventricles via the hole. The pressure of the cerebrospinal fluid (CSF) in the ventricle is measured directly by a transducer via the catheter. This procedure may cause a hemorrhage that blocks the penetrated ventricle. In addition, if CSF enters the catheter, the accuracy of the pressure reading is impaired.

In a related invasive method, the catheter is held in place by a threaded fitting that is screwed into the patient's skull. A saline solution is introduced to the catheter and the pressure of the saline solution is measured using an appropriate transducer. If insufficient care is taken to preserve antiseptic conditions, this procedure may lead to infection of the patient's brain. Furthermore, the threaded fitting may penetrate the patient's brain, causing damage to the patient's brain.

In both of the latter two invasive methods, the catheter must be removed after five days. Therefore, these methods cannot be used for long term (several months) monitoring of ICP of patients in comas.

In a fourth invasive method, a fiber optic device, with a sensor at the tip of a fiber optic cable (available from Codman, a Johnson & Johnson Company), is inserted in the patient's cerebral tissue, in the patient's subdural space, or in the patient's intraventricular and epidural space. If a blood clot forms on the sensor, or if the fiber optic cable bends too sharply or breaks, the device may give a spuriously high pressure reading.

In short, the prior art invasive methods of measuring ICP are unreliable, may lead to infection, and cannot be used for more than five consecutive days.

There are also additional drawbacks to invasive techniques. Due to the problems associated with invasive techniques for measuring ICP, standard medical protocol is to monitor ICP only for patients with scores of 8 or less on the Glasgow Coma Scale. It would be useful to monitor ICP of patients with Glascow scores higher than 8. It would also be useful to monitor ICP in healthy individuals under severe environmental stress, such as astronauts, divers, and submariners.

A number of non-invasive techniques for measuring ICP have been proposed in the literature. However, for a variety of reasons, none of these methods have found significant commercial use.

For example, TCD has been used to provide a non-invasive, qualitative indication of variations in intra-cranial pressure ("ICP"). The use of TCD in the measurement of ICP is described, for example, in Schoser B. G. et al., "Journal of Neurosurgery" 1999, November: 91(5): 744–9; Nevell D. W., "New Horizons" 1995 August:3(3) 423–30, and PCT Publication WO 99/63890 to Taylor. Unfortunately, TCD only provides a qualitative indication of variations in ICP, and does not provide a quantitative measurement of ICP.

Attempts have been made to use TCD to obtain a quantitative measure of ICP using pulsatile (P.I.) and resistant (R.I.) indexes. However, according to the investigations done by Czosnika M. et al. "Journal of Neurosurgery", 1999, July 91 (1) 11–9; and Hanlo P. W. et al. Child Neuro. Syst. 1995; Oct; 11(10); 595–603 there is no linear relations between ICP and TCD indexes. Moreover, the accuracy of these TCD measurements is low, particularly in patients with raised ICP.

Additional non-invasive methods for measuring ICP include "classical acoustic methods" based on the transfer of acoustic waves via the skull, as discussed in U.S. Pat. Nos. 5,117,835 to Edvin et al, and in O. Pranevicius et al, Acta Neurol. Sound 1992:86:512–516; and the Pulse Phased Locked Loop (PPLL) method as discussed in U.S. Pat. No. 4,984,567 to Kagaiama and in Uenot et al. "Acta Neurochir. Suppl." Wien 1998:71:66–9. These methods infer ICP by monitoring dura mater, a thick and dense inelastic fibrous membrane which lines the interior of the skull and extends inward to support and protect the brain.

However, classical acoustic and PLL methods are dependent upon the patients' skull condition (e.g. skull fractures, skull thickness, and pneumocephalus) as well as the patient's body temperature and environmental temperature. Each of these variables may lead to largely inaccurate ICP measurements. An additional disadvantage of these methods derives from their use of the thickness of dura mater as an indication of ICP despite the fact that dura mater, in some patients, may be adhered to the internal table of the skull. Moreover, the ICP waves generated by these methods do not resemble the ICP waves generated by invasive methods. This raises additional problems because doctors and nurses are not accustomed to reading and interpreting these types of ICP waveforms.

U.S. Pat. No. 5,617,873 to Yost et al, purports to describe an indirect, noninvasive method of monitoring ICP. Two changes in CSF volume are induced, and the associated changes in ICP are measured.

Therefore, presently known methods of quantitatively determining ICP remain predominantly invasive despite the existence of various non-invasive methods in the scientific and patent literature, and the need for a non-invasive alternative.

In addition to ICP, it is also useful in medical diagnostics to diagnose and monitor midline shift. The presence of midline shift provides an indication that some space filling lesion has caused distortion of the brain contents and, upon identification of the particular responsible mass, is normally cause for prompt intervention. Acute insults would be expected to initially induce elevation of ICP, with midline shift occurring later. Midline shift and ICP are thought to be closely related indicators of functional brain status following head trauma. However, it is generally believed that midline shift is a somewhat less sensitive indicator of acute unilateral space filling lesions than ICP. On the other hand, midline shift could well be a more sensitive predictor of slowly developing lesions such as brain tumors, where it serves as a confirmatory diagnostic tool, secondary to CT and MRI scans.

Under normal conditions, the brain sits in the middle of the cranial cavity equally distant from the outer limits of either hemisphere of the cavity. The brain is protected on all sides by cerebrospinal fluid.

A patient can experience edema, hemorrhaging/ hematoma or some other lesion in the brain that will result in a shift away from midline, away from the hemisphere where the mass has formed. The key events that can cause such a shift are: traumatic head injury; post surgical hemorrhaging; infection; cerebrospinal fluid buildup; and/or the presence of a tumor. The shift may occur very quickly following the event or after a period of time.

Midline shift is currently measured by CT Scan. Determining midline shift is considered an important diagnostic tool by both neurosurgeons and emergency medicine physicians. A patient in the emergency room of a hospital presenting with a head injury and a low Glasgow Coma Scale score (8 or less), would be sent for a CT Scan. If the CT Scan is abnormal, showing a mass with or without midline shift, the neurosurgeon would be consulted. Sometimes the initial CT Scan is normal and the patient needs to be monitored. The question always arises as to what point does the patient get a second or third CT Scan. CT Scans are expensive, and the patient is subjected to radio-opaque dyes and contrast agents. Sending a seriously injured patient from the ER for a CT Scan can take the patient away from maximum emergency medicine care. The report on midline shift is typically fed back to the emergency medicine physician by the radiologist and presented qualitatively by categorizing the shift as minimal or substantial. In contrast, a neurosurgeon can read the CT Scan directly and determine the amount of shift (typically in millimeters).

Therefore, it would be advantageous to provide a portable, inexpensive technique to quantify midline shift which would be readily used in an emergency room or at a patient's bedside.

SUMMARY OF THE INVENTION

In general, all of the prior art non-invasive methods described above derive ICP from data relating to only one of the structures in the intra-cranial space (e.g., brain tissue or ventricles or cisterns or vessels). TCD, for example, evaluates ICP only on the basis of certain properties of intra-cranial vascular system (P.I. and R.I.). This mono-causal approach makes TCD inherently inaccurate because it fails to take into account that ICP is a multi-causal parameter which is dependent on the characteristics of different areas of intra-cranial space and the different physiological relations between them. These factors include the brain's tissue mass, the ventricular, cisternal and subarachnoid reserve space volume within the skull, the level of intra-cranial blood volume, and the input-output balance of intra-cranial blood flow.

Therefore, in order to provide an accurate, non-invasive measurement of ICP, it is important to take an integrated approach, which utilizes information regarding multiple contents and areas of intra-cranial space, and the mechanical and physiological relationship between them.

In view of the deficiencies in the prior art techniques discussed above, it is an object of the present invention to provide a non-invasive system for measurement of ICP which achieves some or all of the following criteria:

1. Provide a direct and real visualization of ICP waves in real-time which is visually similar to the ICP waves generated by current invasive methods, while providing long term registration and recording of ICP waves.
2. Provide high accuracy and resolution of measurement in real-time using an integrated approach which utilizes information regarding multiple contents and areas of intra-cranial space, and the mechanical and physiological relationship between them.
3. Provide accurate measurements that are not operator dependent and not dependent on the angle insonation of the ultrasound pulses.
4. Provide automatic real-time measurement of ICP.
5. Provide a device which can be operated by nurses without the assistance of a physician.
6. Provide a device which is cost effective.

The present invention is derived, in part, from the recognition that the soft tissue and fluid compartments of the brain each exhibit characteristic resonant responses to arterial pressure pulses that radiate through the tissues of the body. When a tissue of interest is stimulated by an ultrasound pulse, the nature of the reflected ultrasound signal will depend upon the resonant state of the tissue. Therefore, by properly processing and interpreting the reflected signal, it is possible to derive information relating to the physiological state of the tissue of interest.

In accordance with the present invention, an ultrasound probe is placed on the head of a patient, and is used to generate an ultrasound pulse which propagates through the skull and brain of the patient, and is reflected off of the skull and soft tissue lying in a path perpendicular to the ultrasound probe. The reflected signals are received by the ultrasound probe, and then processed in a known manner to generate an echo encephalogram (Echo EG) signal, which is plotted as a function of amplitude vs. distance. In this regard, the distance ordinate is obtained by converting the time delay from transmission of the ultrasound pulse to receipt of the reflected signals to the distance from the ultrasound probe to the point of reflection. A portion of the Echo EG signal is then selected, and the Echo EG signal is integrated over the selected portion to generate an echo pulsograph (EPG) signal. The selected position of the wave form corresponds to a selected distance from the ultrasound probe, and therefore corresponds to a discrete location in the brain which lies at a depth equal to the selected distance and in a path perpendicular to the probe. In accordance with one embodiment of the present invention, the selected portion has a width of 0.3 to 1.3 $\mu$s, preferably a 0.3 to 1 $\mu$s, and most preferably, a 0.5 to 0.7 $\mu$s (corresponding to approximately one pixel and a depth of resolution of 0.5 mm). An electrocardiograph (ECG) signal for the patient is also generated in a known manner. Using the ECG signal as a reference, the EPG signal is used to provide information regarding the physiological state of the tissue at a depth from the ultrasound probe corresponding to the selected portion of the Echo EG signal.

Preferably, the ultrasound probe is placed either on the forehead of a patient, or on the back of the skull. When placed on the forehead, it is most preferably placed between 2 and 6 cm above the bridge of the nose when the desired point of interest is the third ventricle. In addition, the ultrasound pulse preferably has a pulse width between about 100 and 1000 ns, and a output intensity between about 50 and 300 mW/cm$^2$. It has been discovered that this pulse width and position provides a substantially improved reflected signal as compared to the prior art methods described above. Within the above ranges, it should be noted that shorter pulse widths are generally preferable for investigating areas of the brain which are closer to the portion of the skull adjacent to the probe, and longer pulse widths are generally preferably for investigating areas of the brain which are further from the portion of the skull adjacent to the probe.

In addition, the ultrasound probe is preferably a probe having a concave shaped transmitting and receiving surface. As compared to a conventional ultrasound probe having a flat transmitting and receiving surface, the concave shaped probe in accordance with the present invention focuses the ultrasound signal on a significantly smaller area of brain tissue. For example, in accordance with the preferred embodiment of the present invention, the concave probe has cylindrical surface with a diameter of 28 mm a circular concave shaped transmitting and receiving surface extending to a depth of 1.3 mm. This probe will focus the ultrasound signal on an area of about 0.5×1.5 mm (0.75 mm$^2$) as compared with an area of 5 mm$^2$ for a conventional flat probe of the same dimensions. Therefore, in the preferred embodiment described in more detail below, the concave shaped probe allows the system in accordance with the present invention to monitor an 0.5×1.5×0.5 mmm portion of the brain.

In accordance with one embodiment of the present invention, the EPG signal is used to provide a quantitative measure of intra cranial pressure (ICP) at a location of interest in the brain. In accordance with this embodiment, ICP is defined as follows:

$$ICP=\rho(t/T)*[t/T]-\beta$$

wherein T is the time period between cardiac systoles, t is the time from the beginning of brain (e.g. cerebral) pulsatility to the peak following a venous notch (point "B"), $\beta$ is a constant having a value of 9 mm H$_2$O, and $\rho(t/T)$ is a variable function greater than 0 and less than 1, which is characteristic of the particular brain tissue being monitored. For example, when measuring the ICP at the third ventricle of the brain, the central cerebral vein, and the lateral ventricle trigon or suprasellar cistern, $\rho(t/T)$ is a substantially quadratic function, having a value of about 373 at t/T=0.3, a value of between 373 and 450 at t/T>0.3 and <1, and a value of less than 373 at t/T<0.2. Most preferably, $\rho(t/T)$ has a value of about 325 at t/T=0.1, a value of between about 350 and 375 at t/T=0.2, and a value of less than 300 at t/T<0.05. In accordance with a further aspect of this embodiment, a frequency spectral and resonance analysis is performed on the EPG signal, and the second resonant frequency is used to more accurately identify the venous notch. Most preferably, the frequency spectral analysis is a discrete fourier transform.

In addition, the second resonant frequency is preferably used to further refine the calculated value for ICP. In this regard, for patients having a second resonant frequency of less than 4 Hz, ICP=$\rho(t/T)*[t/T]$, and $\rho(t/T)$ is a substantially quadratic function, having a value of about 150 at t/T=>0.6, a value of between 100 and 150 at t/T>0.1 and <0.6, and a value of less than 100 at t/T<0.1.

For patients having a second resonant frequency of greater than 20 Hz, ICP=$\rho(t/T)*[t/T]-\beta$, and $\rho(t/T)$ is a substantially linear function for t/T greater than about 0.5, having a value of about 275 at t/T=0.5 and a value of about 675 at t/T=0.7.

In accordance with another embodiment of the present invention, the EPG signal is used to determine the width and position of ventricles and blood vessels. In accordance with this embodiment, opposing walls of a ventricle or blood vessel are identified by placing an ultrasound probe on an appropriate portion of the skull of a patient; transmitting an ultrasound pulse from the ultrasound probe into the skull of the patent; receiving a reflected signal from said ultrasound pulse; processing said reflected signal to generate a digital echo encephalogram signal; selecting a dominant portion of said echo encephalogram signal corresponding to the vessel or ventricle of interest; and integrating the echo encephalogram signal over the selected portion to generate an echo pulsogram signal, said echo pulsogram signal providing an indication of the pulsatility of a portion of the brain of the human patient corresponding to the selected portion of the echo encephalogram signal. The echo pulsogram signal is then identified as either a positive phase signal (i.e., a signal in which the maximum amplitude following a cardiac systole has a positive value) or a negative phase signal (i.e., a signal in which the maximum amplitude following a cardiac systole has a negative value). If the echo pulsogram signal has a positive phase, then the selected portion of the echo encephalogram is identified as corresponding the outer wall of the vessel or ventricle relative to the ultrasound probe. If the echo pulsogram signal has a negative phase, then the selected portion of the echo encephalogram is identified as corresponding the near wall of the vessel or ventricle relative to the ultrasound probe.

If a positive phase signal was identified, then a second portion of the echoencephalogram signal is selected which corresponds to a location in the brain which is closer to the ultrasound probe than the dominant portion selected previously. The echo encephalogram signal is then integrated over the selected second portion to generate an echo pulsogram signal. If the echo pulsogram signal is a negative phase signal, then the second portion of the echoencephalogram is identified as corresponding to the near wall of the vessel or ventricle. If the echo pulsogram signal is a positive phase signal, then successive second portions of the encephalogram are selected, which correspond to locations in the brain which are successively closer to the ultrasound probe, until a negative phase signal is identified.

If a negative phase signal was derived from the dominant portion of the echo encephalogram, then a second portion of the echoencephalogram signal is selected which corresponds to a location in the brain which is farther from the ultrasound probe than the dominant portion selected previously. The echo encephalogram signal is then integrated over the selected another portion to generate an echo pulsogram signal. If the echo pulsogram signal is a positive phase signal, then the second portion of the echoencephalogram is identified as corresponding to the far wall of the vessel or ventricle. If the echo pulsogram signal is a negative phase signal, then successive second portions of the encephalogram are selected, which correspond to locations in the brain which are successively farther from the ultrasound probe, until a positive phase signal is identified.

As set forth above, the echo encephalogram signal is a function of amplitude vs. distance from the probe to point of reflection of the ultrasound pulse. Therefore, the dominant portion of the echo encephalogram can be identified as corresponding to a first distance from the site of the probe, and the second portion of the echo encephalogram can be identified as corresponding to a second distance from the site of the probe. In this manner, both the position and width of the ventricle or vessel of interest are identified.

In accordance with a further embodiment of the present invention, the presence or absence of midline shift in a brain of a human patient is identified by: placing an ultrasound probe on a temporal area of a first side of the skull of a patient; transmitting an ultrasound pulse from the ultrasound probe into the first side temporal area of the patent; receiving a reflected signal from said ultrasound pulse; processing said reflected signal to generate a digital echo encephalogram signal; selecting a first-side dominant portion of said echo encephalogram signal corresponding to a third ventricle of the patient; integrating the echo encephalogram signal over the selected portion to generate a first-side echo pulsogram signal, said echo pulsogram signal providing an indication of the pulsatility of a portion of the brain of the human patient corresponding to the selected portion of the echo encephalogram signal. The first-side echo pulsogram signal, which corresponds to the first-side dominant portion, is then identified as a positive phase signal or a negative phase signal as described above.

Then, an ultrasound probe is placed on a second, opposite temporal area of a patient and an ultrasound pulse from the ultrasound probe is transmitted into the opposite temporal area of the patent. The reflected signal is then received and processed to generate a digital echo encephalogram signal, and a second-side dominant portion of said echo encephalogram signal is selected which corresponds to the third ventricle of the patient. The echo encephalogram signal is then integrated over the selected portion to generate an second-side echo pulsogram signal. The second-side echo pulsogram signal, which corresponds to the second-side dominant portion, is then identified as a positive phase signal or a negative phase signal as described above. If the first and second side echo pulsograms have the same phase, then they are identified as corresponding to opposing walls of the third ventricle. The first-side dominant portion of the echo encephalogram can be identified as corresponding to a first distance from the first side temporal area, and the second-side dominant portion of the echo encephalogram can be identified as corresponding to a second distance from the second side temporal area. Based on the assumption that the third ventrical is substantially symetrical, and normally centered on the midline of the brain, the first distance should equal the second distance for a patient with no midline-shift. The midline shift in a patient can therefore be quantified as (first distance−second distance)÷2.

Preferably, the method also includes identifying the position of the opposing ventrical wall by locating the opposite phase signal (i.e. a positive phase signal if the dominant portion generated a negative phase signal, and vice versa) in the manner described above with regard to the method of identifying the width and position of a vessel or ventricle wall.

DETAILED DESCRIPTION OF THE PREFERRED EMBODIMENTS

Figure 1:
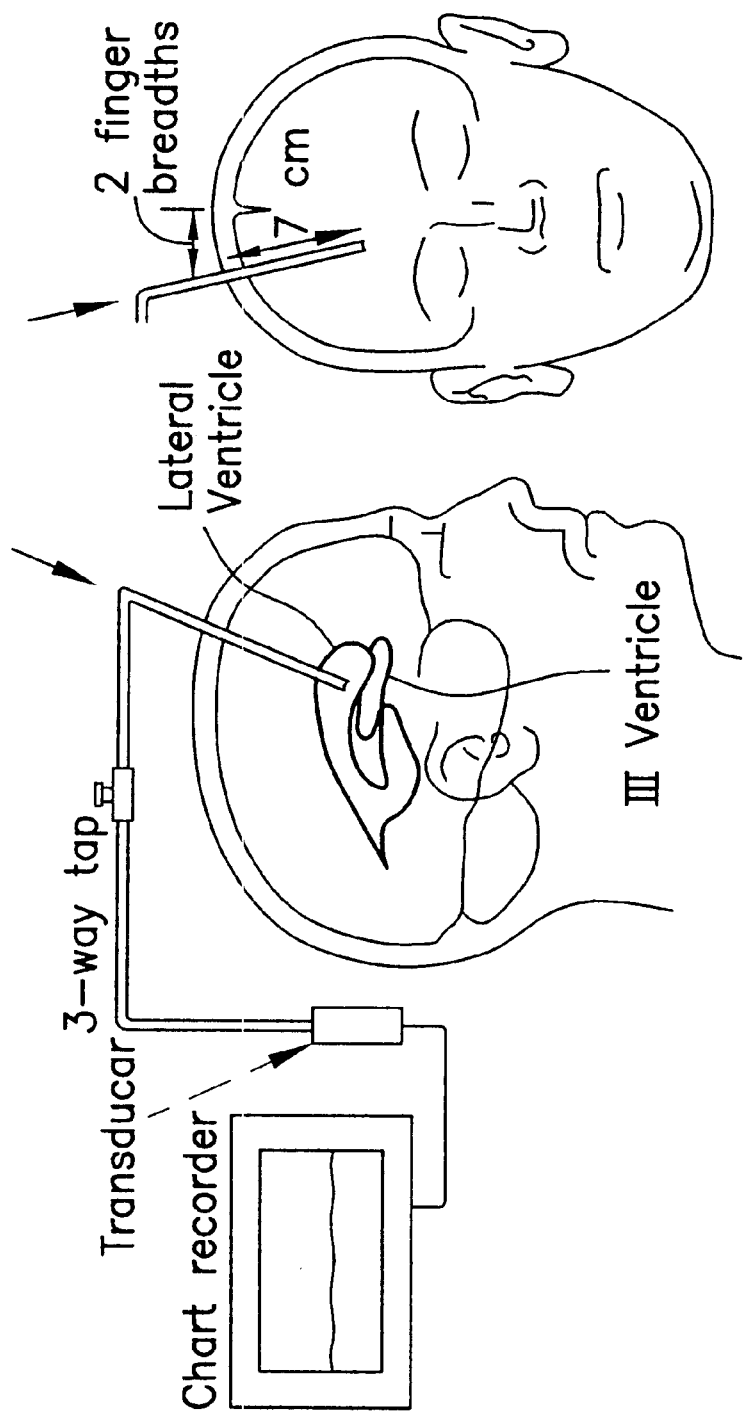
FIG. 1 shows a prior art technique for invasively measuring intra cranial pressure.

The present invention is directed in part to a novel ultrasonic technology which will be referred to herein as Tissue Resonance Analysis (TRA). This noninvasive technology provides information about the physical properties of body tissue and fluids. This TRA technology is capable of monitoring the functional status of tissues anywhere in the body, including tissues and fluids within the brain. Its ability to also monitor intracranial tissues and fluids constitutes a key advantage over other ultrasonic technologies whose signals cannot readily penetrate across the skull. Furthermore, the stimulation parameters, beam focusing, and sensor gates can all be modified to generate important diagnostic information about the physiological status of virtually any fluid space, tissue, or organ of interest.

TRA technology makes use of the fact that all soft tissues and fluid compartments exhibit their own characteristic resonant responses to arterial pressure pulses that radiate through the tissues of the body. When a target tissue is stimulated by specific ultrasound signals, the nature of the reflected ultrasound energy waves that bounce back from the tissue depends on the resonant state of the tissue. The pulsatile pattern of resonance responses of a tissue to specific ultrasonic stimulation is then collected and interpreted to provide information about the physiological state of the tissue of interest.

The TRA technology described herein can deliver many different frequencies of ultrasound energy at different intensities. The beams can also be focused onto those tissues or structural surfaces of interest. Customized ultrasound stimulation profiles can be developed that can characterize the response status of the target. This information is then transformed into quantitative measurements of tissue volume, pressure, compliance, elasticity, or hydration state.

TRA technology offers a noninvasive option of monitoring tissues and fluids within the central nervous system, and is an extremely versatile diagnostic tool that can be customized to provide quantitative information about the physiological status of essentially any soft tissues or fluid compartments of interest. This technology can be used for a wide variety of noninvasive diagnostic applications. The pathological conditions where this device could be used to aid in diagnosis and provide information to direct the most appropriate course of therapy, include but are not limited to the following: (i) Traumatic and Organic Injury of the Nervous System (including but not limited to intracranial pressure, intracerebral pressure, regional perturbations, birth trauma, cerebral palsy, midline shift, space filling brain lesions, brain edema, intracellular and interstitial, severe headache, differential diagnosis, spinal cord pathologies, disc prolapse, and cord stenosis); (ii) Blood Vessel Characteristics (including but not limited to migraine (excessive vasoconstriction of vasodilation), brain vessel tension (vasospasm following subarachnoid hemorrhage (e.g., as a predictor of stroke risk), brain vessel diameter, brain vessel capacitance, and intracranial aneurysm; (iii) Blood Flow Dynamics (including but not limited to linear blood flow, arterial volume blood velocity, venous blood flow velocity, brain death, coronary blood flow, coronary artery disease, and cardiac output); and (iv) miscellaneous other applications (including but not limited to cardiac excitationcontraction coupling, arrhythmias, intraocular pressure, glaucoma, intramuscular pressure: compartment syndrome, 3D imaging, noninvasive angiography, ultrasonic pulsatile tomography.

In order to place TRA technology in proper context for the detailed discussion that follows, it is helpful to review the structure and function of the human brain.

The Human Brain

The brain is composed of the Cerebrum, Cerebellum, and Brain Stem. The brain is separated from the skull via dura mater. Dura mater is a thick and dense inelastic fibrous membrane which lines the interior of the skull. Its outer surface is rough and fibrillated, and adheres closely to the inner surface of the bones. The dura mater extends into the cavity of the skull to support and protect the brain.

The Cerebrum, the part of the brain which is responsible for higher mental function, consists of two hemispheres separated by a longitudinal fissure, which, in a normal patient, is located at the mid-line of the skull. In this regard, the mid-line of the skull is a vertically extending plane equidistant between the left and right temporal areas of the skull.

Structurally, the brain is symmetrical, with identical left and right side structures in each hemisphere. In this regard, each hemisphere includes a respective frontal lobe, parietal lobe, temporal lobe, and occipital lobe, the names of which correspond the bones of the skull lying superficial to them. Functionally, however, there are significant differences between the right and left sides of the brain.

The hemispheres are connected by a large C-shaped bundle of fibers carrying impulses between them, the Corpus Callosum, and the Brain Stem. Almost at right angles to the longitudinal fissure, crossing the Cerebrum lateral and downward, is the Central Sulcus. Below the end of this Sulcus is the horizontal lateral fissure.

The Frontal Lobe lies above the lateral fissure in front of the Central Sulcus. Behind the Central Sulcus is the Parietal Lobe and behind that the Occipital Lobe, although there is no specific boundary between them laterally. Medially they are separated by the Parieto-Occipital Fissure. The Temporal Lobe is located below the lateral fissure and anterior to the Occipital Lobe.

The Cerebrum has an outer layer of gray matter, composed primarily of nerve cells, called the Cortex. Below this layer lie large bundles of nerve call processes, or fibers, the white matter. Embedded deep within the white matter are the Basal Ganglia, or Corpus Striatum, a group of nuclei which serve to coordinate motor and sensory impulses. The Cortex is occupied by association areas, which are devoted to integration of motor and sensory phenomena, advanced intellectual activities, such as abstract thinking, comprehension and execution of language, and memory storage and recall. Immediately anterior to the Central Sulcus lies the Precentral Gyrus, the center for voluntary motor movements. Immediately posterior is the somatic sensory area, or Postcentral Gyrus, set aside for conscious perception of general sensory phenomena. Above and below the Calcarine Sulcus on the medial side of the Occipital Lobe are the Cortical areas for vision. Auditory phenomena are localized to the upper part of the Temporal Lobe, opposite the somatic sensory area. Smell, or olfactory sensation, are associated with the inferior surface of the Temporal Lobe, although the Olfactory Nerve ends in the inferior portion of the Frontal Lobe.

The Cerebral hemispheres are hollow, each containing a lateral ventricle. The ventricles contain a vascular membrane, the Choroid Plexus, that secretes cerebrospinal fluid. Each lateral ventricle includes an anterior horn, a central part, a posterior horn, and an inferior horn. The anterior horn is anterior to the interventricular foramen. Its roof and anterior border are formed by the corpus callosum, its vertical medial wall by the septum pellucidum. The floor is formed by the head of the caudate nucleus. The central part extends from the splenium of the corpus callosum; medially, by the posterior part of the septum pellucidum; and below, by parts of the caudate nucleus, thalamus, choroid plexus and fornix. The posterior horn extends into the occipital lobe. Its roof is formed by fibers of the corpus callosum. The inferior (or temporal) horn traverses the temporal lobe. Its roof is formed by the white substance of the cerebral hemisphere. Along the medial border is the stria terminalis and the tail of the caudate nucleus. The amygdaloid nucleus bulges into the terminal part of the inferior horn. The floor and the medial wall are formed by the fimbria, the hippocampus and the collateral eminence.

The third ventricle is a narrow, vertical cleft between the two lateral ventricles. The lateral ventricles communicate with the third ventricle (which is the cavity of the Diencephalon), by way of interventricular Foramina. The Diencephalon, embedded in the inferior aspect of the Cerebrum, is situated on either side of the slit-like third ventricle. A thin membrane (the Tela Choroidea) and attached Choroid Plexus roofs the third ventricle. The inferior portion of the Diencephalon forms the floor of the third ventricle and is named the Hypothalamus in relation to the Thalamus, the largest part of the Diencephalon, which lies above it. In a normal patient, the third ventricle is located at the midline of the skull, at approximately the height of the temporal areas.

Projecting from the Hypothalamus (which forms the floor of the third ventricle) on a slender stalk, or Infundibulum, is the Hypophysis. The Hypothalamus and Hypophysis are closely related and regulate many important body functions, such as temperature, water and fat metabolism, sleep, sexual activity and emotional control. The Thalamus receives nearly all sensory impulses from the peripheral nervous system and relays them to the Cerebral Cortex.

The Mesencephalon (midbrain) is the smallest part of the Brain Stem, being about 2 cm in length. Its narrow cavity, the Cerebral Aqueduct connects the third and fourth ventricles. In the midbrain, the narrow cerebral aqueduct connects the third and fourth ventricles. The Choroid Plexus, which roofs the third ventricle, produces cerebrospinal fluid, which is a clear watery fluid that both supports the brain and provides its extracellular fluid.

The fourth ventricle is located between the Pons, Cerebellum and Medulla. It communicates with the Cerebral Aqueduct, the central canal of the spinal cord and the subarachnoid space which surrounds the central nervous system. The roof of the fourth ventricle caudal to the Cerebellum, the Tela Choroidea, is thin like that of the third ventricle and has a Choroid Plexus. It is perforated by a small median aperture and two lateral apertures that allow cerebrospinal fluid to exit the ventricular system and bathe the brain and spinal cord.

Cerebrospinal fluid is a watery, alkaline fluid, similar in constitution to blood plasma. It is elaborated by or through the Choroid Plexuses of the lateral, the third and the fourth ventricles of the brain. It occupies the intercommunicating ventricles and, being constantly formed, is drained from the ventricles by minute Foramina in the roof of the fourth ventricle. These are the median and lateral apertures of the fourth ventricle, the latter pair being located at the extremities of the lateral recesses of the ventricle. Small additions to the cerebrospinal fluid are made through the perivascular channels of the brain surface and by the Ependyma of the central canal of the spinal cord. The total volume of the fluid is from 130 to 150 cc. Emerging through the Foramina into the subarachnoid space, the cerebrospinal spinal fluid bathes the surface of the brain and spinal cord, providing a fluid suspension and a valuable shock absorber around these organs of the nervous system. The fluid has a pressure of about 100 mm of water, which is intermediate between that of the peripheral arterial and venous sinus pressure.

Cerebrospinal fluid readily passes through the thinned out membrane of the arachnoidal granulations and the Endothelial lining of the Dural sinuses and joins the venous blood of the sinus. A smaller part of the fluid is returned to the vascular system by way of the lymphatics of the cranial nerves and via ependima of ventricles.

The Cerebral Peduncles are prominent fiber bundles connecting centers above and below the Mesencephalon (the mid-brain). Dorsally, two superior and two inferior Colliculi, collectively referred to as Corpora Quadrigemina, are found. These are relay centers in the optic and auditory systems, respectively.

Caudal to the Mesencephalon lie the Pons ventrally and the Cerebellum dorsally, with the fourth ventricle situated between them. The Pons consists superficially of large transverse fiber bundles which connect the two Cerebellar hemispheres. Deep within the Pons lie longitudinal fiber bundles, which carry impulses up and down the brain stem, and scattered nuclei.

The lowest part of the brain stem, below the Pons, is the Medulla Oblongata. It is continuous with the spinal cord just above the first cervical spinal nerve, but the boundary is indistinguishable. Structures contained in the Medulla extend into the spinal cord, and the Medulla transmits all fibers connecting brain and spinal cord. Lying in the Medulla are centers regulating important functions such as the respiratory center, cardiac center, vasomotor center, and centers for swallowing, gastric secretion and sweating.

In contrast to the Cerebrum, the Cerebellum is a solid mass of tissue. Like the Cerebrum, it is covered by a layer of gray matter, the Cortex, overlaying white matter and the surface is thrown into a series of parallel folds, here called Folia. It has two hemispheres, a midline vermis and several nuclei internally. Three sets of Peduncles, lying superior, lateral and inferior to the fourth ventricle, connect the Cerebellum to the Mesencephalon, Pons and Medulla Oblongata. The Cerebellum is a coordination center for muscular activity, particularly walking. It is the only part of the central nervous system that does not give rise to peripheral nerves.

Measurement of ICP

FIG. 1 shows a standard prior art device for invasively measuring intra cranial pressure (ICP). A hole is drilled in the skull of the patient as shown. A catheter is then inserted through the skull and directed in the lateral plane towards the external auditory meatus and in the AP plane towards the inner canthus to a depth of approximately 7 cm below the scalp. The catheter is filled with saline, and is coupled to a pressure transducer, which, in turn, is coupled to a chart recorder. This procedure provides an accurate measurement of the ICP at the lateral ventricle of a patient, but has the disadvantage of being traumatic to the patient.

Figure 2A:
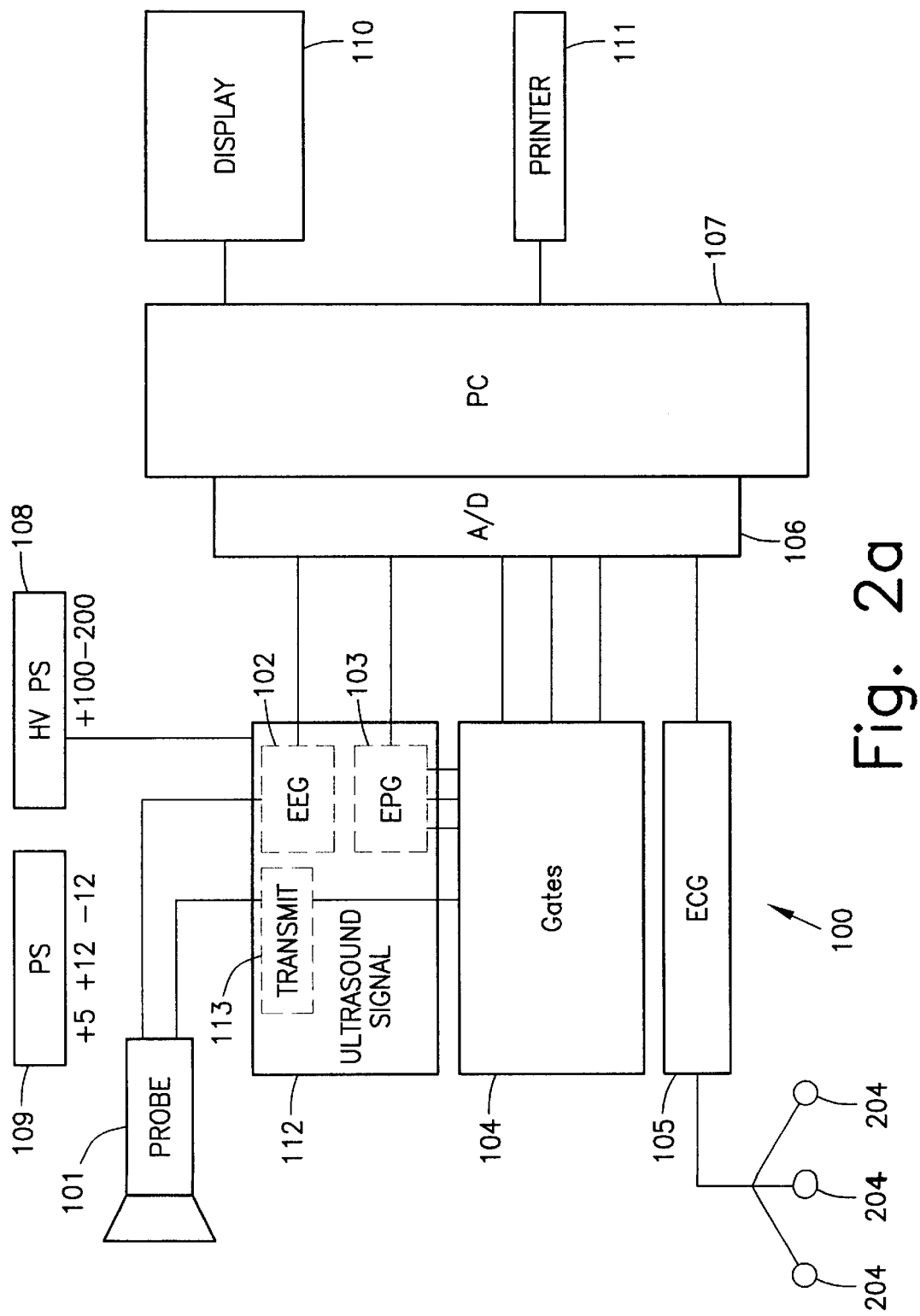
FIG. 2(a) is a block diagram of a preferred apparatus for transmitting and receiving ultrasound waves, and generating EPG, Echo EG, and ECG waveforms.

In accordance with the present invention, a non-invasive system is provided which accurately measures ICP, as well as a number of additional parameters and conditions. FIG. 2(a) is a block diagram of a preferred apparatus 100 in accordance with the present invention for transmitting and receiving ultrasound waves, and generating Echo Encephalogram (Echo EG), Electrocardiogram (ECG), and Echopulsogram (EPG) waveforms. The apparatus 100 includes an ultrasound probe 101, a computer 107, an Analog to Digital (AID) converter 106, an ultrasound signal controller and processor 112, a gating circuit 104, and a Electrocardiograph 105 with corresponding electrodes 204. The apparatus also includes a suitable low-voltage power supply 109 to provide power to these circuits and a high-voltage power supply 108 to supply the Ultrasound Transmitter 113 which drives the probe 101. A display terminal 110 and printer 111 are also illustrated. The apparatus 100 may, for example, comprise the apparatus described in U.S. Pat. No. 5,840,018, described above, and incorporated herein by reference.

The ultrasound probe 101 is held in contact with the skull of a patient. Preferably, the probe 101 is held in contact with the forehead of the patient for measurement of ICP at the third ventricle. Most preferably, the probe 101 is placed 2–6 cm above the bridge of the nose of a patient. The probe 101 serves as both a transmitter and receiver of ultrasound waves. The ECG probes 204 are secured to the patient in a conventional manner in order to generate a conventional ECG signal. If desired, a respiratory wave signal can also be generated by demodulating the EPG waveform, with the carrier signal providing a representation of the respiratory wave.

The apparatus 100 generates a pulse signal having a constant pulse width and constant power to produce an EPG and Echo EG waveform. However, the pulse width and power will be adjusted to determine a suitable constant power and wavelength for each patient. Preferably, the pulse width is initially varied from 100 ns to 1000 ns to determine the proper pulse width for monitoring a structure of interest in the brain for a particular patient. The power can vary from 50 mW/cm$^2$ to 300 mW/cm$^2$.

Figure 3:
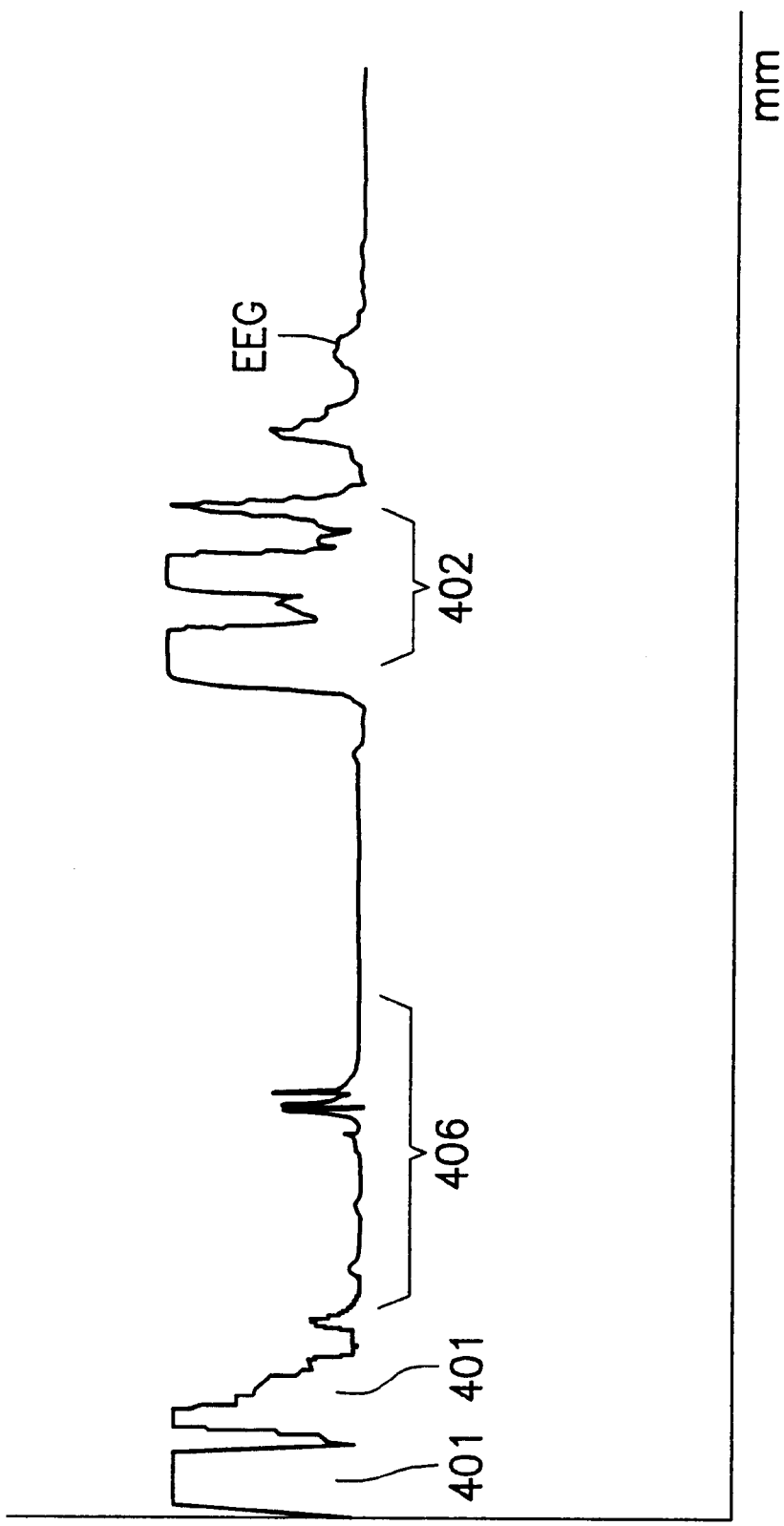
FIG. 3 is a plot of a representative Echo EG waveform.

FIG. 3 is a plot of an Echo EG signal received by the probe 101 in response to a transmitted pulse, and digitized and displayed, for example, on display screen 110 as a function of distance from the probe 101. In this regard, the distance ordinate is obtained by converting the time delay from transmission of the ultrasound pulse to receipt of the reflected signals to the distance from the ultrasound probe to the point of reflection based upon a typical speed of propagation of an ultrasound signal through skull and brain tissue. The various portions of the reflected waveforms can be identified with various structures in the brain and skull which lie in a path perpendicular to the probe 101. For example, referring to FIG. 3, the peaks identified as 401 in FIG. 3 correspond to waves reflected from the front portion of the skull, the peaks identified as 402 in FIG. 3 correspond to waves reflected from the rear portion of the skull, and the reflections 406 correspond to waves reflected from the interior soft tissue in the brain. Therefore, by estimating the distance from the probe to a site of interest in the brain (e.g., the third ventricle), it is possible to estimate which of the soft tissue reflections are reflections from the site of interest. A gating circuit, such as the gating circuit 104 described in U.S. Pat. No. 5,840,018 (described above), can then be used to examine a small portion of the Echo EG reflected signal. In a preferred embodiment of the invention, the gating circuit gates a 0.3 to 1.3 µs portion of the waveform. Preferably, the gating circuit gates a 0.3 to 1 µs portion, and most preferably, a 0.5 to 0.7 µs portion of the waveform (corresponding to approximately one pixel and a depth of resolution of 0.5 mm).

Figure 4:
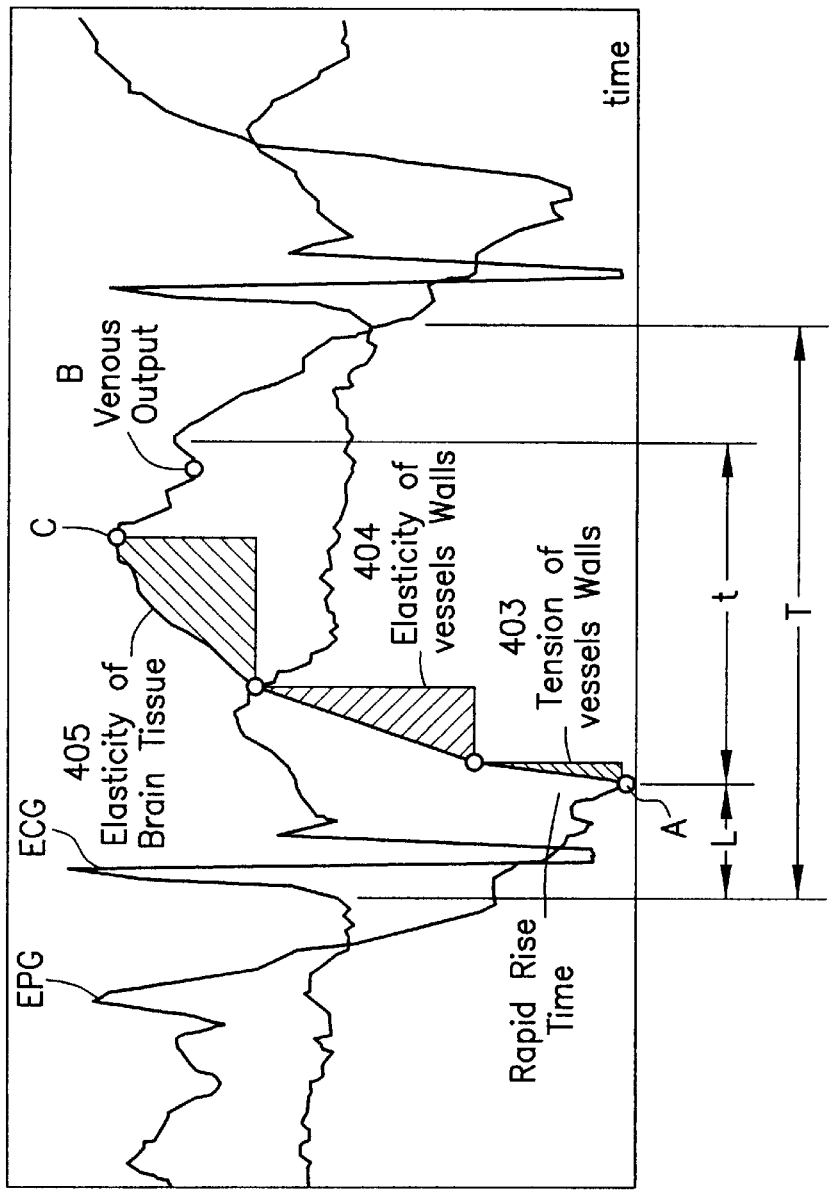
FIG. 4 is an illustration of how the pulsatility characteristics of the brain can be identified in an EPG waveform.

FIG. 4 is a plot of an EPG waveform which is derived from a corresponding Echo EG signal (not shown) and an ECG waveform generated from the ECG electrodes. In this regard, EPG is defined as the integral of the Echo EG waveform across the gated portion of the Echo EG waveform:

$$EPG = \int Echo\ EG(t),$$

wherein t is extends from g1 to g2, and wherein g1 is the starting point of the gate and g2 is the endpoint of the gate. As set forth above, the width of the gate (g2–g1) is approximately 0.5–0.7 us. The ECG waveform is used to identify the cardiac systole (i.e. contraction of the heart), and provides a reference point for interpreting the EPG waveform. Referring to FIG. 4, a corresponding peak in the EPG waveform following a cardiac systole can be divided into a number of regions of interest. A first, initial portion 403 of the EPG peak, extends from the beginning of brain (e.g. cerebral) pulsatility (point "A") following the cardiac systole and exhibits a rapid rise time, provides an indication of the tension of the vessel walls. The beginning of brain pulsatility (A) can be estimated as the minimum of the EPG waveform following the cardiac systole. The end of the first portion 403 is defined as the maximum df/dt of the EPG waveform. The first portion 403 corresponds to the time period in which blood flow from the preceding cardiac systole has reached the blood vessels at the site of interest, but has not yet caused the blood vessels to expand significantly. Therefore, the longer the duration in time of the first portion 403, the less tension there is in the blood vessels.

The next, second portion 404 of the EPG waveform, which extends from the end of the first portion to the maximum of $(-d^2f/d^2t)$, provides an indication of the elasticity of the vessel walls. In this regard, the greater the time from Max (df/dt) to Max $(-d^2f/d^2t)$, the greater the elasticity of the vessel walls. The next, third portion 405 of the EPG waveform, which extends from the end of the second portion 404 to the absolute maximum of f(t) (point C), provides an indication of the elasticity of the brain tissue. In this regard, the greater the time to the peak in the waveform, the greater the elasticity of the brain tissue. Finally, a venous output notch (point "B"), which is characterized by a notch in the waveform between the peak and a subsequent cardiac systole, identifies a point in time at which the flow of blood through the brain tissue at the gated location is primarily exiting the brain tissue.

In accordance with one embodiment of the present invention, the EPG waveform is used to provide a quantitative indication of intra cranial pressure (ICP). In this regard, ICP is defined as follows:

For $\rho = \rho_1, \rho_2,$ or $\rho_3$ $$ICP_{maximum} = \rho(t_1/T)^*[t_1/T] - \beta$$

$$ICP_{minimum} = \rho(t_2/T)^*[t_2/T] - \beta$$

For $\rho = \rho_0$ $$ICP_{maximum} = \rho(t_1/T)^*[t_1/T]$$

$$ICP_{minimum} = \rho(t_2/T)^*[t_2/T]$$

wherein T is the time period between cardiac systoles, $t_1$ is the time from the beginning of brain (e.g. cerebral) pulsatility (point "A") to the peak (point "C") following the venous notch (point "B"), $t_2$ is the time from the beginning of brain pulsatility (point "A") to a first point following the peak ("C") which has the same amplitude as the venous notch (point "B"), $\beta$ is a constant having a value of 9 mm $H_2O$, and $\rho(t/T)$, where t is $t_1$ or $t_2$, is a function which is characteristic of the particular brain tissue being monitored.

Figure 5:
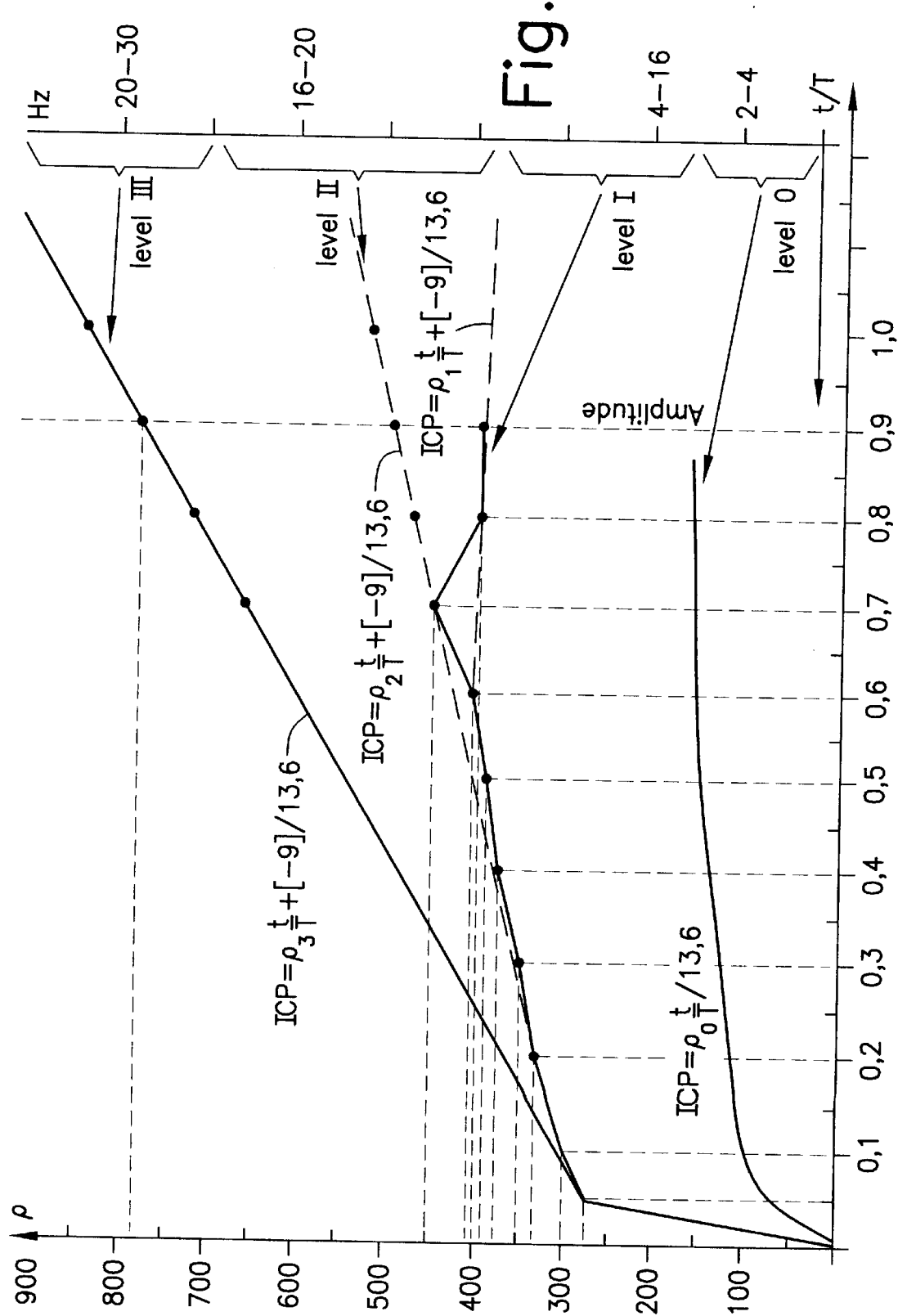
FIG. 5 is a graph of the variable p as a function of t/T, and as a function of different frequencies of the second resonant frequency of the EPG waveform.

FIG. 5 is a plot of $\rho$ for $p_0$, $p_1$, $p_2$, or $p_3$ as a function of t/T. In this regard, $\rho_0$ is used as the value for $\rho$ when the second resonance frequency of EPG waveform is less than 4 Hz, $\rho_1$ is used as the value for $\rho$ when the second resonance frequency of EPG waveform is between 4 Hz and 16 Hz, $\rho_2$ is used as the value for $\rho$ when the second resonance frequency of EPG waveform is between 16 Hz and 20 Hz, and $\rho_3$ is used as the value for $\rho$ when the second resonance frequency of EPG waveform is greater than 20 Hz. Preferably, the second resonance frequency is identified by performing a discrete fourier transform (DFT) of the EPG signal across one cardiac systole. These plots of $\rho$ can be used to calculate ICP for the third ventricle of the brain, the central cerebral vein, the suprasellar cistern, and lateral ventricle trigon. In addition, function $\rho(t/T)$ shown in FIG. 5 can be used in to calculate the ICP in other regions of the brain, provided that an EPG waveform having the characteristics of FIG. 4 (i.e., portions 403, 404, 405 and point B) can be identified. As an example, it has been found that the function $\rho(t/T)$ can not always be used to calculate ICP in the superior sagittal sinus or the inferior sagittal sinus.

In this regard, it should be apparent that the values for $\rho$ could be calculated automatically by the computer 107 of FIG. 2(a) using for example, a look-up table, and that the value of T could be readily determined by the computer 107 based upon the ECG signal plot. The value for t could be entered manually by a technician, for example, by "clicking" on the appropriate portion of the EPG waveform using a computer mouse, or automatically by the computer 107.

Figure 2B:
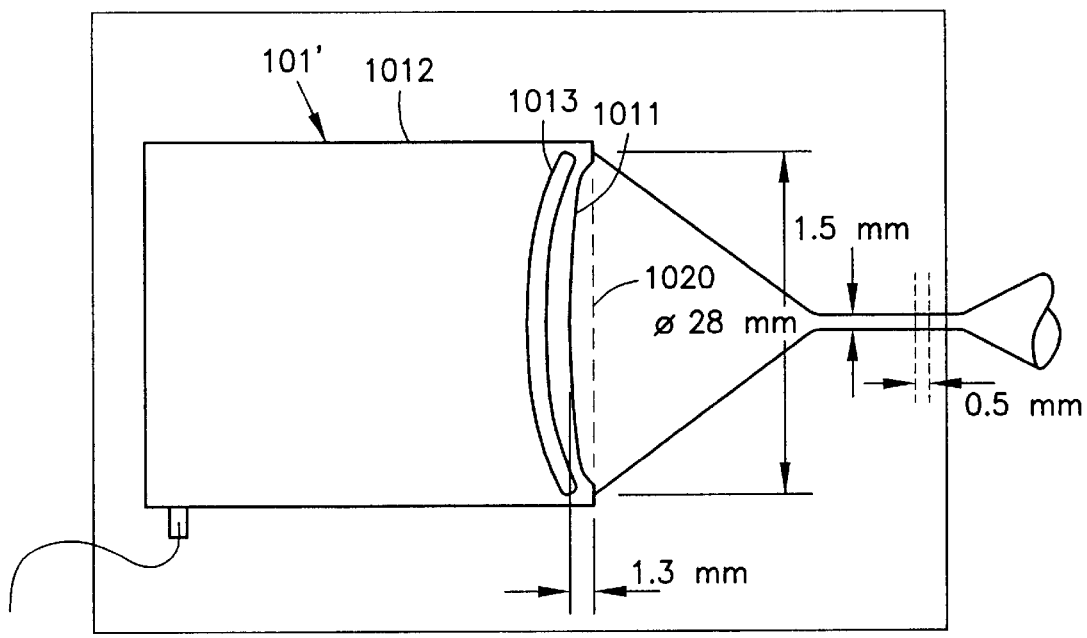
FIG. 2(b) illustrates a preferred ultrasonic probe which may be used in conjunction with the apparatus of FIG. 2(a).

FIG. 2(b) shows a concave probe 101' which is preferably used as the probe 101 in the apparatus of FIG. 2(a). The concave probe 101' focuses the transmitted ultrasound signal on an area of approximately 0.5×1.5 mm (0.75 mm$^2$). The probe 101' includes a concave transmitting/receiving surface 1011, a piezoelectric transducer 1013, and a dampening material 1012 disposed adjacent thereto. The diameter across the surface 1010 is 28 mm, and the surface 1010 has a circular concave shape which extends to a depth of 1.3 mm perpendicularly from an imaginary plane 1020 extending across the face of the surface 1010. Preferably, the piezoelectric transducer 1013 oscillates around a principal frequency of between 0.8 and 1.2 MHz, and most preferably around a principal self-frequency of about 1.0 MHz. The pulse width of ultrasound signal transmitted by the probe 101' can be varied between 100 ns to 1000 ns as described above. The trigger pulse repetition frequency is preferably at least about 3 KHz. The general nature of the transmitted waveform is illustrated in FIG. 2b. In combination with the gating feature described above, the concave probe 1011' allows the apparatus in accordance with the present invention to provide an analysis of a portion of the brain with an area of 0.75 mm$^2$ and a depth of 0.5 mm as illustrated in FIG. 2a.

Figure 6A:
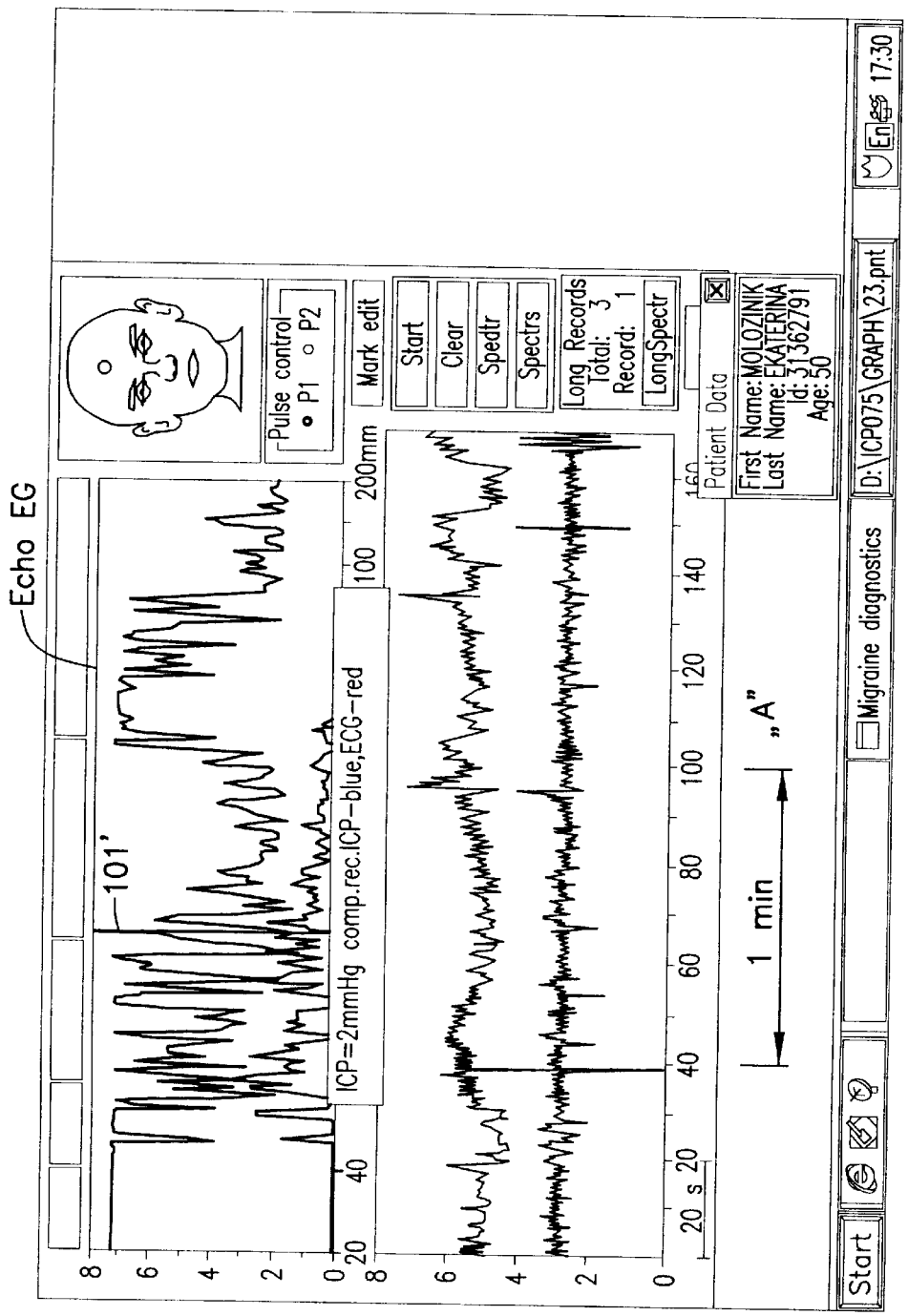
FIG. 6a is a plot of an Echo EG waveform for the third ventricle which was received from the ultrasound probe of FIG. 2 in response to a single ultrasound pulse generated from the ultrasound probe.

FIG. 6(a) shows an Echo EG waveform for a patient generated with a concave probe 101'. The Echo EG waveform shows the waves reflected from the skull and brain of the patient in an area of 0.75 mm$^2$ extending perpendicularly from the probe 101' through the front skull and brain tissue to the back skull of the patient. The Echo EG signal has been gated at 97 mm (as indicated by the vertical line in FIG. 6(a)

at 97 mm), which corresponds to the location of the third ventricle of the patient. Therefore, the gated portion of the Echo EG signal corresponds to a portion of the brain of the patient at a depth of approximately 97 mm, which has an area of 0.75 mm$^2$ and a depth of approximately 0.1 mm. As indicated in the text box between the upper and lower graphs, the ICP for this patient, measured invasively using the device and method of FIG. 1, was 2 mm Hg.

Figure 6B:
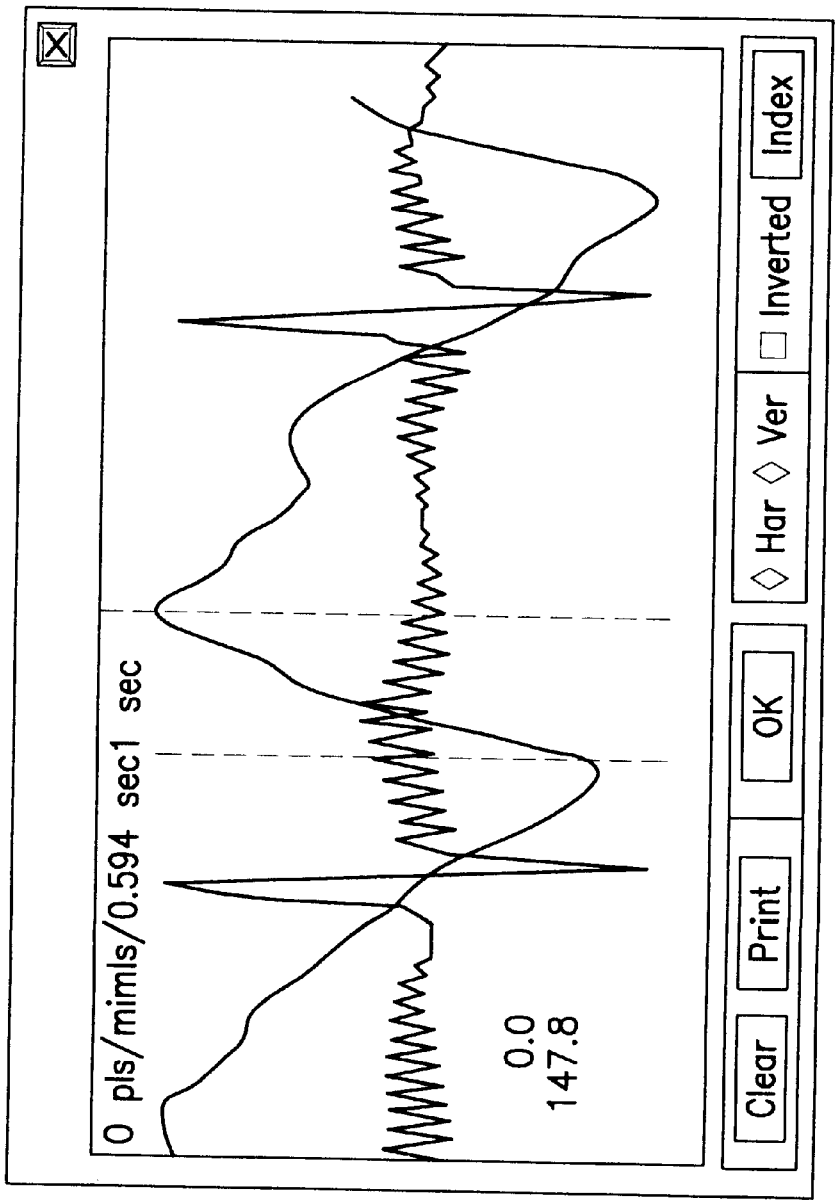
FIG. 6b is a plot of an EPG waveform generated from the plot of FIG. 6a, along with a corresponding ECG waveform generated by the apparatus of FIG. 2(a).
Figure 6C:
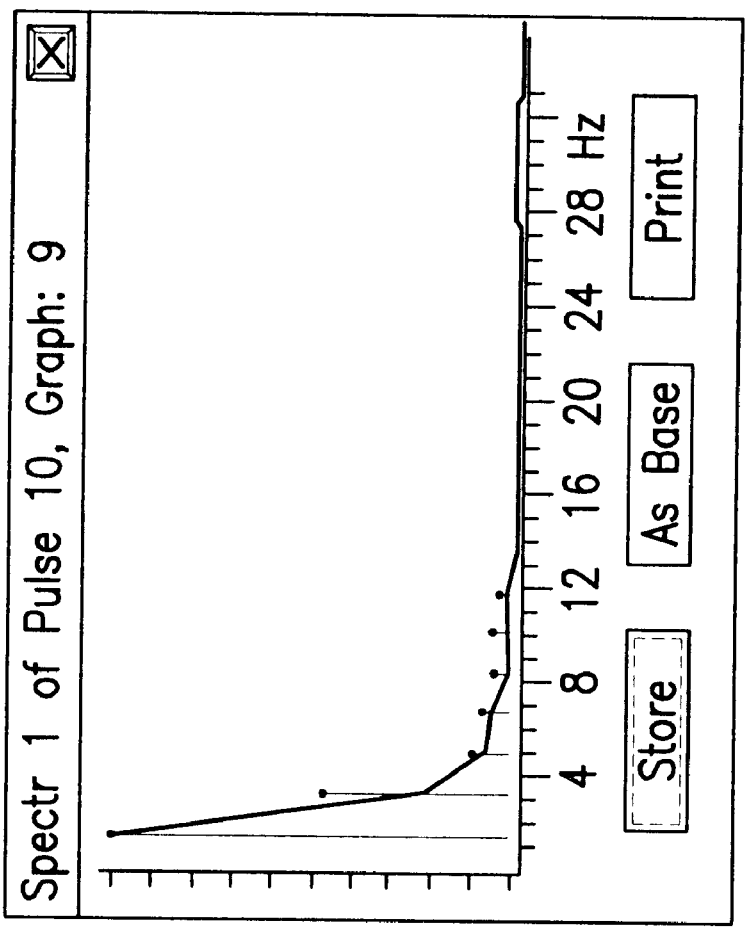
FIG. 6c is a plot of the Discrete Fourier Transform of the waveform of FIG. 6b.

FIG. 6b shows the corresponding EPG waveform (generated by integrating the Echo EG waveform across the gate interval) and ECG waveform for the patient, plotted as a function of time. The waveform is shown for one cardiac cycle with T=597 msec and t=147 msec, and t/T=147/597=0.24. FIG. 6c shows a Discrete Fourier Transform of the EPG signal over the cardiac cycle. Referring to FIG. 6c, it is apparent that only the first resonance frequency (at 2 Hz) is visible. As there is no second resonance frequency, the equation for $\rho=\rho_0$ is used (because the second resonance frequency is less than 4 Hz). Applying the value $\rho=\rho_0=120$ from FIG. 5 into the equation for ICP for $\rho=\rho_0$, we have ICP=$\rho$(t/T)*[t/T]=120*0.24=28.8 mm H$_2$O or 2.11 mm Hg, which correlates well with the invasively measured ICP value of 2 mm Hg.

Figure 7A:
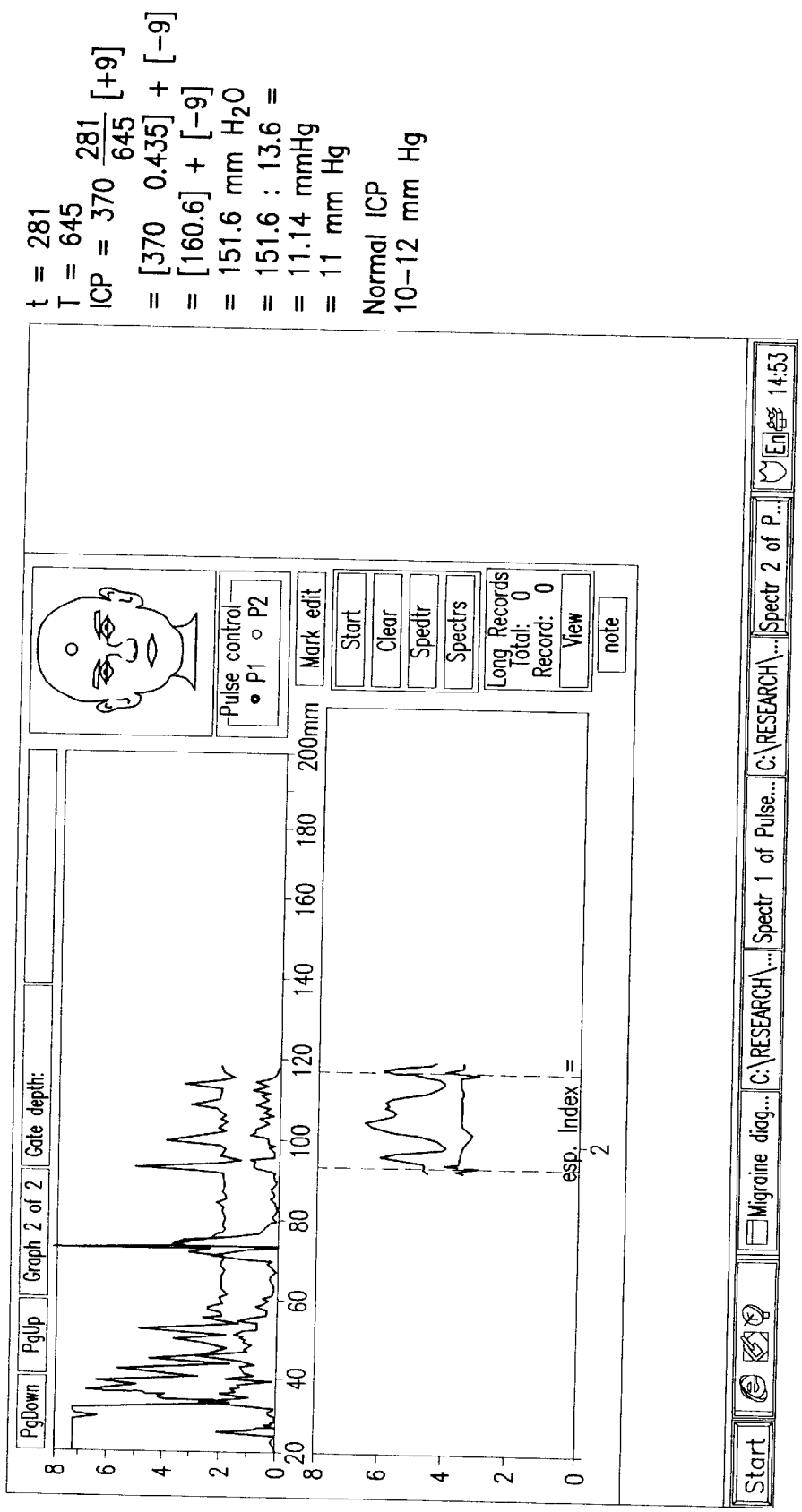
FIG. 7a is a plot of a reflectance (Echo EG) waveform for the third ventricle which was received from the ultrasound probe of FIG. 2 in response to a single ultrasound pulse generated from the ultrasound probe.

FIG. 7a shows an Echo EG waveform for a patient with normal ICP which was generated with a concave probe 101'. The Echo EG waveform shows the waves reflected from the skull and brain of the patient in an area of 0.75 mm$^2$ extending perpendicularly from the probe 101' through the front skull and brain tissue to the back skull of the patient. The Echo EG signal has been gated at about 71 mm (as indicated by the vertical line in FIG. 6(a) at about 71 mm), which corresponds to the location of the third ventricle of the patient. Therefore, the gated portion of the Echo EG signal corresponds to a portion of the brain of the patient at a depth of approximately 71 mm, which has an area of 0.75 mm$^2$ and a depth of approximately 0.1 mm. The ICP for this patient, measured invasively using the device and method of FIG. 1, was between 10 and 12 mm Hg.

Figure 7B:
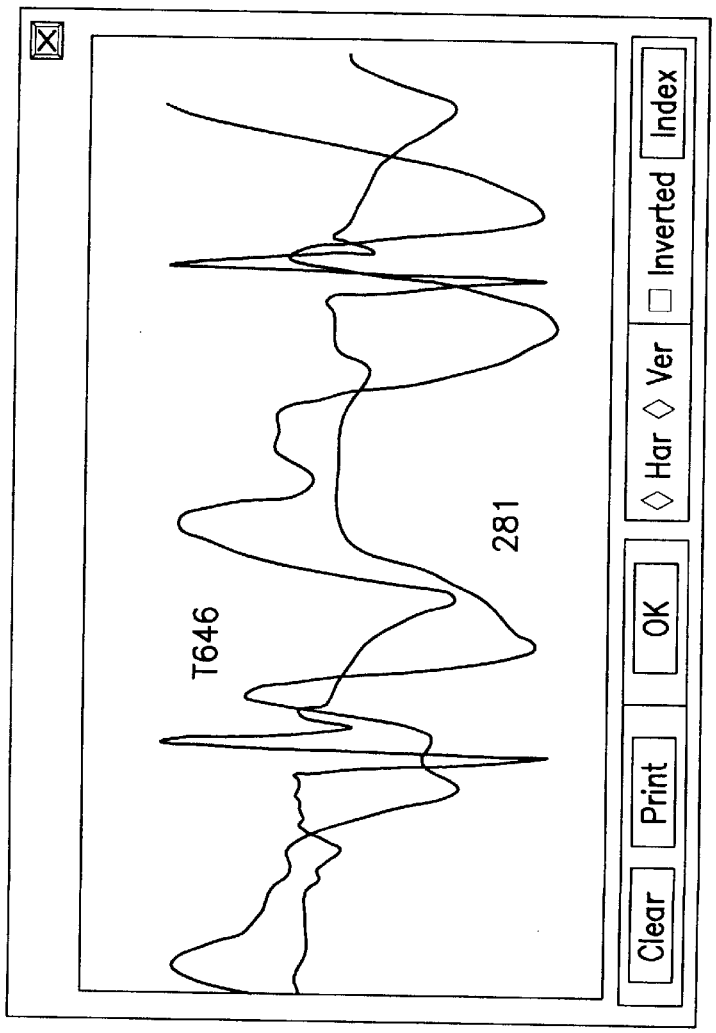
FIG. 7b is a plot of an EPG waveform generated from the plot of FIG. 7a, along with a corresponding ECG waveform generated by the apparatus of FIG. 2(a).
Figure 7C:
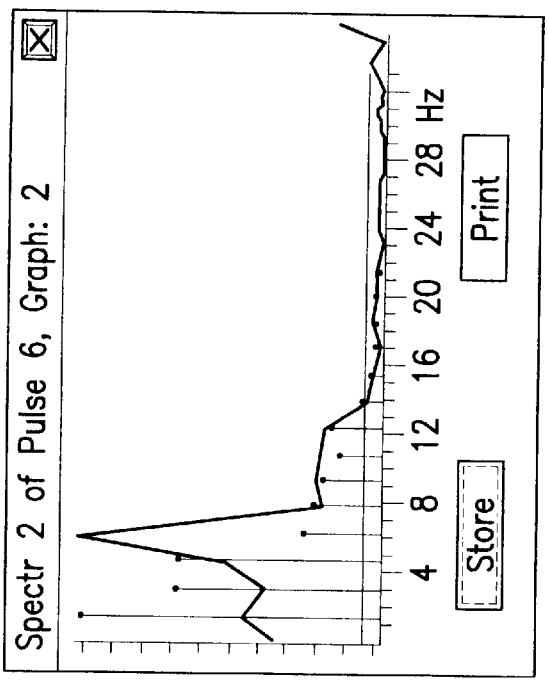
FIG. 7c is a plot of the Discrete Fourier Transform of the waveform of FIG. 7b.

FIG. 7b shows the corresponding EPG waveform (generated by integrating the Echo EG waveform across the gate interval) and ECG waveform for the patient, plotted as a function of time. The waveform is shown for one cardiac cycle with T=645 msec and t=281 msec, and t/T=281/645=0.435. FIG. 7c shows a Discrete Fourier Transform of the EPG signal over the cardiac cycle. Referring to FIG. 6c, it is apparent that the second resonance frequency is at about 6 Hz (with the first resonance frequency at about 1.5 Hz). Therefore, as the second resonance frequency is between 4 and 16 Hz, the equation for $\rho=\rho_1$ is used. Applying the value $\rho=\rho_1=370$ from FIG. 5 into the equation for ICP for $\rho=\rho_1$, we have ICP=$\rho$(t/T)*[t/T]−9=370*0.435−9=151.6 mm H$_2$O or 11.14 mm Hg, which correlates well with the invasively measured ICP value of 10–12 mm Hg.

Figure 8A:
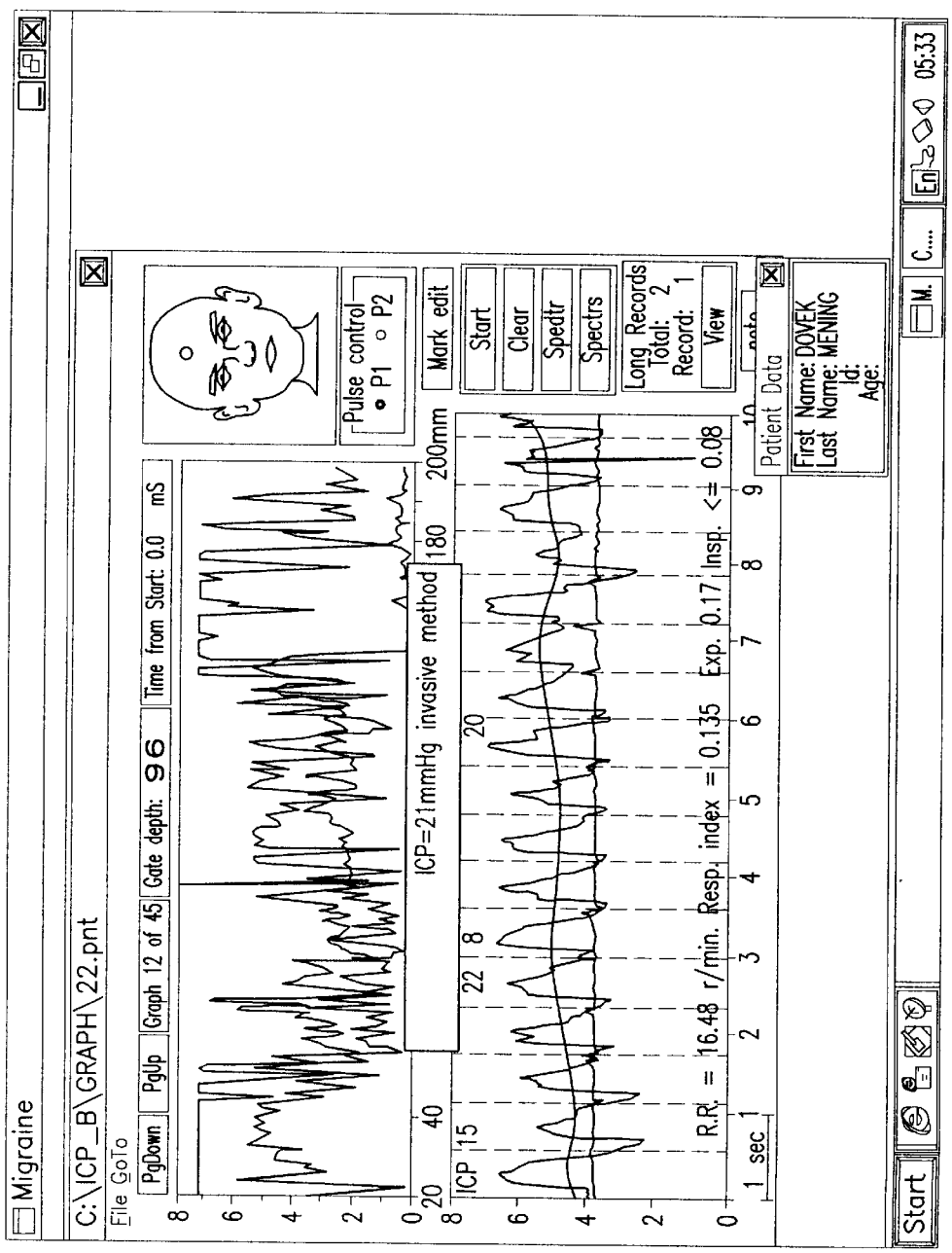
FIG. 8a is a plot of a reflectance (Echo EG) waveform for the third ventricle which was received from the ultrasound probe of FIG. 2 in response to a single ultrasound pulse generated from the ultrasound probe, and a corresponding plot of an EPG waveform, ECG waveform, and respiratory wave.

FIG. 8a shows an Echo EG waveform (upper plot) for a patient with moderately high ICP which was generated with a concave probe 101'. The Echo EG waveform shows the waves reflected from the skull and brain of the patient in an area of 0.75 mm$^2$ extending perpendicularly from the probe 101' through the front skull and brain tissue to the back skull of the patient. The Echo EG signal has been gated at about 96 mm (as indicated by the vertical line in FIG. 8(a) at about 96 mm), which corresponds to the location of the third ventricle of the patient. Therefore, the gated portion of the Echo EG signal corresponds to a portion of the brain of the patient at a depth of approximately 96 mm, which has an area of 0.75 mm$^2$ and a depth of approximately 0.1 mm. As indicated in the text box between the upper and lower graphs, the ICP for this patient, measured invasively using the device and method of FIG. 1, was 21 mm Hg.

The lower plot of FIG. 8(a) shows the corresponding EPG and ECG waveforms, along with a plot of the patient's respiratory wave. The respiratory wave can be obtained from the EPG waveform by plotting the successive point A's (or successive point C's) of FIG. 4 or via conventional demodulation techniques. The respiratory wave provides an indication of the modulation of the EPG signal which is caused by the patient's respiration. In evaluating the EPG signal, it is important to take this modulation into consideration.

Figure 8B:
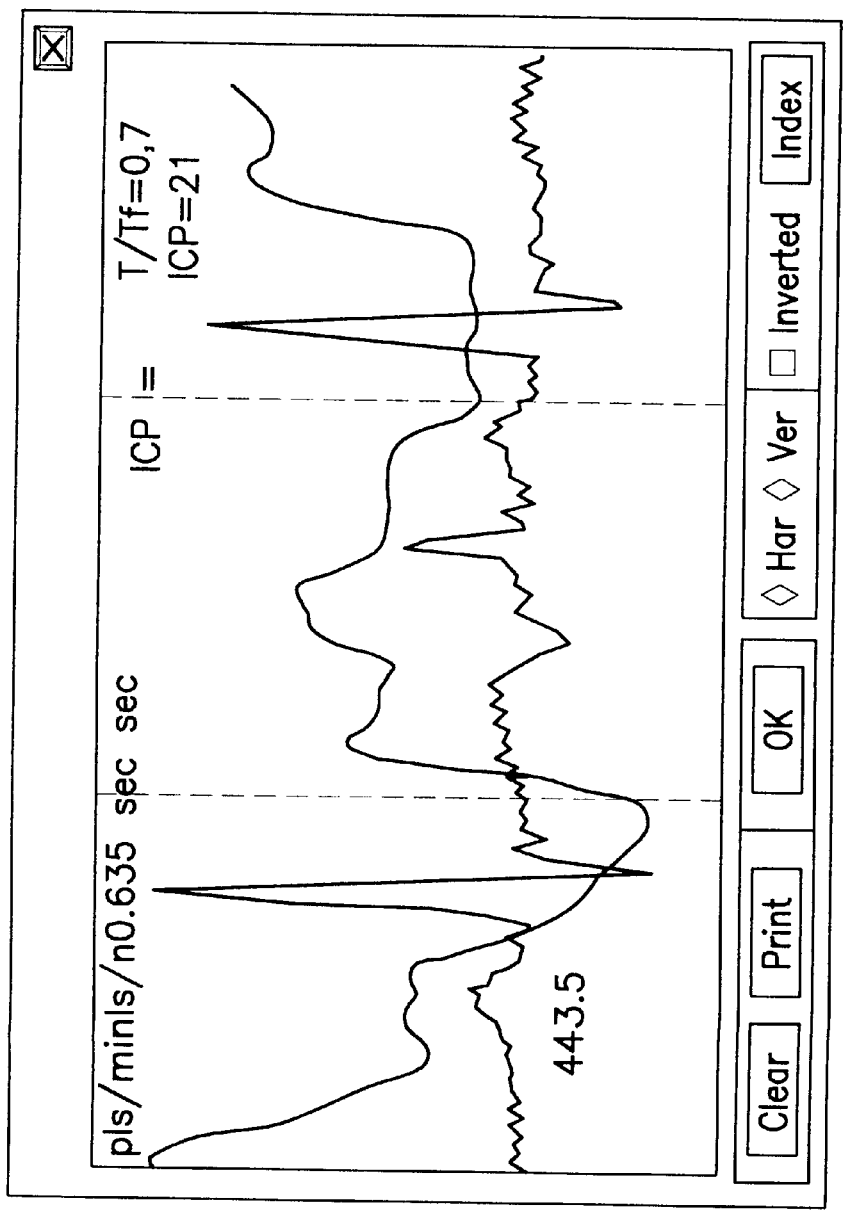
FIG. 8b is a magnified plot of an EPG waveform generated from the plot of FIG. 8a, along with the corresponding ECG waveform generated by the apparatus of FIG. 2(a).
Figure 8C:
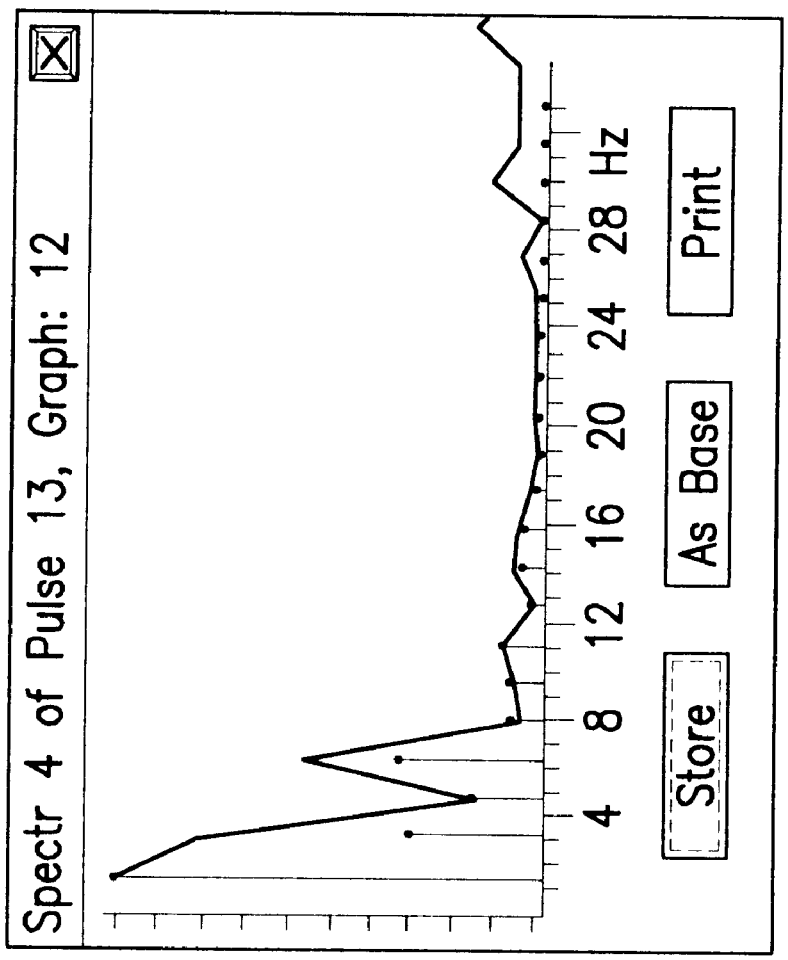
FIG. 8c is a plot of the Discrete Fourier Transform (DFT) of the waveform of FIG. 8b.

FIG. 8b shows a magnified view of the EPG waveform of FIG. 8(a) (generated by integrating the Echo EG waveform across the gate interval) and ECG waveform for the patient, plotted as a function of time. The waveform is shown for one cardiac cycle with T=635 msec and t=443.5 msec, and t/T=443.5/635=0.7. FIG. 8c shows a Discrete Fourier Transform of the EPG signal over the cardiac cycle. Referring to FIG. 8c, it is apparent that the second resonance frequency is at about 6 Hz (with the first resonance frequency at about 3 Hz). Therefore, as the second resonance frequency is between 4 and 16 Hz, the equation for $\rho=\rho_1$ is used. Applying the value $\rho=\rho_0=425$ from FIG. 5 into the equation for ICP for $\rho=\rho_1$, we have ICP=$\rho$(t/T)*[t/T]=425*0.7−9=287.5 mm H$_2$O or 21.14 mm Hg. Once again, the noninvasively measured value correlates well with the invasively measured ICP value of 21 mm Hg.

Figure 9A:
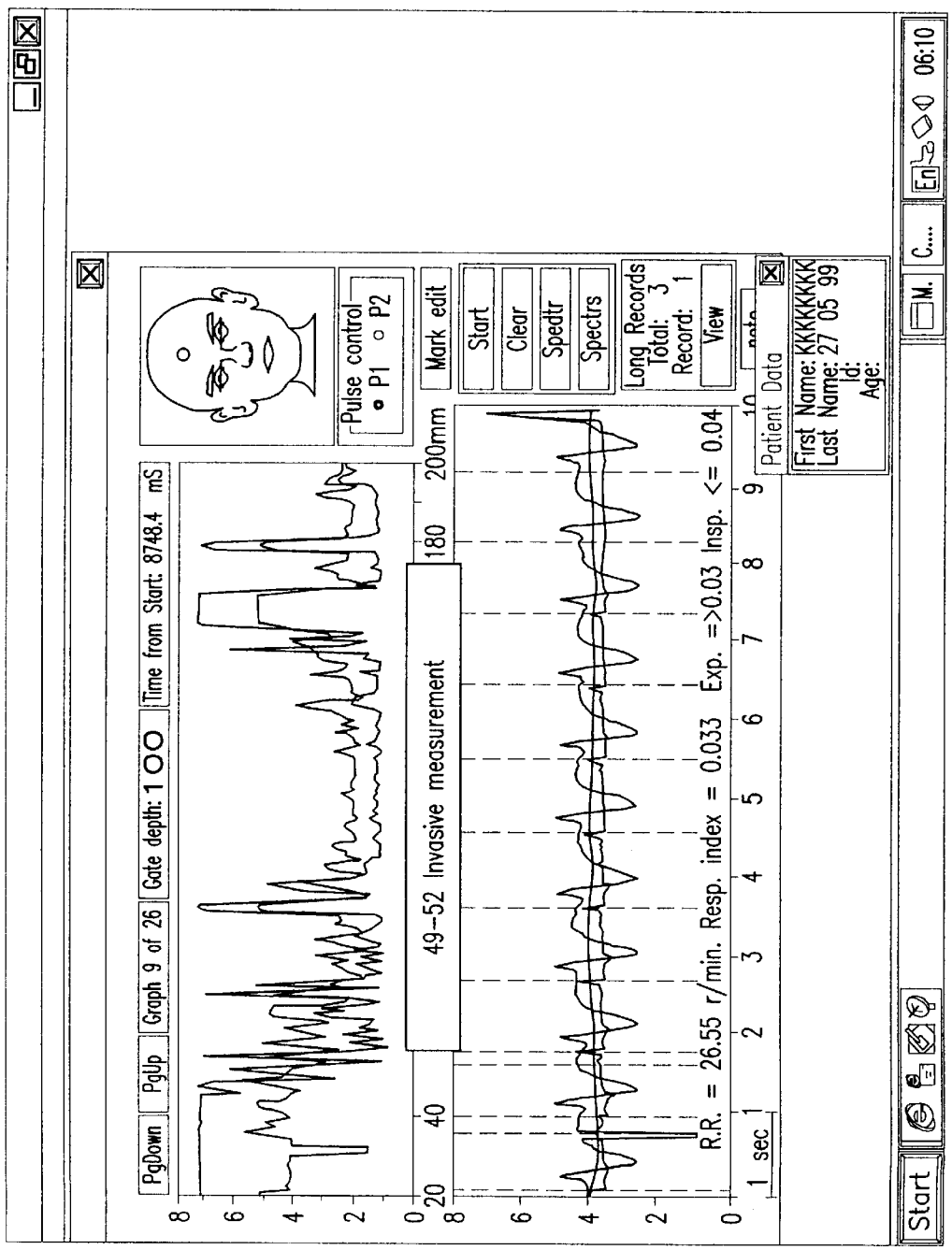
FIG. 9a is a plot of a reflectance (Echo EG) waveform which was received from the ultrasound probe of FIG. 2 in response to a single ultrasound pulse generated from the ultrasound probe, with a gate depth of 100 mm, and a corresponding plot of an EPG waveform, ECG waveform, and respiratory wave.

FIG. 9a shows an Echo EG waveform (upper plot) for a patient with high ICP which was generated with a concave probe 101', along with the corresponding EPG, ECG, and respiratory waveforms (lower plot) for the patient. The Echo EG waveform shows the waves reflected from the skull and brain of the patient in an area of 0.75 mm$^2$ extending perpendicularly from the probe 101' through the front skull and brain tissue to the back skull of the patient. The Echo EG signal has been gated at 100 mm (as indicated by the vertical line in FIG. 11(a) at 100 mm), which corresponds to the location of the third ventricle of the patient. Therefore, the gated portion of the Echo EG signal corresponds to a portion of the brain of the patient at a depth of approximately 100 mm, which has an area of 0.75 mm$^2$ and a depth of approximately 0.1 mm. As indicated in the text box between the upper and lower graphs, the ICP for this patient, measured invasively using the device and method of FIG. 1, was between 49 and 52 mm Hg.

Figure 9B:
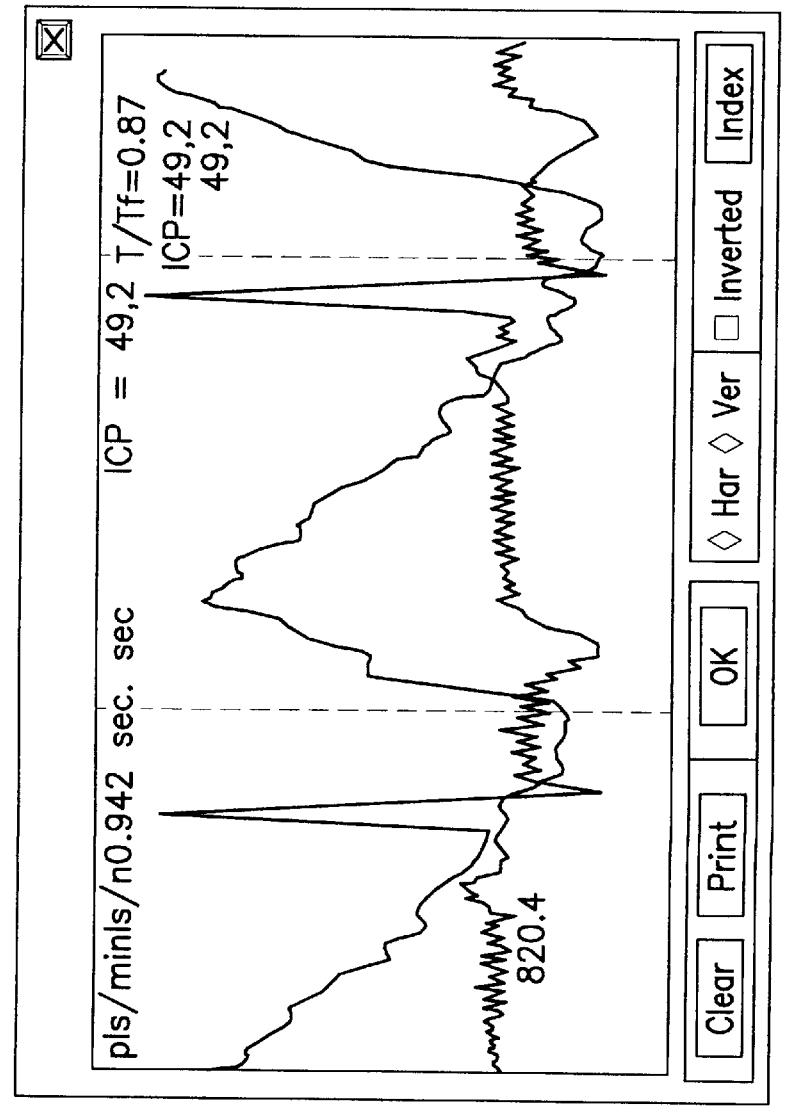
FIG. 9b is a magnified plot of an EPG waveform generated from the plot of FIG. 9a, along with a corresponding ECG waveform generated by the apparatus of FIG. 2(a).
Figure 9C:
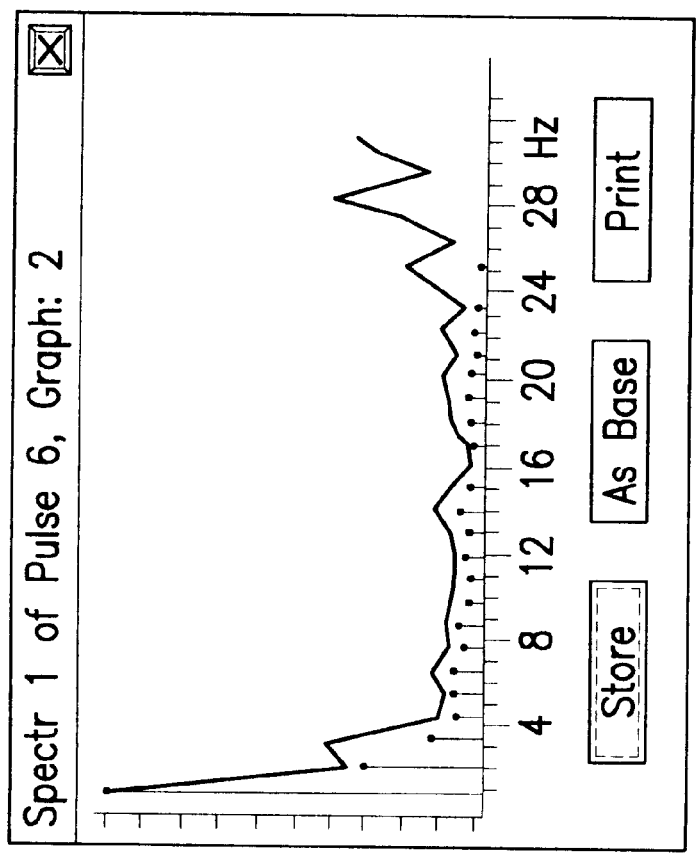
FIG. 9c is a plot of DFT of the waveform of FIG. 9b.

FIG. 9b shows a magnified view of the EPG waveform of FIG. 9(a) and ECG waveform for the patient, plotted as a function of time. The waveform is shown for one cardiac cycle with T=942 msec and t=820 msec, and t/T=820/942=0.87. FIG. 9c shows a Discrete Fourier Transform of the EPG signal over the cardiac cycle. Referring to FIG. 9c, it is apparent that the second resonance frequency is at about 28 Hz (with the first resonance frequency at about 1 Hz). Therefore, as the second resonance frequency is over 20 Hz, the equation for $\rho=\rho_3$ is used. Applying the value $\rho=_3=780$ from FIG. 5 into the equation for ICP for $\rho=_3$, we have ICP=$\rho$(t/T)*[t/T]=780*0.87−9=669.6 mm H$_2$O or 49.2 mm Hg, which again correlates well with the invasively measured ICP value of 49–52 mm Hg.

A qualitative measure of ICP can also be obtained through the use of the device of FIG. 2(a) by analyzing a compressed EPG waveform. In this regard, a compressed EPG waveform can be in the form of: A-waves, which are indicative of low ICP (under 8 mm Hg); B-waves, which are indicative of normal ICP (8–12 mm Hg); C-waves, which are indicative of relatively high ICP (18–30 mm Hg), and D-waves which are indicative of high ICP (over 50 mm Hg). A-waves are defined as compressed ICP waves which exhibit about one peak per minute, B-waves are defined as compressed EPG waves which exhibit about 6–10 peaks per minute, C-waves are defined as compressed EPG waves which are a combination of substantially flat waves, and waves exhibiting about 18 peaks per minute, and D waves are defined as compressed EPG waves which exhibit about 1 peak every 15–20 minutes.

FIGS. 6(d), 10, 11, 12, and 13 each shows a compressed EPG waveform (generated by integrating the Echo EG waveform across the gate interval) and a compressed ECG waveform.

In FIG. 6d, which corresponds to the Echo EG waveform of FIG. 6(a), the compressed EPG waveform is in the form of "A-waves" because it exhibits peaks about once every minute, and is therefore indicative of an ICP under 8 mm Hg. As set forth above, the patient in FIG. 6(a) had an invasively measured ICP of 2 mm Hg.

Figure 10:
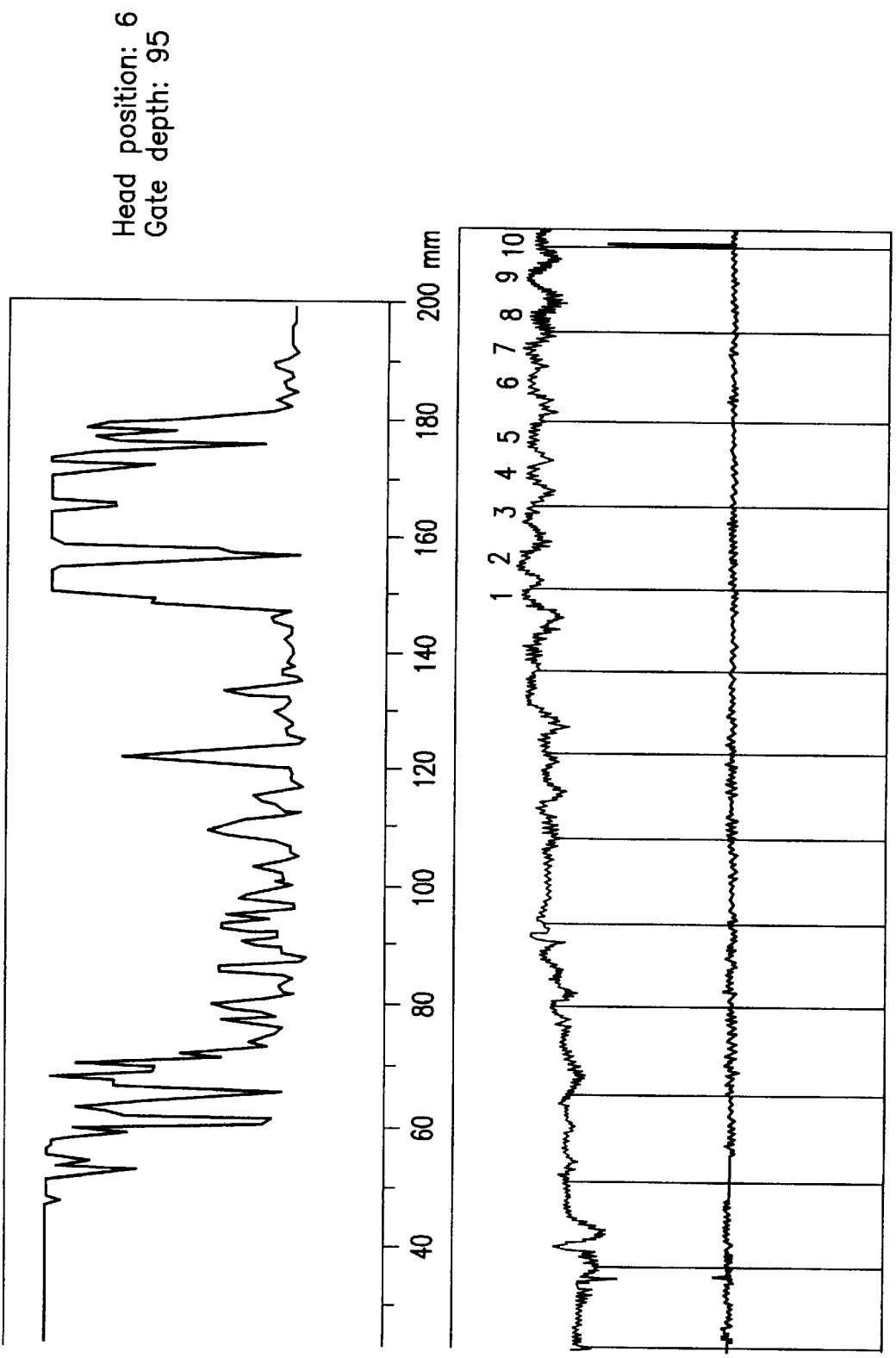
FIG. 10 is an Echo EG waveform and corresponding EPG waveform for a patient with normal ICP.
Figure 11:
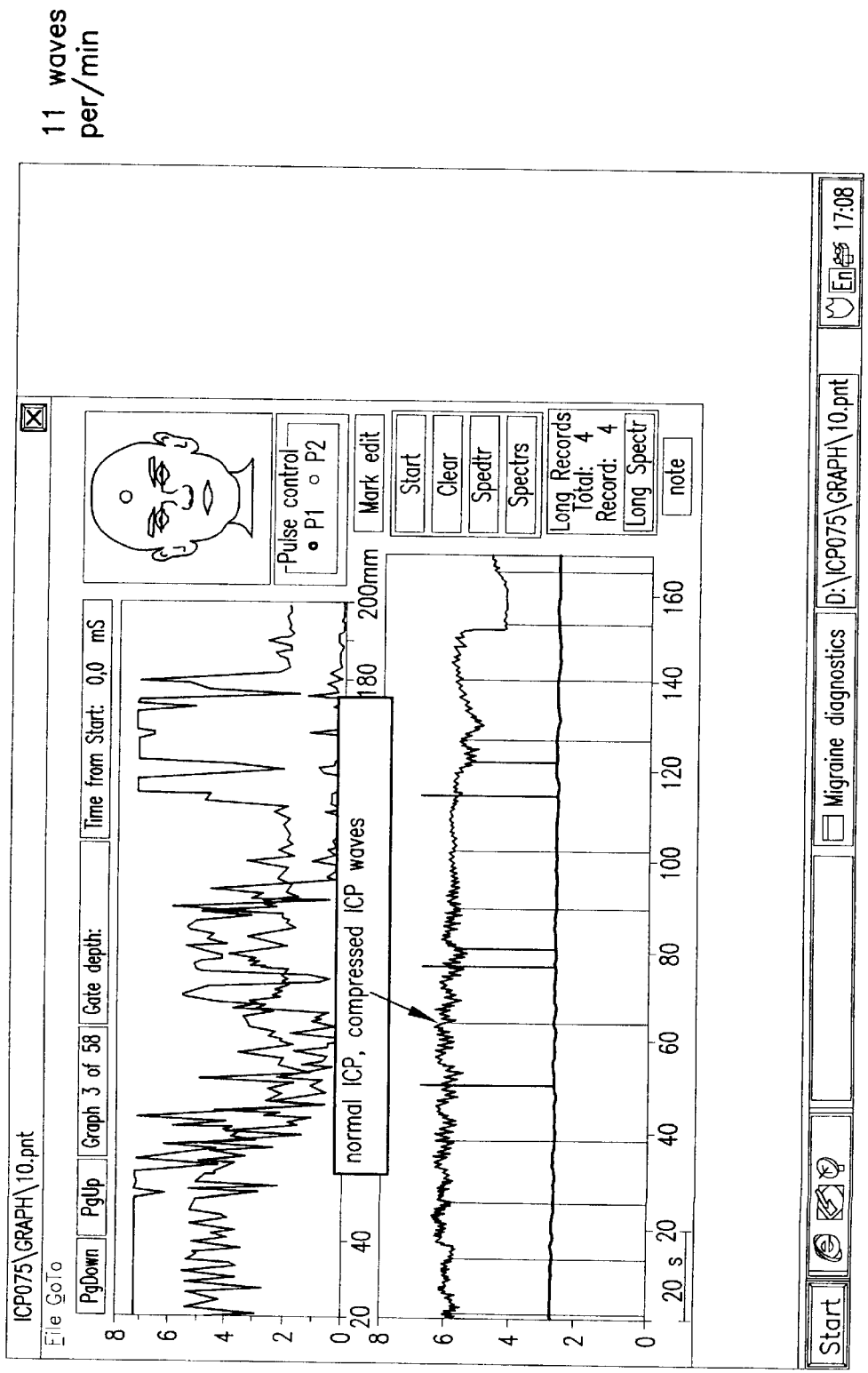
FIG. 11 is an Echo EG waveform and corresponding EPG waveform for another patient with normal ICP.

The compressed EPG waveforms of FIGS. 10 and 11 which exhibit 10 peaks and 11 peaks every minute, respectively, are in the form of "B-waves", and are therefore indicative of an ICP between 10–12 mm Hg (normal value of ICP).

Figure 12:
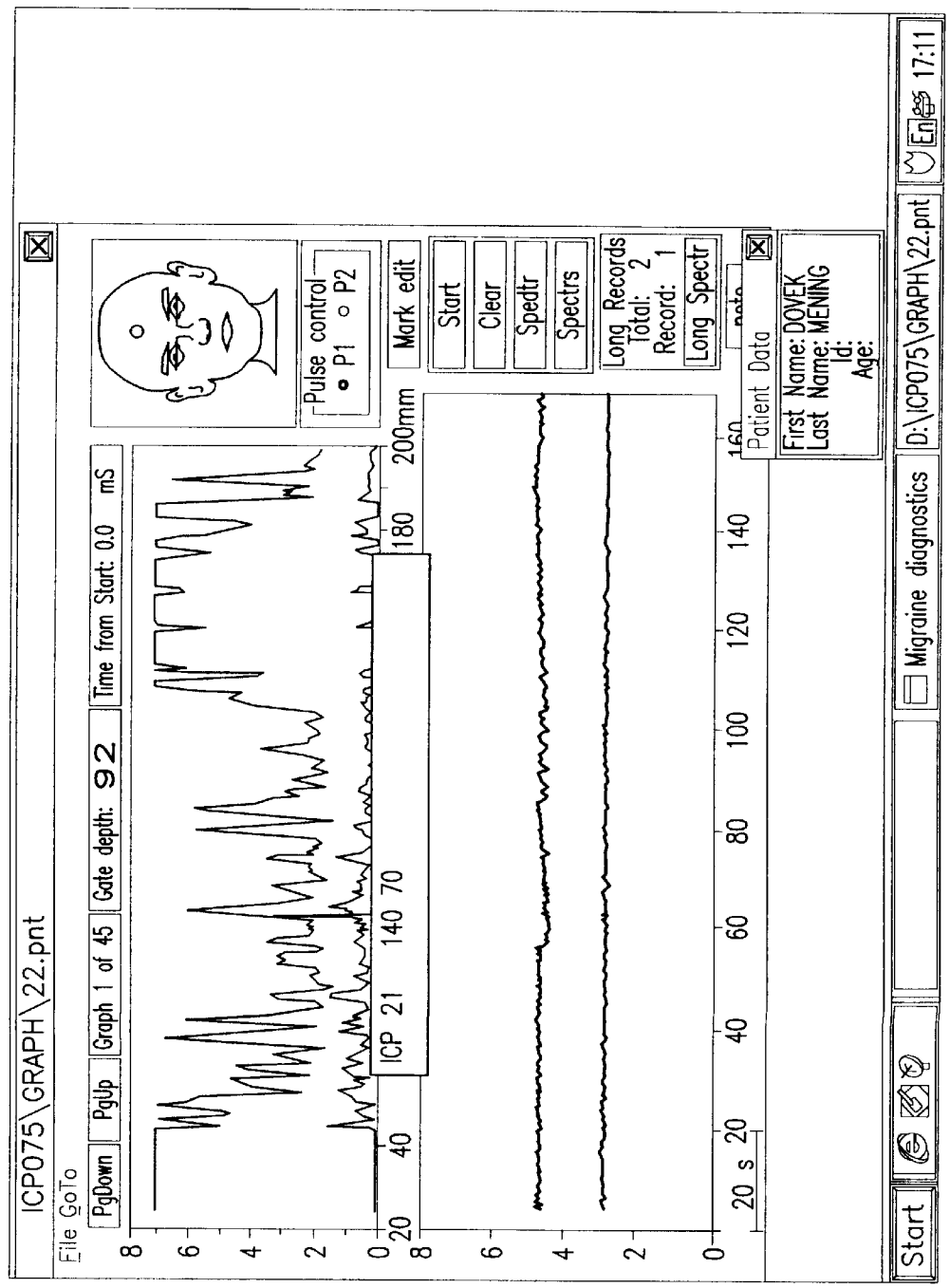
FIG. 12 is an Echo EG waveform and corresponding EPG waveform for a patient with moderately high ICP.
Figure 13:
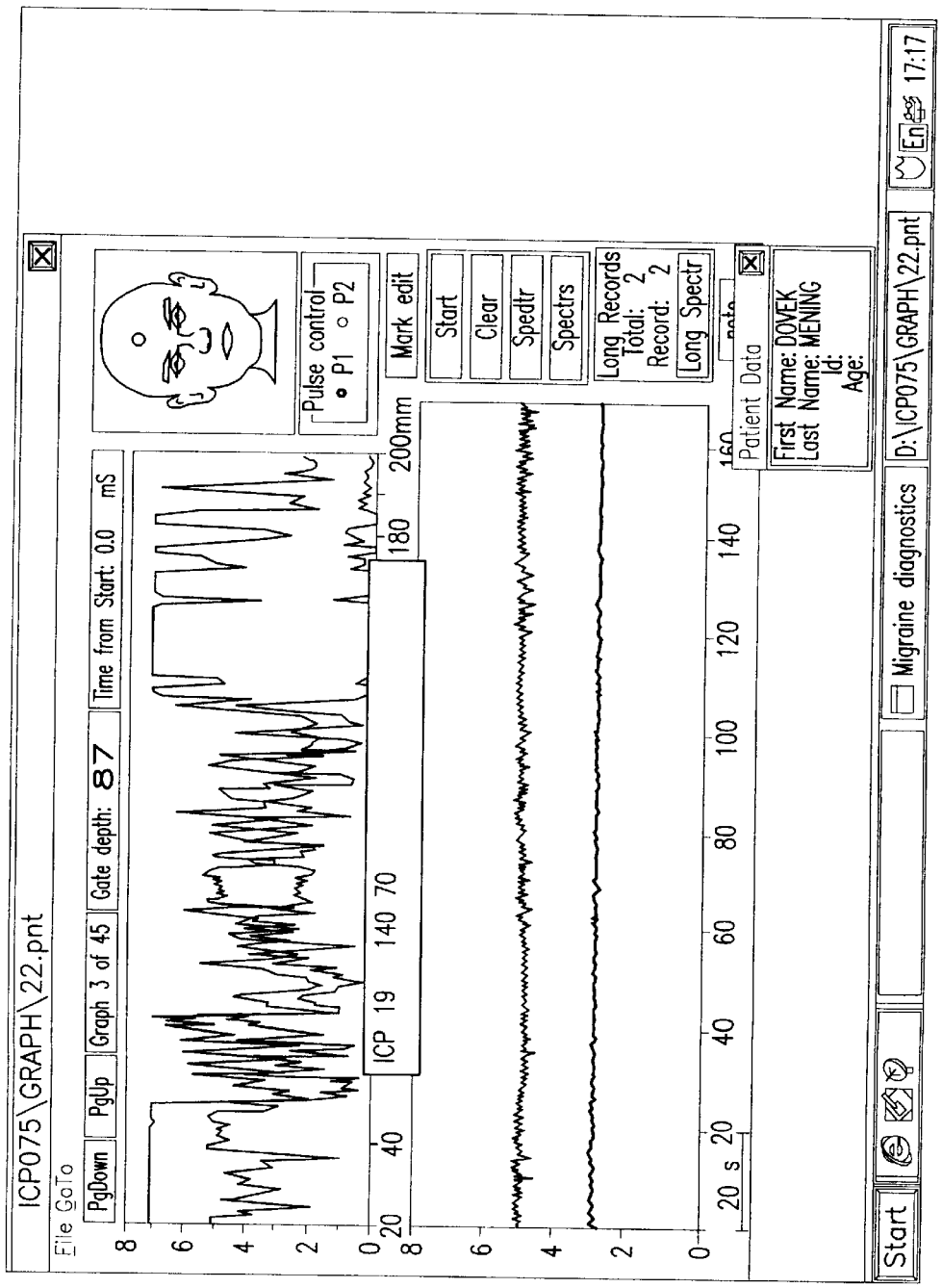
FIG. 13 is an Echo EG waveform and corresponding EPG waveform for a patient with high ICP.

FIG. 12 shows a compressed EPG waveform for a patient having an invasively measured ICP of 21 mm Hg. The compressed EPG waveform is a combination of flat waves and waves having about 16–20 peaks per minute, which is indicative of C waves and an ICP between 18 and 30 mm Hg. FIG. 13 shows an alternative C-wave waveform, also indicative of ICP between 18 and 30 mm Hg, which is characterized by higher frequency waves of about 20–30 peaks per minute.

As demonstrated in FIGS. 6–12 above, in accordance with the present invention, it is possible to monitor, non-invasively, the pulsatility of specific areas of the brain. This is significant because, in any given patient, the pulsatility in one area of the brain may not be the same as the pulsatility in another area of the brain, because local damage of brain tissue, for example, the presence of tumors, blood clots, contusions and other anomalies.

Calibration of ICP Measurement

Figure 2C:
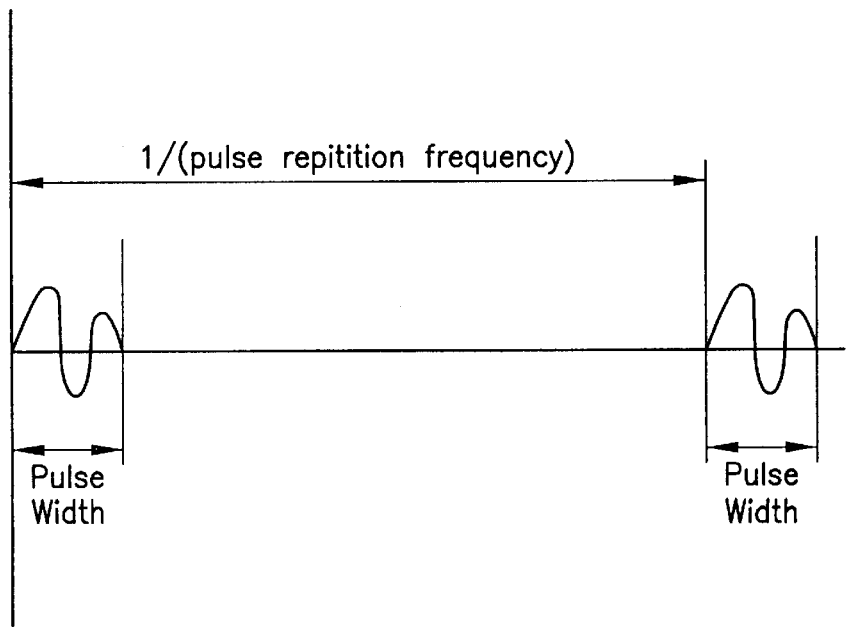
FIG. 2(c) illustrates a waveform transmitted by the probe of FIG. 2(b)
Figure 14A:
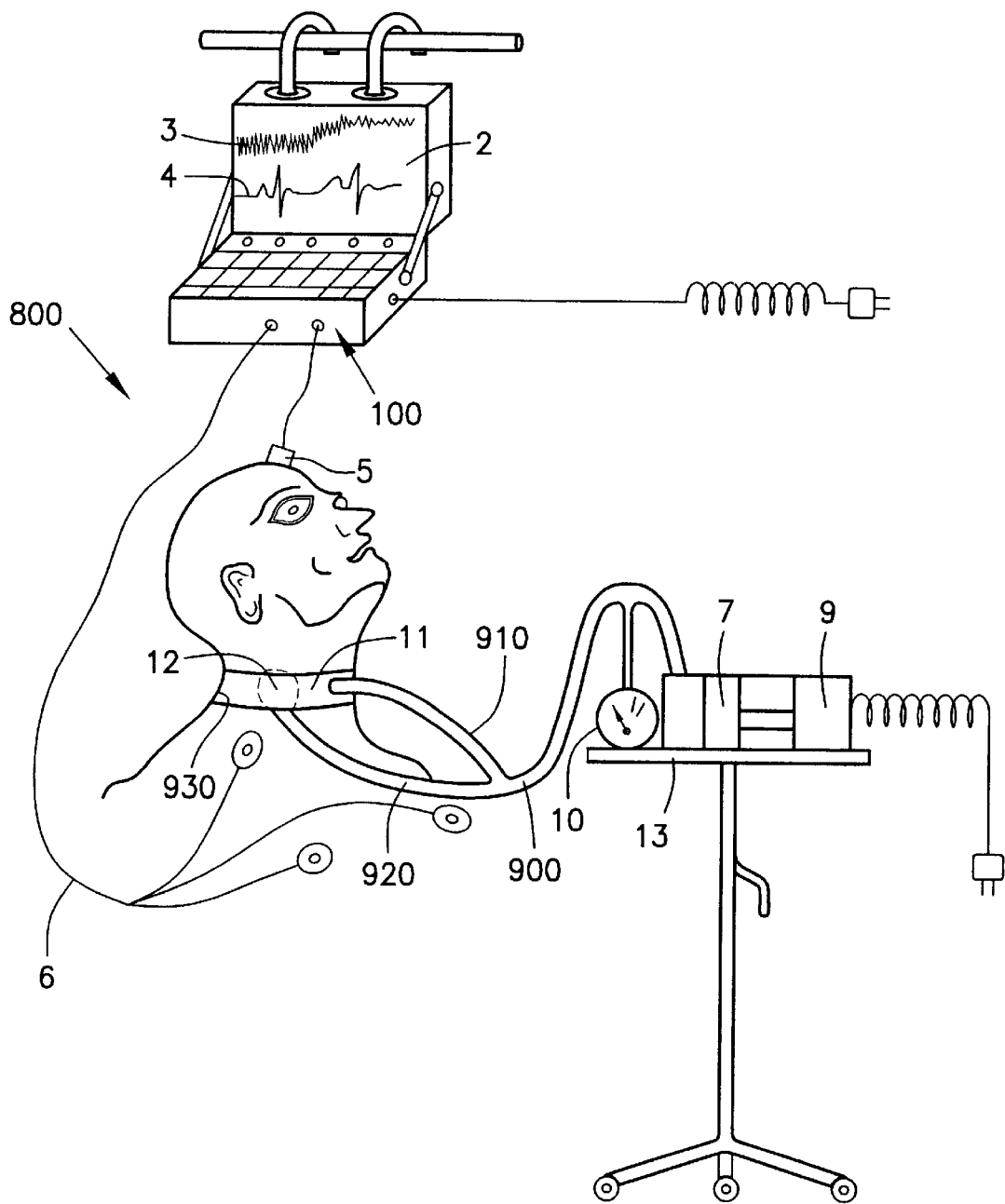
FIG. 14(a) shows an illustrative calibration device in accordance with an embodiment of the present invention.

FIG. 14(a) shows a preferred device 800 for calibrating the device 100 of FIG. 2 for the measurement of ICP. The device 800 includes a constant volume pump 8 for transmitting a constant volume of a medium (such as air, water, oil, etc) through a chamber 900, which leads to chambers 910 and 920 respectively. Chambers 910 and 920 terminate in respective bladders 11 and 12 in neck collar 930. The bladders 11 and 12 are positioned on the interior side of the neck collar 930 so that they are adjacent the external jugular vein and the internal jugular vein when the neck collar is secured around the neck of a patient. A pressure display device 10 is also coupled to the chamber 900 for monitoring the pressure in the chambers 900, 910, 920.

The pump 801, chambers 900, 910, 920, and bladders 11, 12 are constructed in such a manner as to apply pressure to the jugular veins 501, 502 in constant increments as the pump 801 is operated. For example, the chambers 806–808 may be constructed of hollow tubes made of polyethylene plastic, the bladders 804–805 may be made of a substantially non-elastic nylon or polyethylene membrane, and the medium may be air. In general, the pump 801 and the display device 802 may be of any known type. However, the material chosen for the bladders 804–805 and the chambers 806–807 should be materials which will not cause hysteresis during operation.

In order to calibrate the apparatus 100 of FIG. 2, ultrasound measurements are taken with the probe 101, gated on the third ventricle of the patient, to produce an EPG signal as described above. Preferably, a compressed EPG waveform is used which includes only the minimum and maximum EPG waveform values for each cardiac cycle.

The constant volume pump is used to apply a constant volume of fluid or gas to the bladders 804 and 805, thereby increasing the pressure on the interior and exterior jugular veins at a constant rate. Preferably, the pump 801 increases the pressure in increments of 2 mm Hg per rotation of the pump actuator.

Figure 15:
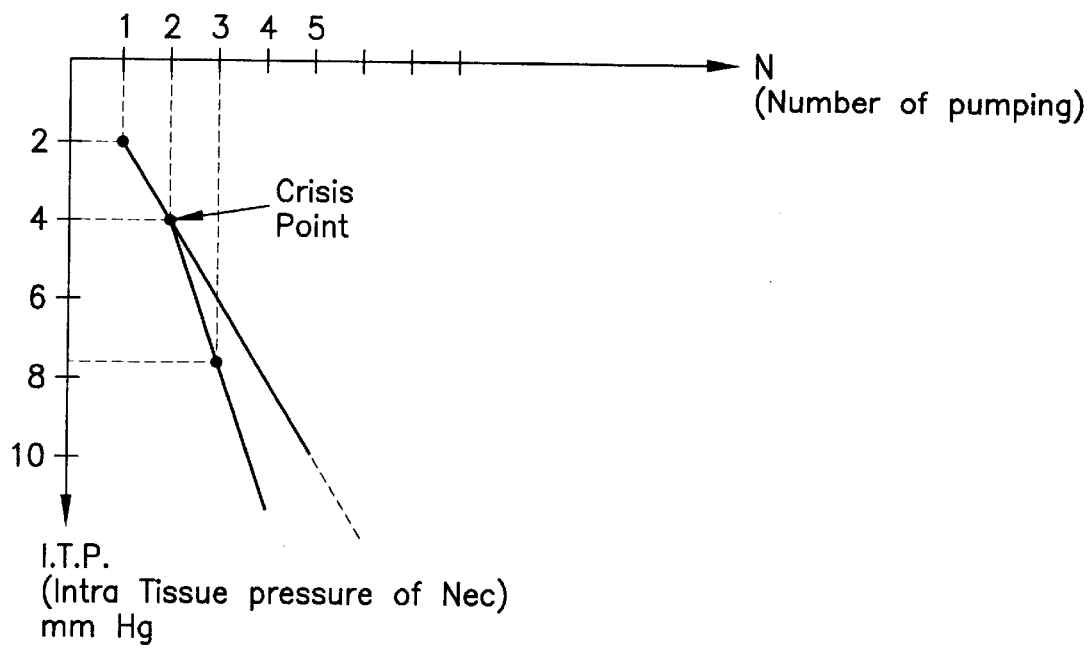
FIG. 15 is a plot of pump iterations vs. intra tissue pressure for the longEPG waveform which would be generated during calibration using the device of FIG. 14(a).

The pressure is increased until the baseline level (the average EPG amplitude corrected for the respiratory wave) of the Long-EPG signal falls. The pressure value just prior to the first fall in Long-EPG is then taken as an estimation of the pressure required to compress the skin in the neck without compressing the jugular vein, and will be referred to herein as the "crisis point". FIG. 15 schematically illustrates the relationship between pump iterations (at 2 mm Hg per iteration) and intra tissue pressure on the neck. In FIG. 15, the crisis point is identified at 4 mm Hg.

Then, the pressure is increased in to 19 mm Hg by applying 7½ pump iterations. The amplitude A1 of the EPG waveform is then noted. At this point, the general pressure (P) necessary to compress the jugular vein has been reached, with P=19 mm Hg=ITP+ICP, wherein ITP=4 mm Hg (FIG. 15). This corresponds to an ICP of 15 mm Hg.

Figure 16:
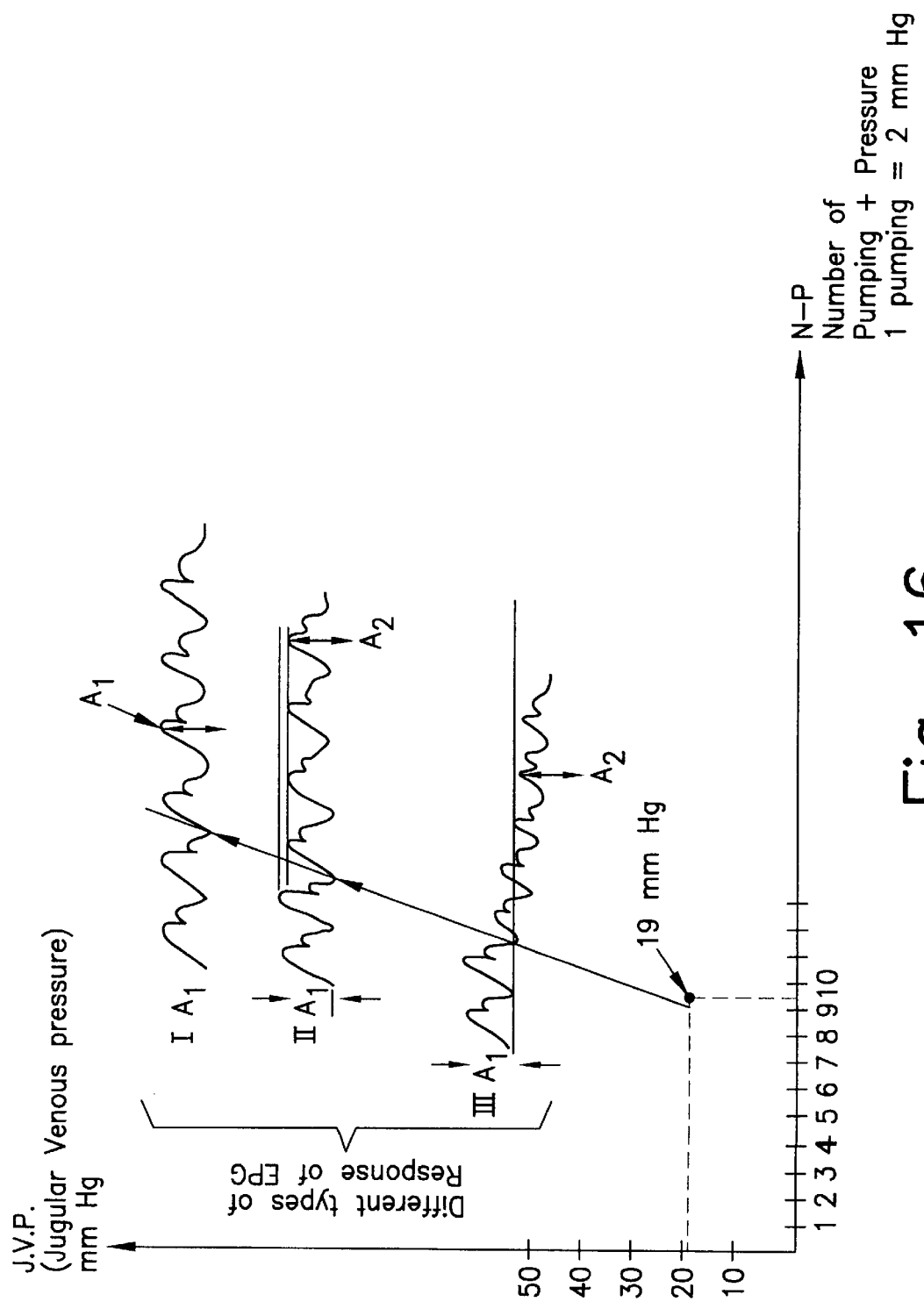
FIG. 16 is an illustration of different EPG waveform responses to the application of increasing pressure to the jugular veins via the device of FIG. 14(a).

The pressure is then increased 2 mm Hg to 21 mm Hg and an amplitude A2 of the EPG waveform is noted. If the amplitude A2 is less than about 95% of the amplitude A1, then no calibration of the device 100 is required. If the amplitude A2 is more than about 95% of A1 (plots I and II of FIG. 16), then pressure is increased another 2 mm Hg and another amplitude A2 is noted. If the amplitude A2 is less than about 95% of the amplitude A1, then ICP=15+2 mm Hg=17 mm Hg. If the amplitude A2 is more than about 95% of A1, then pressure is increased in increments of 2 mm Hg until A2 is less than about 95% of A1, to obtain a value for ICP. The value for ICP obtained by the above method is then compared with the non-invasive ICP value obtained with the device 100 of FIG. 2, and the system is calibrated accordingly. In this regard, the difference between the ultrasound measurement and the neck collar measurement is assumed to be a constant K=ICP(ultrasound)−ICP(neck collar). Subsequent ultrasound measurements for the patient are then calculated as ICP=ICP+K.

Figure 17:
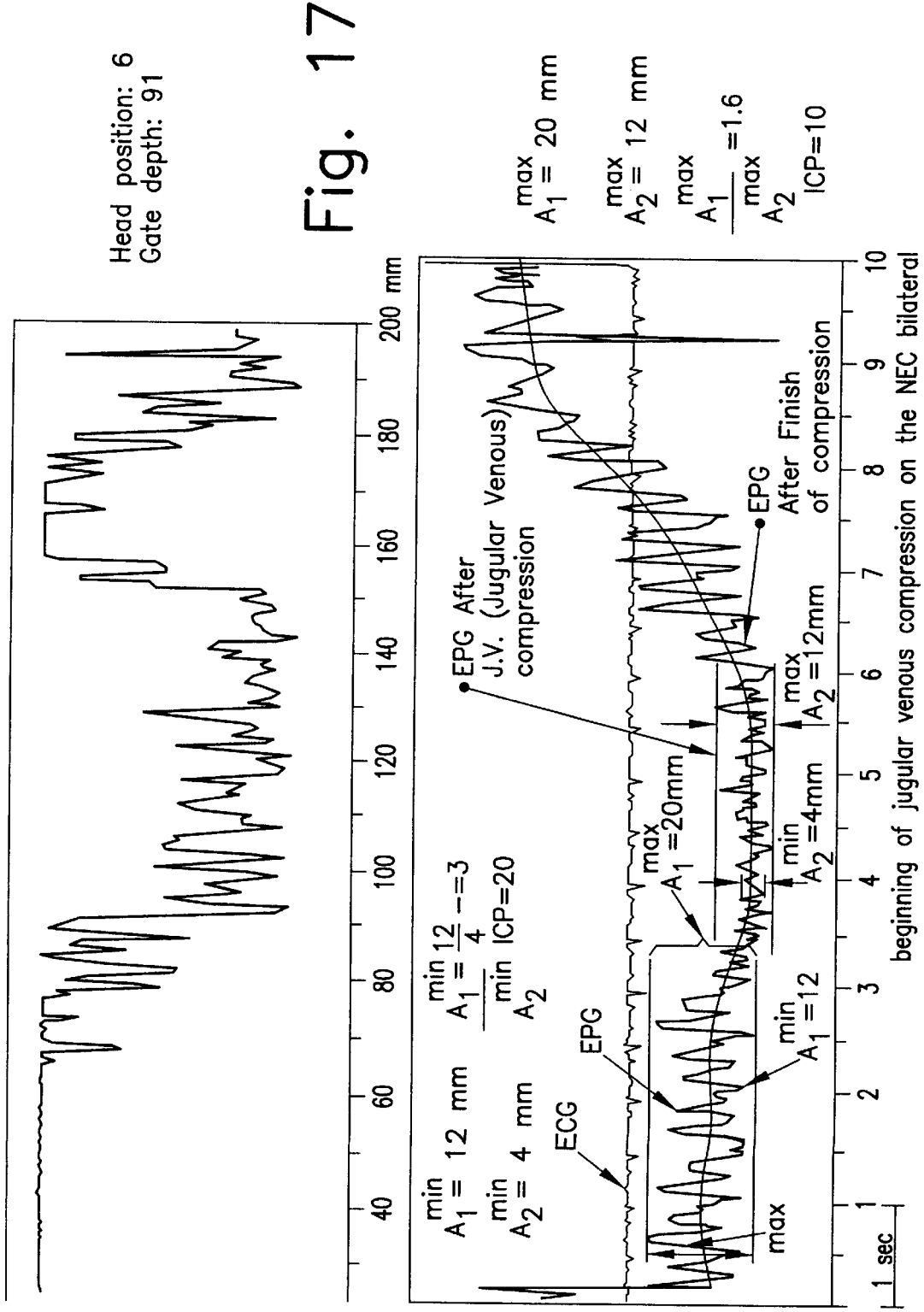
FIG. 17 shows an Echo EG waveform for a patient gated at a depth of 91 mm, and a corresponding EPG waveform and respiratory wave before and after compression of the jugular veins with the device of FIG. 14(a).
Figure 18:
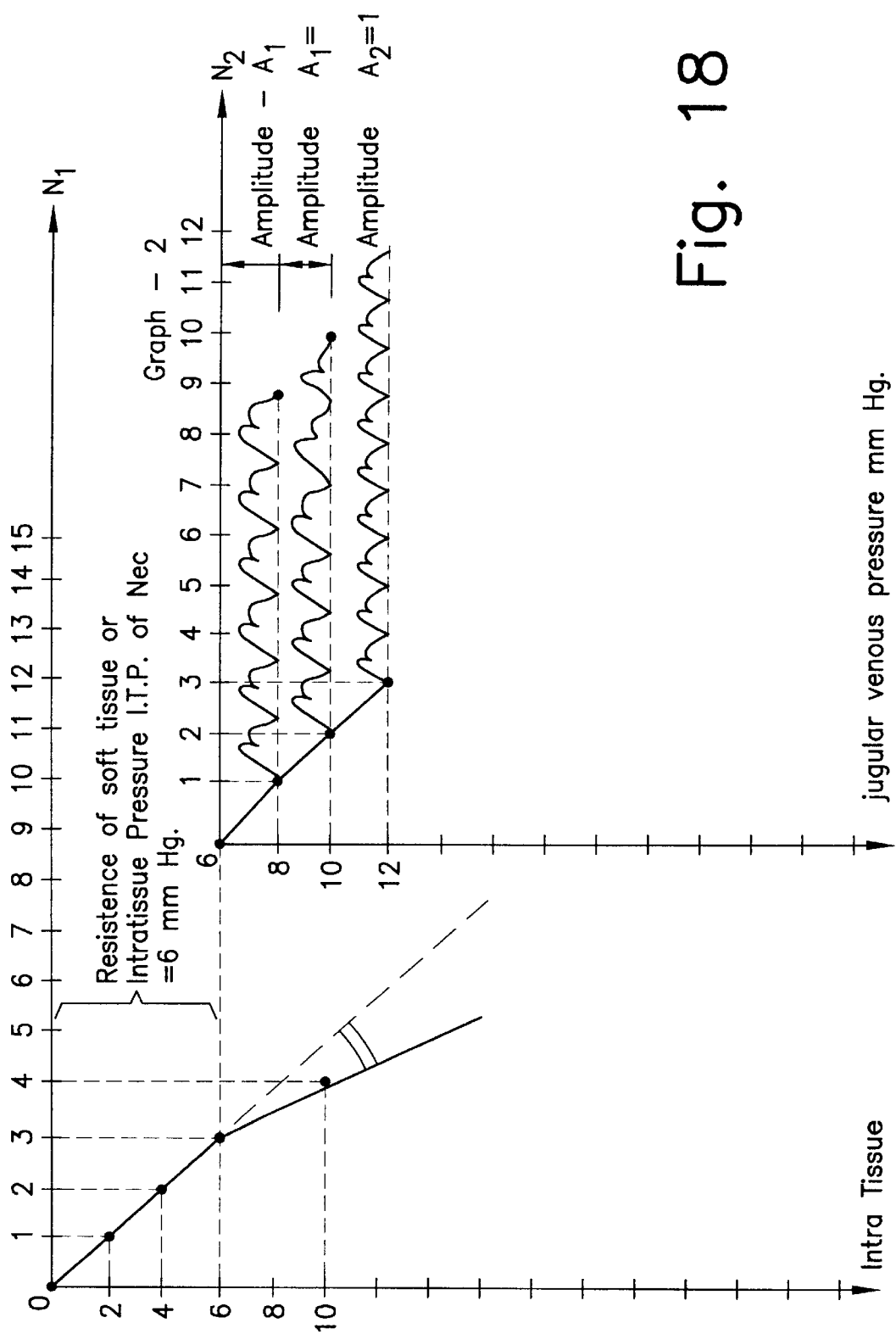
FIG. 18 shows a plot of pump iteration vs. intra-tissue pressure and jugular venous pressure for the patient of FIG. 17.

A second calibration method for use with the device of FIG. 13 can be illustrated with reference to FIGS. 17–19. FIG. 17 illustrates an Echo EG signal for a patient gated at 91 mm, and a corresponding EPG signal. As described above, the constant volume pump is used to apply a constant volume of fluid to the bladders 804 and 805, thereby increasing the pressure on the interior and exterior jugular veins at a constant rate until the baseline level (the average EPG amplitude corrected for the respiratory wave) of the Long-EPG signal falls. This "crisis point" value is taken as an estimation of the pressure required to compress the skin in the neck without compressing the jugular vein. In the patient of FIG. 17, the crisis point is 6 mm Hg, as shown in FIG. 18. Minimum and maximum amplitudes ($A1_{min}$, $A1_{max}$) of the EPG waveform are then noted as illustrated in FIG. 17. The pressure is then increased in increments of 2 mm Hg until the amplitudes of the EPG signal ($A2_{min}$, $A2_{max}$) are less than about 95% of A1. This is considered the point of jugular venous compression.

Figure 19:
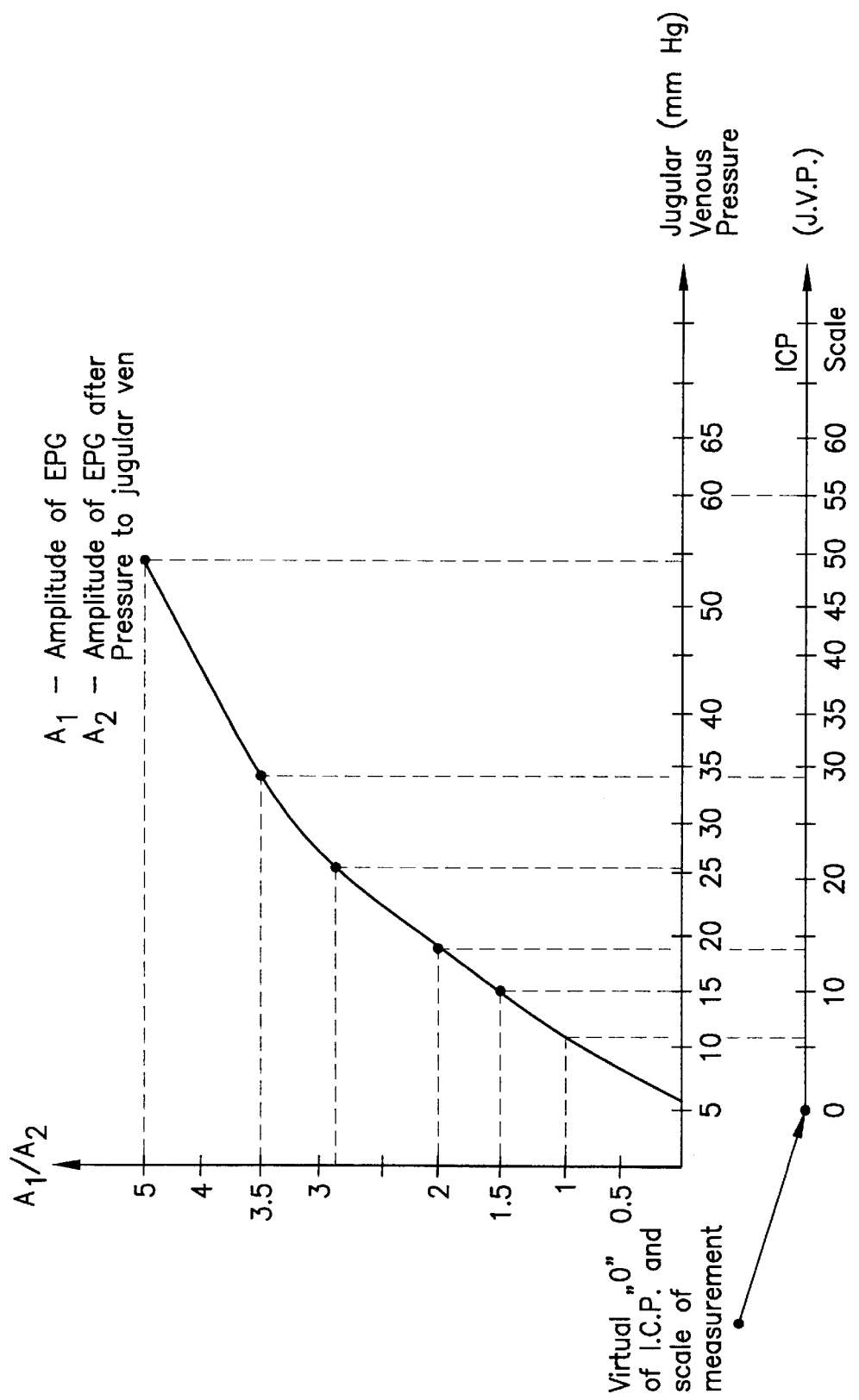
FIG. 19 shows a relationship between EPG amplitude prior to (A1) and after (A2) compression of the jugular veins which can be used to calibrate the device of FIG. 14(a).

FIG. 19 is a plot of the relationship between A1/A2 (Y-axis) and jugular venous pressure (X-axis). Plotted below the X-axis are the values for ICP for the patient of FIG. 18, taking into account the crisis point at 6 mm Hg. Referring to FIG. 17, $A1_{min}/A2_{min}=12/4=3$, $A1_{max}/A2_{max}=20/12=1.6$, and $A1_{avg}/A2_{avg}=((20+12)/2)/((12+4)2)=16/8=2$. Plotting these values in FIG. 19, we have $JVP_{max}=26$, $JVP_{min}=16$ and $JVP_{avg}=19$, and $ICP_{max}=20$, $ICP_{min}=10$, and $ICP_{avg}=13$. The system is then calibrated accordingly. In this regard, the difference between the ultrasound measurement and the neck collar measurement is assumed to be a constant K=ICP (ultrasound)−ICP(neck collar). Subsequent ultrasound measurements for the patient are then calculated as ICP=ICP+K.

In general, this procedure will require no more than a 50% osculation of the jugular veins for 3 seconds to 15 seconds. Calibration is preferably repeated every 2 days for each patient.

In normal patients, each calibration may involve performing the procedure described above three or four times to obtain an average value for ICP. Most preferably, the procedure is performed at least once during inspiration, at least one during expiration, and at least once during normal breathing to provide an average value.

The device 800 is also useful, in and of itself, as a diagnostic tool. For example, as described above, it can be used to measure ICP in a patient in cases in which frequent or extended monitoring of ICP is not desired.

Figure 14B:
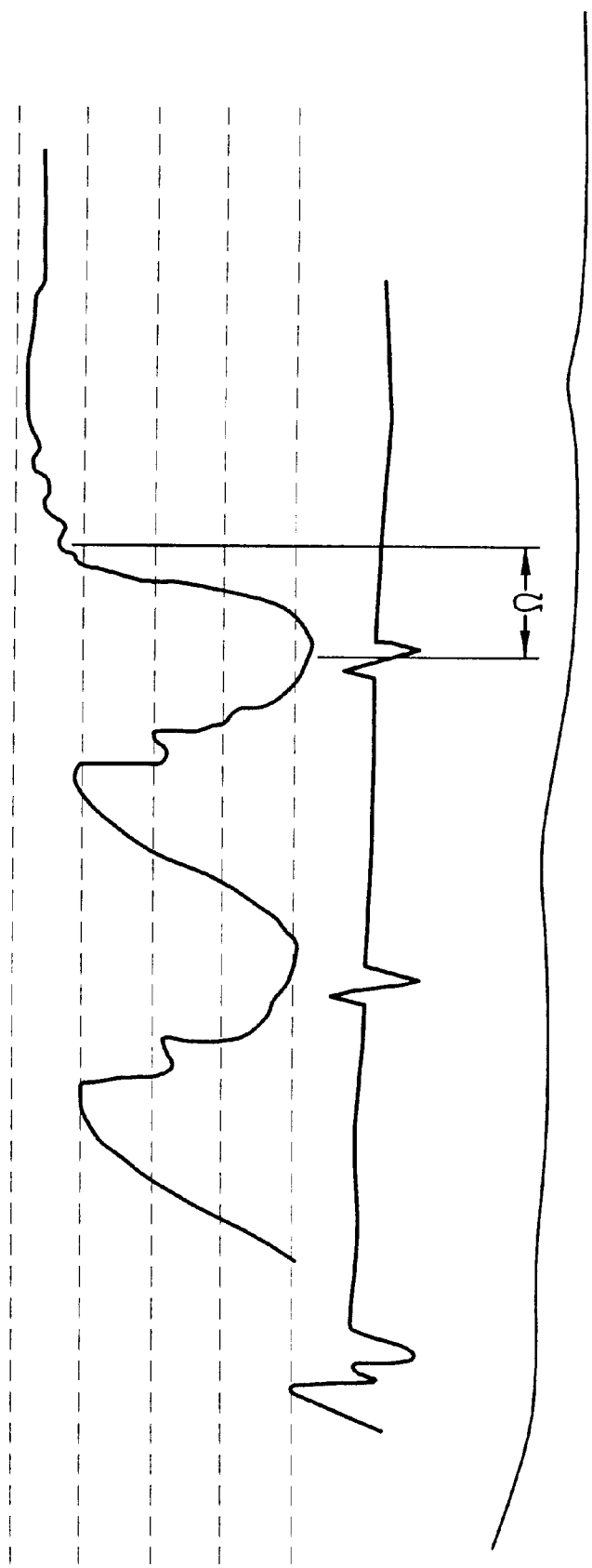
FIG. 14(b) illustrates the generation of plateau waves with the device of FIG. 14(a)

The device 800 can also be used to provide an indication of vascular patency. In this regard, the constant volume pump is used to increase the pressure on the interior and exterior jugular veins until the EPG signal changes to a plateau wave as shown in FIG. 14(b). The time from the last incremental pressure increase from pump 802 until the onset of plateau waves (Ω) can then be used as an indication of venous or vascular patency, or of the available reserve intracranial space or compensatory capacity. In this regard, a short Ω time is indicative of low patency and/or less available reserve space (or compensatory capacity) within the skull, while a longer Ω is indicative of of high patency and/or more available reserve space (or compensatory capacity).

Automation of ICP Measurement

In accordance with one embodiment of the present invention, the apparatus 1 and EPG, Echo EG, and ECG waveforms are generated and interpreted manually by a technician in the manner described above in order to monitor pulsatility in the brain, and to, for example, determine the ICP at particular brain regions. However, in accordance with further embodiments of the invention, this procedure can be further automated as described below.

For example, in accordance with one embodiment of the invention, the apparatus is configured to allow a technician to select a broad gate range, for example 40–60 mm, and to gate the Echo EG waveform at multiple depths within that range to provide multiple EPG waveforms. For example, for a gate range of 20 mm (e.g. between 40 and 60 mm), the apparatus could provide gates at intervals of 1 mm (totaling 20 gates), 2 mm (10 gates), or 4 mm (5 gates). The technician could then review the EPG waveforms at each gate to determine which provides the optimal EPG waveform for a site of interest in the brain.

In accordance with a still further embodiment of the invention, a typical EPG waveform for a site of interest (for example, the third ventricle) could be stored on the computer 107. Each of the gated waveforms could then be compared to the stored waveform, and the gated waveform which most closely resembles the stored waveform could be identified to the technician.

The multiple gating feature could be implemented in a number of ways. For example, it could be implemented entirely in software using the single gating circuit 104 of FIG. 1. In this embodiment, the Echo EG signal is gated only once during each transmitted ultrasound pulse, and the gated location is incremented (e.g. by 1, 2, or 4 mm) during each successive ultrasound pulse until an EPG waveform is generated for each gate within the gate range. Alternatively, a plurality of gating circuits 104 could be provided, allowing the Echo EG signal to be gating at plurality of depths in parallel to produce a plurality of EPG waveforms from a single transmitted ultrasound pulse. Moreover, these techniques are not mutually exclusive. For example, an apparatus could employ multiple gating circuits (for example 4), and also allow serial incrementing of gate locations, thereby providing the capability to gate at 20 locations with only 5 ultrasound pulses.

In accordance with another embodiment of the invention, the DFT or FFT techniques described above with regard to FIGS. 9 through 12 may be used to further automate the determination of ICP. In this regard, the computer 107 could be programmed to automatically perform of DFT or FFT on the EPG waveform, to automatically identify the dominant second resonant frequency, to automatically map the resonant frequency back onto the EPG signal, and to automatically select the appropriate characteristic plot representative of the relationship between t/T and ρ(e.g., plots I, II, or III of FIG. 5), calculate ρ according to the selected characteristic plot, and the calculations of ICP using the appropriate formula for ICP: for $\rho=\rho_1$, $\rho_2$, or $\rho_3$, $ICP=\rho(t/T)*[t/T]-\beta$, and For $\rho=\rho_0$, $ICP=\rho(t/T)*[t/T]$.

Measurement of Location and Width of Vessels and Ventricles In the Brain

In accordance with another embodiment of the present invention, the EPG signal is used to determine the width and position of ventricles and blood vessels. In accordance with this embodiment, the opposing walls of a ventricle or blood vessel are identified from the EPG and Echo EG waveforms. FIGS. 20 through 23 illustrate a preferred method for identifying the width and position of the third ventricle of a patient. Once the position of the third ventricle is identified, the existence and extent of midline shift for a patient can be calculated as a displacement of the third ventricle relative to the centerline of the skull.

Figure 20:
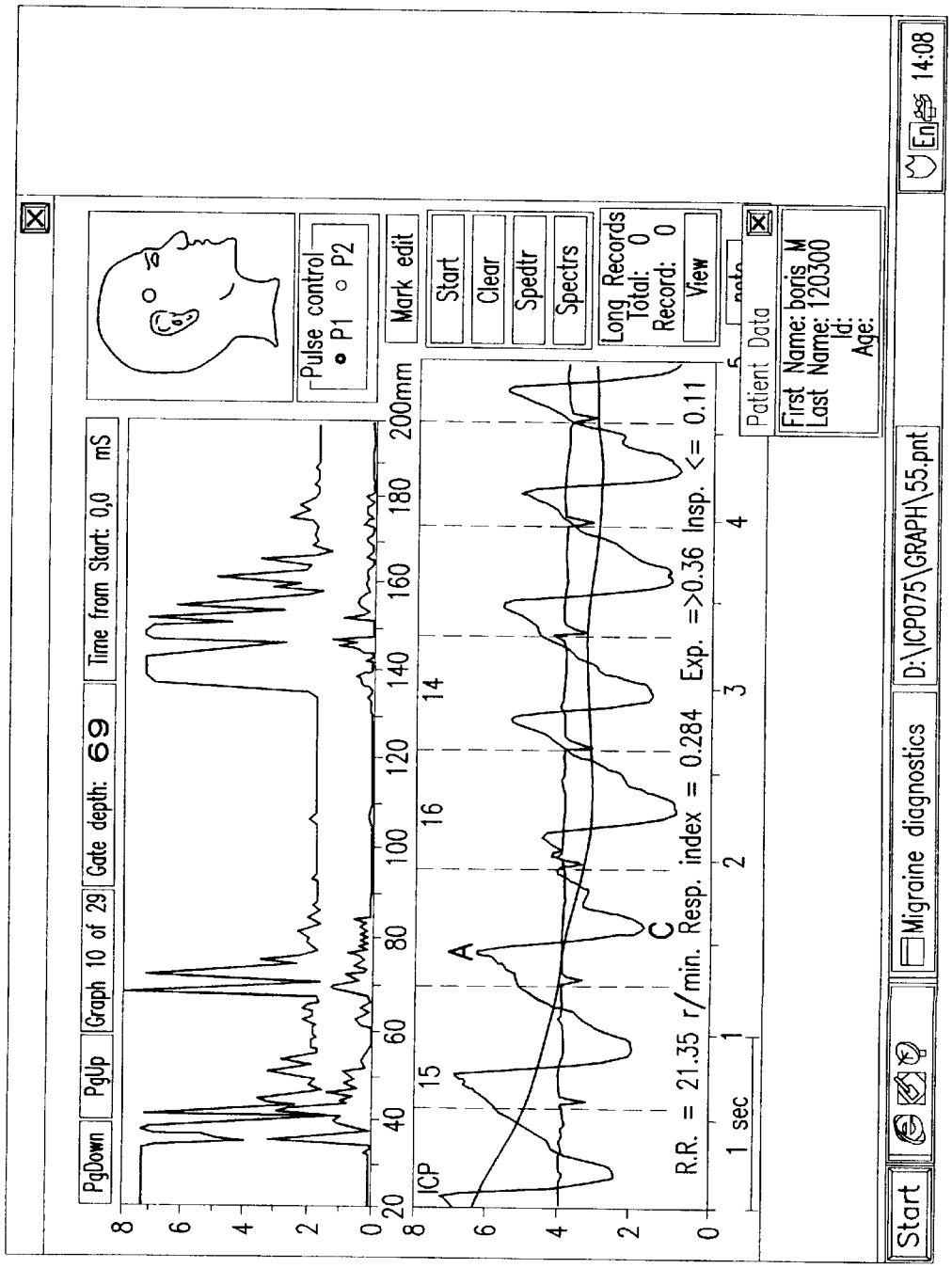
FIG. 20 shows an Echo EG waveform for a patient gated at a depth of 69 mm from a right temporal area of the skull, along with a corresponding EPG waveform and respiratory wave, wherein the EPG waveform is a negative phase signal.

FIG. 20 shows an Echo EG waveform for a patient in an upper plot, along with a corresponding EPG waveform, ECG waveform and respiratory wave in a lower plot. Referring to FIG. 20, an ultrasound probe 101, or 101' is placed on the right temporal area of the skull of a patient and an ultrasound pulse is transmitted from the ultrasound probe into the skull of the patent in the manner described above. The reflected signal from said ultrasound pulse is then received, and processed to generate the Echo EG signal shown on the upper plot of FIG. 20. A dominant portion of said echo encephalogram signal corresponding to the third ventricle is then selected at a gate depth of 69 mm, and the Echo EG signal is integrated across the gate to generate the EPG signal displayed in the lower plot of FIG. 20. At this point, the phase of the EPG signal is noted. In this regard, an EPG signal is identified as a positive phase signal if the maximum amplitude of the signal following a cardiac systole has a positive value, and as a negative phase signal if the maximum amplitude of the signal following a cardiac systole has a negative value.

If the echo pulsogram signal has a positive phase, then the selected portion of the echo encephalogram is identified as corresponding the far wall of the vessel or ventricle relative to the ultrasound probe. If the echo pulsogram signal has a negative phase, then the selected portion of the echo encephalogram is identified as corresponding the near wall of the vessel or ventricle relative to the ultrasound probe.

Figure 24A:
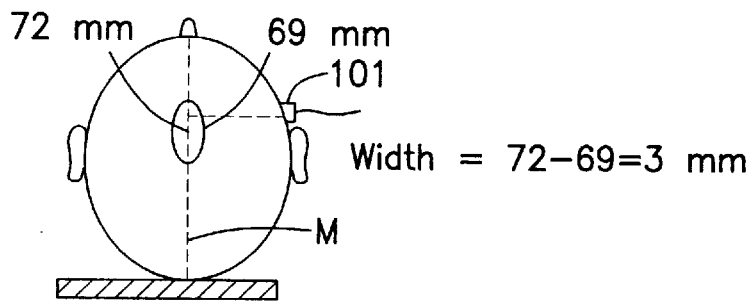
FIG. 24a illustrates the location of the walls of the third ventricle identified by the waveforms of FIGS. 20 and 22.
Figure 24B:
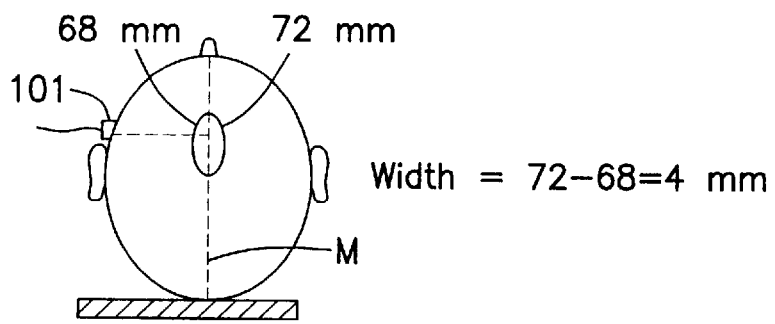
FIG. 24b illustrates the location of the walls of the third ventricle identified by the waveforms of FIGS. 21 and 23.
Figure 24C:
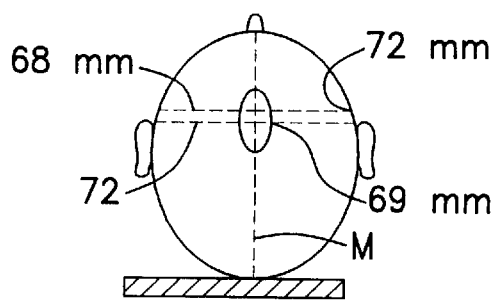
FIG. 24c illustrates the manner in which midline shift can be quantified from FIGS. 20 through 23.

As shown in FIG. 20, following each cardiac systole, the amplitude of the EPG signal rises in a positive direction to point A (the beginning of venous pulsatility), then falls in a negative direction to point C (absolute maximum f(t)). Therefore, the EPG for the patient at a gate depth of 69 mm is a negative phase signal, and the position of the near wall of the third ventricle (relative to the probe) is estimated at 69 mm from the right temporal area of the patient as shown in FIG. 24(*a*).

Figure 22:
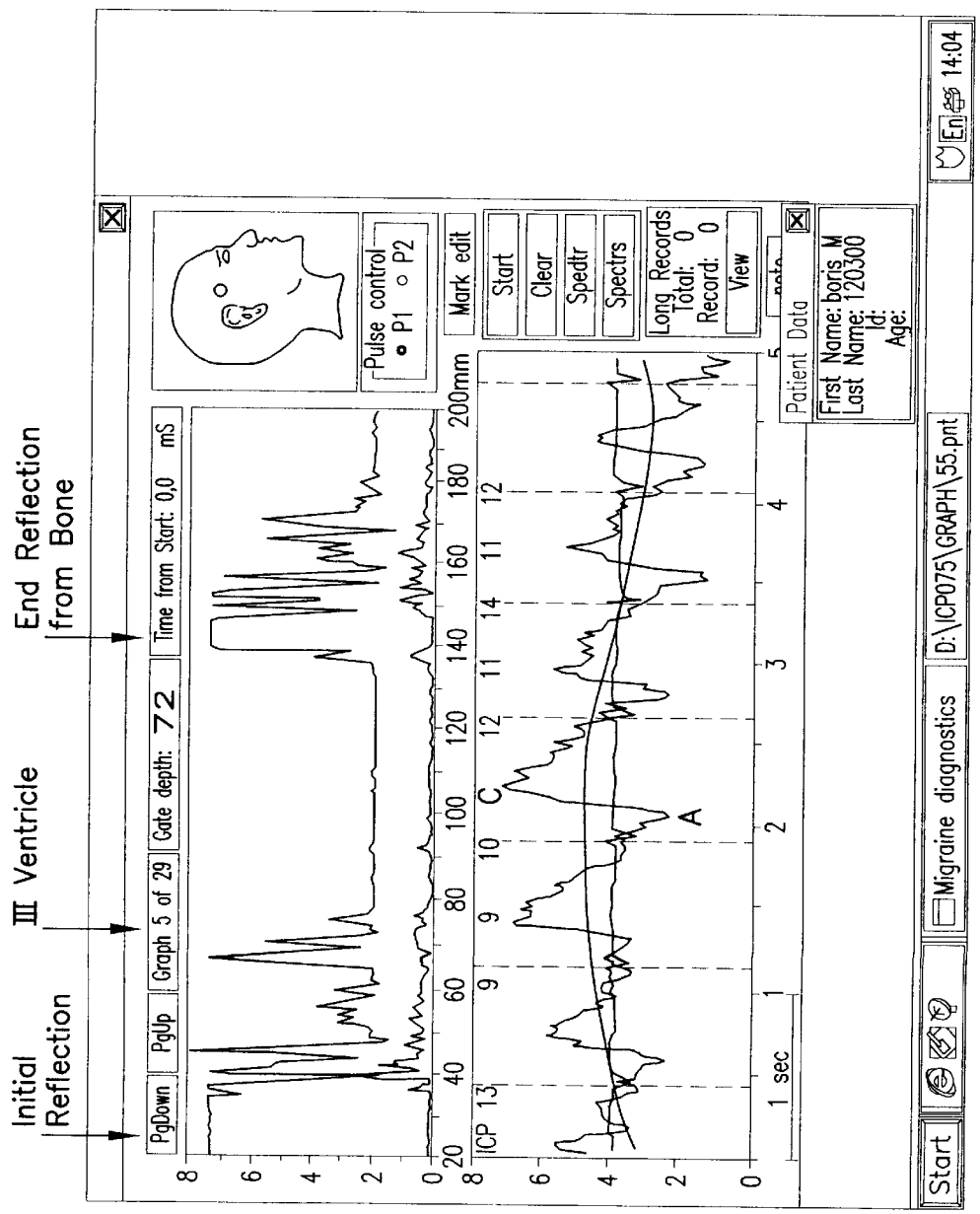
FIG. 22 shows an Echo EG waveform for the patient of FIG. 20 gated at a depth of 72 mm from a right temporal area of the skull, along with a corresponding EPG waveform and respiratory wave, wherein the EPG waveform is a positive phase signal.

In order to locate the far wall of the third ventricle, the Echo EG signal is gated at a location farther from the ultrasound probe. Preferably, a physician or technician selects a depth which corresponds to a typical width of the third ventricle. The echo EG signal is then integrated across the gate to generate an EPG signal. If the EPG signal is a positive phase signal, then the gate of the echo EG is identified as corresponding to the far wall of the third ventricle. If the EPG signal is a negative phase signal, then successive gates of the Echo EG are selected, which correspond to locations in the brain which are successively farther from the ultrasound probe, until a positive phase signal is identified. Referring to FIG. 22, the echo EG signal (upper plot) is gated at a depth of 72 mm, and is integrated across the gate to obtain an EPG signal (lower plot). Following each cardiac systole, the amplitude of the EPG signal of FIG. 22 falls in a negative direction to point A (the beginning of venous pulsatility), and then rises in a positive direction to point C (absolute maximum f(t)). Therefore, the EPG for the patient at a gate depth of 72 mm is a positive phase signal, and the position of the far wall of the third ventricle (relative to the probe) is estimated at 72 mm from the right temporal area of the patient, as shown in FIG. 24(*a*). The width of the third ventricle can then be estimated as 72 mm−69 mm=3 mm based upon ultrasound signals generated from the right temporal area.

Figure 21:
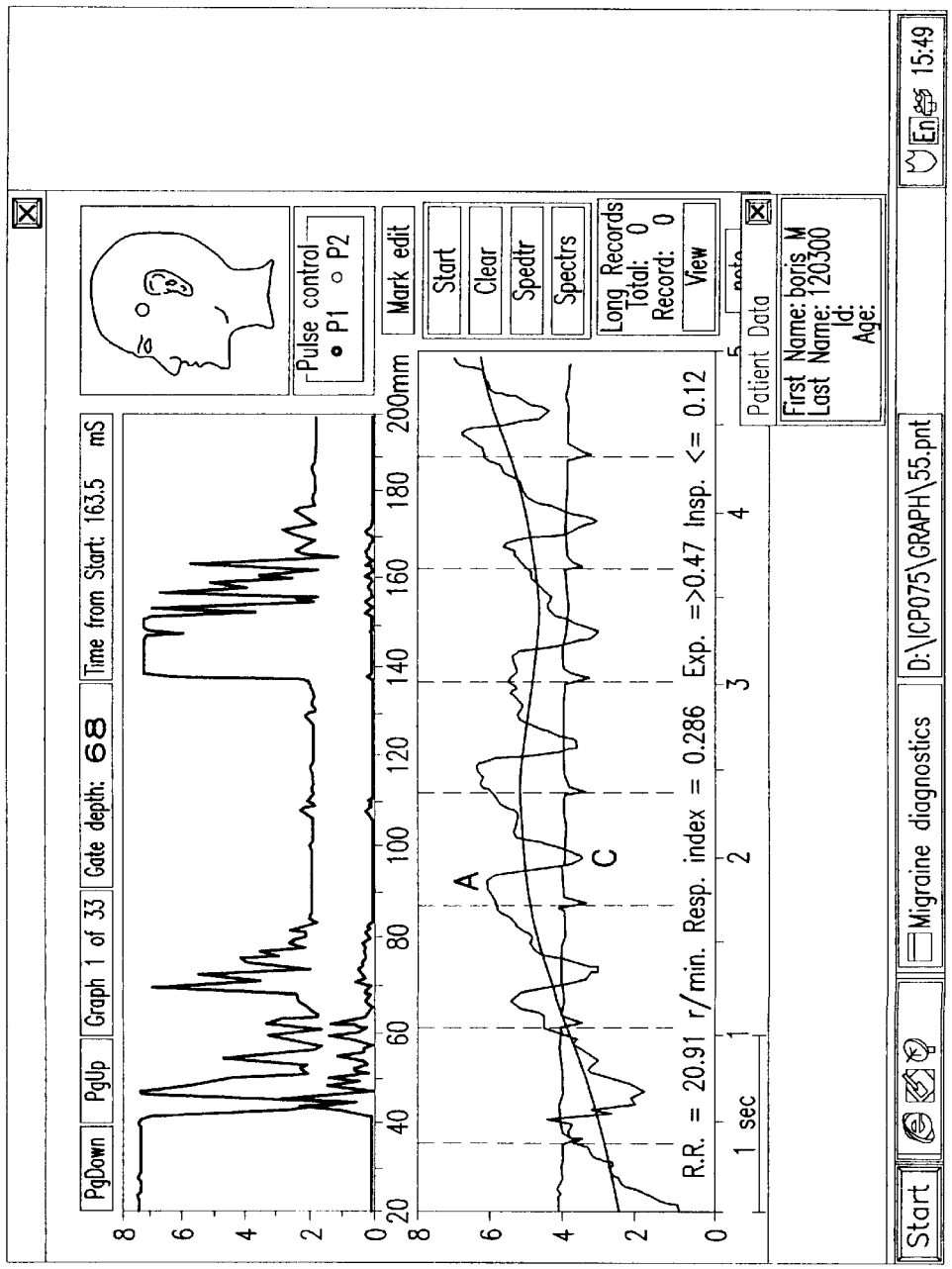
FIG. 21 shows an Echo EG waveform for the patient of FIG. 20 gated at a depth of 68 mm from a left temporal area of the skull, along with a corresponding EPG waveform and respiratory wave, wherein the EPG waveform is a negative phase signal.

In order to evaluate the presence and extent of midline shift, and in order to provide increase confidence in the accuracy of the measurement, the procedure set forth above is repeated from the left temporal area of the patient. FIG. 21 shows the Echo EG and EPG, ECG, and respiratory waveforms for the patient of FIG. 20, with the ultrasound probe 101, or 101' placed on the left temporal area of the skull of a patient, and the Echo EG waveform gated at 68 mm. Referring to the lower plot of FIG. 21, following each cardiac systole, amplitude of the EPG signal rises in a positive direction to point A (the beginning of brain (arterial, venous, ventricular, cisternal) pulsatility), then falls in a negative direction to point C (absolute maximum f(t)). Therefore, the EPG for the patient at a gate depth of 68 mm is a negative phase signal, and the position of the near wall of the third ventricle (relative to the left temporal area) is estimated at 68 mm from the left temporal area of the patient, as shown in FIG. 24(*b*).

FIG. 22 shows the Echo EG and EPG, ECG, and respiratory waveforms for the patient of FIG. 20, with the ultrasound probe 101, or 101' placed on the left temporal area of the skull of a patient, and the Echo EG waveform gated at 72 mm. Referring to the lower plot of FIG. 22, following each cardiac systole, amplitude of the EPG signal falls in a negative direction to point A (the beginning of venous pulsatility), then rises in a positive direction to point C (absolute maximum f(t)). Therefore, the EPG for the patient at a gate depth of 72 mm (from the left temporal area) is a positive phase signal, and the position of the far wall of the third ventricle (relative to the left temporal area) is estimated at 72 mm from the left temporal area of the patient, as shown in FIG. 24(*b*). The width of the third ventricle can then be estimated as 72 mm−68 mm=4 mm based upon ultrasound signals generated from the left temporal area.

Figure 23:
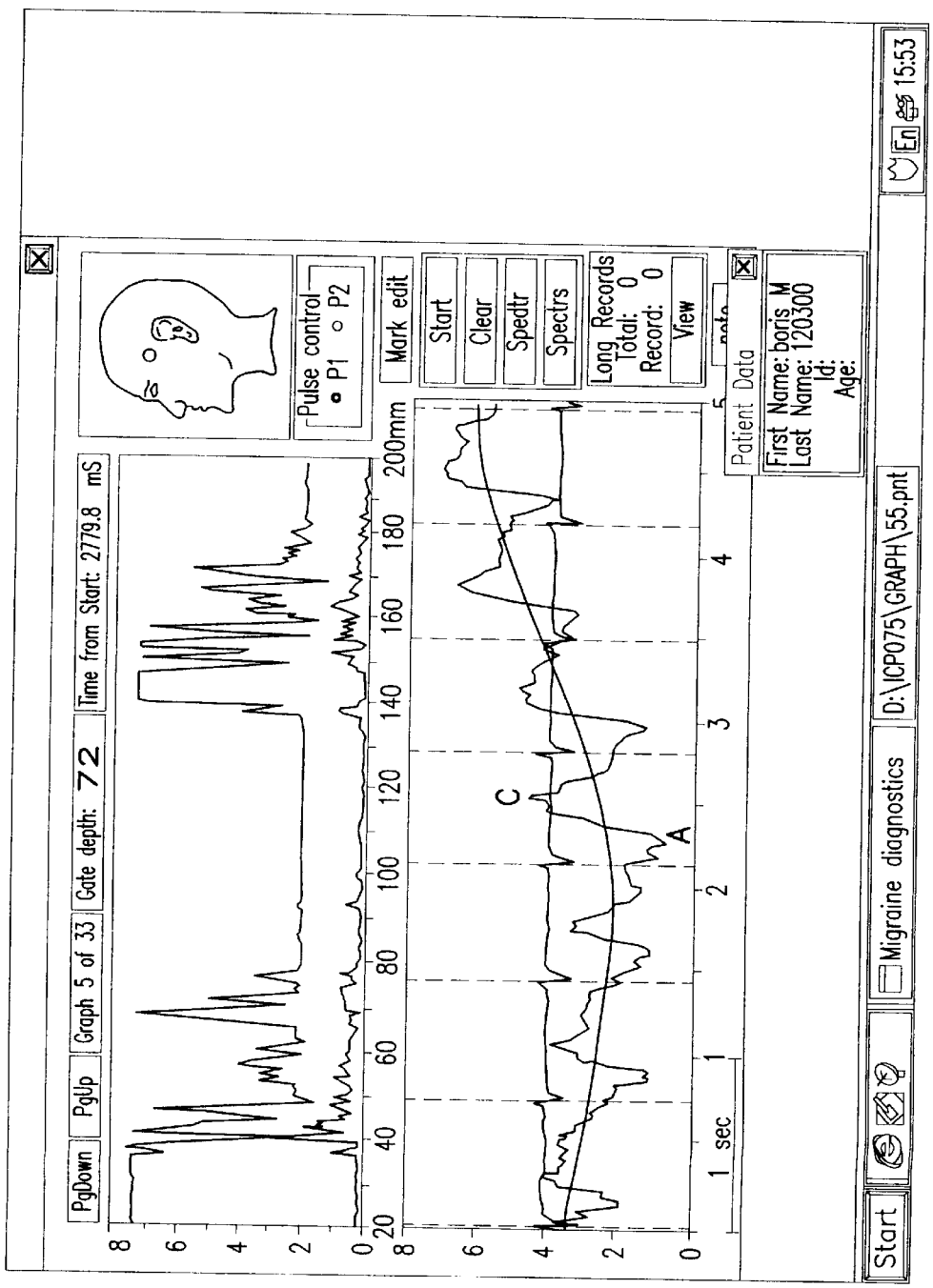
FIG. 23 shows an Echo EG waveform for the patient of FIG. 20 gated at a depth of 72 mm from a right temporal area of the skull, along with a corresponding EPG waveform and respiratory wave, wherein the EPG waveform is a positive phase signal.

The presence, and extent, of midline shift can be determined from the above data as follows. Referring to FIG. 23(*c*), based upon the assumption that the third ventricle is substantially symmetrical, if the third ventricle is located exactly at the midline (M), the distance from a probe on the left side temporal area to the nearest wall of the third ventricle (i.e., the left side ventricle wall) should be equal to the distance from a probe on the right side temporal area to the nearest wall of the third ventricle (i.e., the right side ventricle wall). For the patient of FIGS. 20–24, the distance from a probe on the left side temporal area to the nearest wall of the third ventricle is 69 mm (FIG. 24(*a*)) and the distance from a probe on the right side temporal area to the nearest wall of the third ventricle is 68 mm (FIG. 24(*b*)). Therefore, based upon this measurement, the shift of midline for the patient from the right side to the left side is 69−68/2=0.5 mm, which is well within the normal limit of ±2 mm.

In order to provide increased confidence in the calculated value, the midline shift can additionally be based upon the measured distance to the farthest wall from the left and right side temporal areas. In this regard, the distance from a probe on the left side temporal area to the farthest wall of the third ventricle (i.e., the right side ventricle wall) should be equal to the distance from a probe on the right side temporal area to the farthest wall of the third ventricle (i.e., the left side ventricle wall) if the third ventrical is centered on the midline. For the patient of FIGS. 20–24, the distance from a probe on the left side temporal area to the farthest wall of the third ventricle is 72 mm (FIG. 24(*a*)) and the distance from a probe on the right side temporal area to the farthest wall of the third ventricle is 72 mm (FIG. 24(*b*)). Therefore, based upon this measurement, the shift of midline for the patient from the right side to the left side is 72−72/2=0.0 mm, which is again within the normal limit of ±2 mm.

It should be noted that while the method in accordance with the present invention for identifying the presence and extent of midline shift preferably includes locating the position of each lateral wall of the third ventricle (as described above), it is also possible to identify the presence and extent of midline shift by, for example, simply locating the nearest third ventricle wall to an ultrasound probe placed on one temporal area of the skull and then locating the nearest third ventricle wall to an ultrasound probe placed on the opposing temporal area.

The TRA technology of the present invention may also be used for the diagnosis and monitoring of other conditions and characteristics. For example, the present invention can be utilized to diagnose traumatic or organic injury to the nervous system such as lateral ventricle shift, fourth ventricle shift, shift of different vessels, brain edema, birth trauma, spinal cord diseases, intramuscular pressure, and severe headache; to monitor blood vessel tension, blood vessel capacitance, linear blood flow velocity, arterial volume blood flow velocity (arterial and venous), coronary blood flow, cardiac output, cardiac excitation-contraction coupling, and intraocular pressure; pupiledema, water content of different tissues and to diagnose intracranial vessels aneurysms, and brain death.

What is claimed is:

1. A method for monitoring intra cranial pressure at a selected site in a brain of a human patient, comprising the steps of:

placing an ultrasound probe on a forehead of a patient;
   transmitting an ultrasound pulse from the ultrasound probe into the forehead of the patent;
   receiving a reflected signal from said ultrasound pulse;
   processing said reflected signal to generate a digital echo encephalogram signal;
   selecting a portion of said echo encephalogram signal;
   integrating the echo encephalogram signal over the selected portion to generate an echo pulsograph signal
   calculating the intra cranial pressure from said echo pulsogram signal in accordance with the formula:

intra cranial pressure=$\rho(t/T)*[t/T]-\beta$ wherein T is the time period between cardiac systoles, t is the time from the beginning of brain pulsatility to the peak following a venous notch (point "B"), $\beta$ is a constant having a value of 9 mm $H_2O$, and $\rho(t/T)$ is a variable function greater than 0 and less than 1, which is characteristic of brain tissue at a site in the brain of the patient corresponding to the selected portion of the echo encephalogram.

2. The method of claim 1, wherein $\rho(t/T)$ is a substantially quadratic function, having a value of about 373 at t/T=0.3, a value of between 373 and 450 at t/T>0.3 and <1, and a value of less than 373 at t/T<0.2.

3. The method of claim 2, wherein $\rho(t/T)$ has a value of about 325 at t/T=0.1, a value of between about 350 and 375 at t/T=0.2, and a value of less than 300 at t/T<0.05.

4. The method of claim 2, wherein the site in the brain of the patient is selected from the group consisting of a third ventricle, the central cerebral vein, lateral ventricle trigon, and suprasellar cistern.

5. The method of claim 3, wherein the site in the brain of the patient is selected from the group consisting of a third ventricle, the central cerebral vein, lateral ventricle trigon, and suprasellar cistern.

6. The method of claim 1, wherein said calculating step further comprises calculating a second resonant frequency of the echopulsogram across a cardiac systole, and identifying the peak following the venous notch based upon said second resonant frequency.

7. The method of claim 6, wherein said calculating step further comprises calculating the second resonant frequency by performing a discrete fourier transform of the echo pulsogram across the cardiac systole. Most preferably, the frequency spectral analysis is a discrete fourier transform.

8. The method of claim 1, wherein the site in the brain of the patient is selected from the group consisting of a third ventricle, the central cerebral vein, lateral ventricle trigon, and suprasellar cistern.

9. The method of claim 1, wherein the probe has a concave transmitting and receiving surface.

10. A method for monitoring intra cranial pressure at a selected site in a brain of a human patient, comprising the steps of:

placing an ultrasound probe on a forehead of a patient;
    transmitting an ultrasound pulse from the ultrasound probe into the forehead of the patent;
    receiving a reflected signal from said ultrasound pulse;
    processing said reflected signal to generate a digital echo encephalogram signal;
    selecting a portion of said echo encephalogram signal;
    integrating the echo encephalogram signal over the selected portion to generate an echo pulsograph signal;
    calculating a second resonant frequency (F) of the echopulsogram across a cardiac systole;
    calculating the intra cranial pressure from said echo pulsogram signal in accordance with the formula:

intra cranial pressure=$\rho(t/T)*[t/T]-\beta$, for F>=4 Hz;

wherein T is the time period between cardiac systoles, t is the time from the beginning of brain pulsatility to the peak following a venous notch (point "B"), $\beta$ is a constant having a value of 9 mm $H_2O$, and $\rho(t/T)$ is a variable function greater than 0 and less than 1, which is characteristic of brain tissue at a site in the brain of the patient corresponding to the selected portion of the echo encephalogram.

11. The method of claim 10, wherein, for F<4 Hz, ICP=$\rho(t/T)*[t/T]$, and $\rho(t/T)$ is a substantially quadratic function, having a value of about 150 at t/T=>0.6, a value of between 100 and 150 at t/T>0.1 and <0.6, and a value of less than 100 at t/T<0.1.

12. The method of claim 11, wherein the site in the brain of the patient is selected from the group consisting of a third ventricle, the central cerebral vein, lateral ventricle trigon, and suprasellar cistern.

13. The method of claim 10, wherein, for F>greater than 20 Hz, $\rho(t/T)$ is a substantially linear function for t/T greater than about 0.5, having a value of about 275 at t/T=0.5 and a value of about 675 at t/T=0.7.

14. The method of claim 13, wherein the site in the brain of the patient is selected from the group consisting of a third ventricle, the central cerebral vein, lateral ventricle trigon, and suprasellar cistern.

15. The method of claim 10, wherein, for F>4 Hz and F<20 Hz, $\rho(t/T)$ is a substantially quadratic function, having a value of about 373 at t/T=0.3, a value of between 373 and 450 at t/T>0.3 and <1, and a value of less than 373 at t/T<0.2.

16. The method of claim 15, wherein, for F>4 Hz and F<20 Hz, $\rho(t/T)$ has a value of about 325 at t/T=0.1, a value of between about 350 and 375 at t/T=0.2, and a value of less than 300 at t/T<0.05.

17. The method of claim 15, wherein the site in the brain of the patient is selected from the group consisting of a third ventricle, the central cerebral vein, lateral ventricle trigon, and suprasellar cistern.

18. The method of claim 10, wherein, for F>4 Hz and F<20 Hz, $\rho(t/T)$ is a substantially quadratic function, having a value of about 373 at t/T=0.3, a value of between 373 and 450 at t/T>0.3 and <1, and a value of less than 373 at t/T<0.2;
    for F<4 Hz, ICP=$\rho(t/T)*[t/T]$, and $\rho(t/T)$ is a substantially quadratic function, having a value of about 150 at t/T=>0.6, a value of between 100 and 150 at t/T>0.1 and <0.6, and a value of less than 100 at t/T<0.1; and
    for F>greater than 20 Hz, $\rho(t/T)$ is a substantially linear function for t/T greater than about 0.5, having a value of about 275 at t/T=0.5 and a value of about 675 at t/T=0.7.

19. The method of claim 8, wherein, for F>4 Hz and F<20 Hz, $\rho(t/T)$ has a value of about 325 at t/T=0.1, a value of between about 350 and 375 at t/T 32 0.2, and a value of less than 300 at t/T<0.05.

20. The method of claim 10, wherein said calculating step further comprises identifying the peak following the venous notch based upon said second resonant frequency.

21. The method of claim 10, wherein said second resonant frequency is calculated by performing a discrete fourier transform of the echo pulsogram across the cardiac systole.

22. The method of claim 10, wherein the site in the brain of the patient is selected from the group consisting of a third ventricle, the central cerebral vein, lateral ventricle trigon, and suprasellar cistern.

23. A method for monitoring pulsatility at a selected site in a brain of a human patient, comprising the steps of
    placing an ultrasound probe on a skull of a patient, the ultrasound probe having a concave transmitting and receiving surface;
    transmitting an ultrasound pulse from the ultrasound probe into the skull of the patent;
    receiving a reflected signal from said ultrasound pulse;
    processing said reflected signal to generate an echo encephalogram signal;
    selecting a portion of said echo encephalogram signal;
    integrating the echo encephalogram signal over the selected portion to generate an echo pulsogram signal, said echo pulsogram signal providing an indication of the pulsatility of a portion of the brain of the human patient corresponding to the selected portion of the echo encephalogram signal.

24. The method according to claim 23, further comprising the step of
    calculating intra cranial pressure at said portion of the brain as a function of the echo pulsogram signal.

25. The method according to claim 23, further comprising the step of
    identifying the presence or absence of midline shift in the brain of the human patient as a function of the echo pulsogram signal.

26. The method according to claim 23, further comprising the step of
    identifying the presence or absence of a shift of a lateral ventricle as a function of the echo pulsogram signal.

27. The method according to claim 23, further comprising the step of
    identifying the presence or absence of a shift of a selected brain vessel as a function of the echo pulsogram signal.

28. The method according to claim 23, further comprising the step of
    identifying the presence or absence of a shift of the fourth ventricle as a function of the echo pulsogram signal.

29. The method according to claim 23, further comprising the step of
    monitoring blood vessel tension at said portion of the brain as a function of the echo pulsogram signal.

30. The method according to claim 23, further comprising the step of
    monitoring blood vessel capacitance at said portion of the brain as a function of the echo pulsogram signal.

31. The method according to claim 23, further comprising the step of
    monitoring linear blood flow velocity at said portion of the brain as a function of the echo pulsogram signal.

32. A method for identifying the presence or absence of midline shift in a brain of a human patient, comprising the steps of
    placing an ultrasound probe on a temporal area of a patient;
    transmitting an ultrasound pulse from the ultrasound probe into the temporal area of the patent;
    receiving a reflected signal from said ultrasound pulse;
    processing said reflected signal to generate a digital echo encephalogram signal;
    selecting a dominant portion of said echo encephalogram signal corresponding to a third ventricle of the patient;
    integrating the echo encephalogram signal over the selected portion to generate an echo pulsogram signal;
    placing an ultrasound probe on an opposite temporal area of a patient;
    transmitting an ultrasound pulse from the ultrasound probe into the opposite temporal area of the patent;
    receiving a reflected signal from said ultrasound pulse;
    processing said reflected signal to generate a digital echo encephalogram signal;
    selecting a dominant portion of said echo encephalogram signal corresponding to the third ventricle of the patient;
    integrating the echo encephalogram signal over the selected portion to generate an opposing echo pulsogram signal,
    identifying the presence or absence of midline shift in the brain of the human patient as a function of the echo pulsogram signal and the opposing echo pulsogram signal.

33. A method for identifying a location of a ventricle or vessel in a brain, comprising the steps of
    (a) placing an ultrasound probe on an appropriate portion of a skull of a patient;
    (b) transmitting an ultrasound pulse from the ultrasound probe into the skull of the patent;
    (c) receiving a reflected signal from said ultrasound pulse;
    (d) processing said reflected signal to generate a digital echo encephalogram signal;
    (e) selecting an initial portion of said echo encephalogram signal corresponding to the vessel or ventricle of interest;
    (f) integrating the echo encephalogram signal over the initial portion to generate an echo pulsogram signal,
    (g) identifying the echopulsogram signal as one of a positive phase signal and a negative phase signal; and
        (1) if the echo pulsogram signal is a positive phase signal, identifying the initial portion of the echo encephalogram as corresponding an outer wall of the vessel or ventricle relative to the ultrasound probe;
        (2) if the echo pulsogram signal is a negative phase signal, identifying the initial portion of the echo encephalogram as corresponding a near wall of the vessel or ventricle relative to the ultrasound probe;
    (h) if a positive phase signal was identified in step(g),
        (1) selecting a second portion of the echoencephalogram signal which corresponds to a location in the brain which is closer to the ultrasound probe than the portion selected in step (e),
        (2) integrating the echo encephalogram signal over the selected second portion to generate an echo pulsogram signal,
        (3) if the echo pulsogram signal is a negative phase signal, identifying the second portion of the echoencephalogram is identified as corresponding to a near wall of the vessel or ventricle.

(4) if the echo pulsogram signal is a positive phase signal, then repeating steps h(1) through (3) by selecting successive second portions of the encephalogram which correspond to locations in the brain which are successively closer to the ultrasound probe, until a negative phase signal is identified.

(i) if a negative phase signal was identified in step(g),
  (1) selecting a second portion of the echoencephalogram signal which corresponds to a location in the brain which is farther from the ultrasound probe than the portion selected in step (e),
  (2) integrating the echo encephalogram signal over the selected second portion to generate an echo pulsogram signal.
  (3) if the echo pulsogram signal is a positive phase signal, identifying the second portion of the echoencephalogram is identified as corresponding to a far wall of the vessel or ventricle.
  (4) if the echo pulsogram signal is a negative phase signal, then repeating steps (i)(1) through (i)(3) by selecting successive second portions of the encephalogram which correspond to locations in the brain which are successively closer to the ultrasound probe, until a negative phase signal is identified.

34. The method of claim 33, further comprising the step of
  identifying as a first distance, based upon the echo encephalogram, a distance from the ultrasound probe to the initial portion,
  identifying as a second distance, based upon the echo encephalogram, a distance from the ultrasound probe to the second portion;
  subtracting the second distance from the first distance to determine a width of the vessel or ventricle of interest.

35. A method for diagnosing the presence or absence of midline shift in a brain of a human patient, comprising the steps of:
  (a) placing an ultrasound probe on a temporal area of a first side of the skull of a patient;
  (b) transmitting an ultrasound pulse from the ultrasound probe into the first side temporal area of the patent;
  (c) receiving a reflected signal from said ultrasound pulse;
  (d) processing said reflected signal to generate a digital echo encephalogram signal;
  (e) selecting a first-side dominant portion of said echo encephalogram signal corresponding to a third ventricle of the patient;
  (f) integrating the echo encephalogram signal over the selected portion to generate a first-side echo pulsogram signal;
  (g) identifying a phase of the first-side echo pulsogram signal as one of a positive phase and a negative phase;
  (h) identifying as a first distance, based upon the echo encephalogram, a distance from the ultrasound probe to the first side dominant portion;
  (i) placing an ultrasound probe on a temporal area of a second side of the skull of a patient;
  (j) transmitting an ultrasound pulse from the ultrasound probe into the second side temporal area of the patent;
  (k) receiving a reflected signal from said ultrasound pulse;
  (l) processing said reflected signal to generate a digital echo encephalogram signal;
  (m) selecting a second-side dominant portion of said echo encephalogram signal corresponding to a third ventricle of the patient;
  (n) integrating the echo encephalogram signal over the selected portion to generate a first-side echo pulsogram signal;
  (o) identifying a phase of the second-side echo pulsogram signal as one of a positive phase and a negative phase;
  (p) if the phase of the second-side echopulsogram is the same as the phase of the first-side echo pulsogram, identifying as a second distance, based upon the echo encephalogram, a distance from the ultrasound probe to the second side dominant portion;
  (q) if the phase of the second-side echopulsogram is not the same as the phase of the first-side echo pulsogram, repeating steps (m) through (p) until a second-side dominant portion of the echo encephalogram is identified which has a corresponding second-side echo pulsogram with the same phase as the first side echo pulsogram.
  (r) diagnosing a presence or absence of midline shift based upon a comparison of the first distance and the second distance.

36. The method of claim 35, further comprising the step of calculating a value for midline shift as M=(first distance−second distance)÷2.

37. The method of claim 35, wherein step (r) further comprises diagnosing a presence of midline shift if a difference between the first distance and the second distance exceeds 2 mm.

* * * * *